US012590919B2

(12) United States Patent (10) Patent No.: US 12,590,919 B2

Watanabe et al. (45) Date of Patent: Mar. 31, 2026

(54) GAS SENSOR ELEMENT AND GAS SENSOR

(71) Applicant: NGK INSULATORS, LTD., Nagoya (JP)

(72) Inventors: Yusuke Watanabe, Nagoya (JP); Daichi Ichikawa, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 328 days.

(21) Appl. No.: 18/353,940

(22) Filed: Jul. 18, 2023

(65) Prior Publication Data

US 2024/0027389 A1 Jan. 25, 2024

(30) Foreign Application Priority Data

Jul. 20, 2022 (JP) ................................. 2022-115402
Jun. 8, 2023 (JP) ................................. 2023-094955

(51) Int. Cl.
| | |
|---|---|
| *G01N 27/407* | (2006.01) |
| *G01N 27/30* | (2006.01) |
| *G01N 27/333* | (2006.01) |
| *G01N 33/00* | (2006.01) |

(52) U.S. Cl.
CPC ......... *G01N 27/304* (2013.01); *G01N 27/333* (2013.01); *G01N 27/4071* (2013.01); *G01N 33/0027* (2013.01)

(58) Field of Classification Search
CPC ............... G01N 27/304; G01N 27/333; G01N 27/4071; G01N 27/4077; G01N 33/0027
See application file for complete search history.

(56) References Cited

U.S. PATENT DOCUMENTS

| | | | | | |
|---|---|---|---|---|---|
| 4,310,401 | A | * | 1/1982 | Stahl | G01N 27/4071 204/426 |
| 7,122,103 | B2 | * | 10/2006 | Isitani | G01N 27/419 204/429 |
| 2011/0083490 | A1 | * | 4/2011 | Murakami | G01N 27/419 73/31.05 |
| 2011/0226618 | A1 | * | 9/2011 | Fujita | G01N 27/4072 204/412 |
| 2015/0075254 | A1 | * | 3/2015 | Sakuma | G01N 27/4072 73/23.31 |
| 2020/0064303 | A1 | * | 2/2020 | Ikeda | G01N 27/4077 |
| 2020/0072784 | A1 | * | 3/2020 | Watanabe | G01N 27/409 |

FOREIGN PATENT DOCUMENTS

JP            2011-102793 A        5/2011

* cited by examiner

*Primary Examiner* — Alexander S Noguerola

(74) *Attorney, Agent, or Firm* — MATTINGLY & MALUR, PC

(57) ABSTRACT

Provided is a gas sensor element or the like in which the diffusion mode of $NO_x$ that reaches a measurement electrode is changed from molecular diffusion to a mode of diffusing while repeatedly colliding with a wall face of a sufficiently narrow flow path. In a gas sensor element according to one aspect of the invention, a porous diffusion layer, which accounts for 70% or more of a cross-section of a flow path of a measurement target gas that is orthogonal to a flow direction of the measurement target gas, has a porosity of 5% or more and 25% or less, and is located at a position that is upstream of the measurement electrode and where the distance to the measurement electrode is 0.15 mm or less.

10 Claims, 16 Drawing Sheets

GAS SENSOR ELEMENT AND GAS SENSOR

CROSS-REFERENCE TO RELATED APPLICATION

The present application claims priority from Japanese application JP 2022-115402, filed on Jul. 20, 2022, and JP 2023-094955, filed on Jun. 8, 2023, the contents of which are hereby incorporated by reference into this application.

TECHNICAL FIELD

The invention relates to a gas sensor element and a gas sensor.

BACKGROUND ART

Various attempts at applying predetermined diffusion resistance to a measurement target gas introduced into an internal space in a gas sensor element, which is used to measure the concentration of a specific gas component in the measurement target gas are conventionally known. For example, JP 2011-102793A discloses a gas sensor element that includes a diffusion control portion that applies predetermined diffusion resistance to the measurement target gas introduced into the internal space.

JP 2011-102793A is an example of related art.

SUMMARY OF THE INVENTION

The inventors found the following problem with the conventional gas sensor element that includes a diffusion control portion such as the aforementioned one. Specifically, the concentration of $H_2O$ in exhaust gases is higher in gasoline vehicles than in diesel vehicles. In addition, hydrogen engine vehicles are expected to be used under highly lean conditions for environmental reasons, and the concentration of $H_2O$ in exhaust gases is also expected to be high. $H_2O$ has a smaller molecular weight than $NO_x$ and $O_2$. The inventors found that the following problem will occur in such an environment with high $H_2O$ concentration.

FIG. 15 shows an example of molecular diffusion in which one molecule is diffused in response to collision with another molecule. The inventors conceived that the following event will occur in a region where molecular diffusion of such a type as that illustrated in FIG. 15 is dominant. That is, since diffusion of molecules proceeds as a result of one molecule colliding with another molecule in molecular diffusion, as illustrated in FIG. 15, the diffusion coefficient changes due to the other molecule with which one molecule collides, i.e. the diffusion coefficient changes depending on the gas composition of a measurement target gas. Thus, the presence of $H_2O$, which has a smaller molecular weight, in the measurement target gas allows $NO_x$ and $O_2$ molecules to diffuse easily between $H_2O$ molecules, and it is conceivable that the amount of $NO_x$ and $O_2$ gases reaching a measurement electrode for measuring the concentration of a specific gas component in the measurement target gas will increase. The inventors conceived that, consequently, $NO_x$ output may vary and the measurement electrode may be more susceptible to deterioration depending on the $H_2O$ concentration (e.g. as the $H_2O$ concentration increases). The inventors confirmed through experiments that $NO_x$ output is more likely to vary and the deterioration of the measurement electrode is accelerated at higher $H_2O$ concentration than at lower concentration.

FIG. 16 shows an example of Knudsen diffusion, which is a diffusion mode different from molecular diffusion. In Knudsen diffusion, diffusion of a certain molecule is promoted as a result of the molecule colliding with a porous wall (a wall face of a flow path), as illustrated in FIG. 16. Since the pore size in the wall face is determined during burning, the diffusion coefficient does not change even if the gas composition in the measurement target gas changes. The inventors then found the following method useful as a solution to the aforementioned problem that is considered to be caused by molecular diffusion of $NO_x$ under high $H_2O$ concentration. That is, the inventors found it useful to adopt a method of changing the diffusion mode of $NO_x$ that reaches the measurement electrode from molecular diffusion to a mode of diffusing while repeatedly colliding with a wall face of a sufficiently narrow channel, as in Knudsen diffusion illustrated in FIG. 16.

In one aspect, the present invention has been made in view of these circumstances, and an object of the invention is to provide a gas sensor element or the like in which the diffusion mode of $NO_x$ that reaches the measurement electrode is changed from molecular diffusion to a mode of diffusing while repeatedly colliding with a wall face of a sufficiently narrow flow path.

The present invention adopts the following configurations in order to solve the aforementioned problem.

A gas sensor element according to a first aspect includes: an element substrate having a surface in which a gas inlet is open, and including an internal space into which a measurement target gas is introduced from the gas inlet; a leading end protection layer covering at least a face of the element substrate in which the gas inlet is open; a measurement electrode provided in the internal space; and a porous diffusion layer located at a position that is upstream of the measurement electrode in a flow direction of the measurement target gas and where a distance to the measurement electrode is 0.15 mm or less. The porous diffusion layer has a porosity that is 5% or more and 25% or less and is lower than the porosity of the leading end protection layer. The porous diffusion layer has a face orthogonal to the flow direction of the measurement target gas, the face accounting for 70% or more of a cross-section of a flow path of the measurement target gas, the cross-section being orthogonal to the flow direction of the measurement target gas. Note that, if the porous diffusion layer includes two or more faces (layers) with different porosities, the average porosity of the porous diffusion layer may be 5% or more and 25% or less, and the average porosity of the porous diffusion layer may be lower than the porosity of the leading end protection layer.

In this configuration, the porous diffusion layer, which has a porosity of 5% or more and 25% and lower than the leading end protection layer, is located at a position that is upstream of the measurement electrode in the flow direction of the measurement target gas and where the distance to the measurement electrode is 0.15 mm or less. The face (the area of the face) of the porous diffusion layer that is orthogonal to the flow direction of the measurement target gas accounts for 70% or more of the cross-section (the area of the cross-section) of the flow path of the measurement target gas that is orthogonal to the flow direction of the measurement target gas. In other words, the porous diffusion layer is located at a position that is upstream of the measurement electrode and where the distance to the measurement electrode is 0.15 mm or less, and accounts for (blocks) a predetermined region (70% or more) of the flow path, in the flow direction of the measurement target gas.

The porous diffusion layer makes it possible to make the diffusion mode around the measurement electrode, i.e. the diffusion mode of the measurement target gas moving toward the measurement electrode through the flow path, a mode of diffusing while repeatedly colliding with a wall face of a sufficiently narrow flow path, as in Knudsen diffusion. With this, even if $H_2O$ gas is present in the measurement target gas, the gas sensor element can reduce the impact of $H_2O$ gas on $NO_x$ gas (and $O_2$ gas) by means of the porous diffusion layer. Specifically, the gas sensor element can suppress fluctuations in $NO_x$ output and deterioration of the measurement electrode, which are caused by molecular diffusion of $NO_x$ under high $H_2O$ concentration, by means of the porous diffusion layer.

Here, if a porous diffusion layer having large diffusion resistance is provided around the measurement electrode, the porous diffusion layer may be clogged with poisonous substances or the like. The gas sensor element includes the leading end protection layer that covers at least the face of the element substrate in which the gas inlet is open. This allows the gas sensor element to trap the poisonous substance or the like using the leading end protection layer, i.e. capture the poisonous substance or the like using the leading end protection layer.

Particularly, in the gas sensor element, the porosity of the leading end protection layer is larger (higher) than porosity of the porous diffusion layer that blocks the predetermined region of the flow path at a position where the distance to the measurement electrode is 0.15 mm or less. The gas sensor element can avoid situations where the leading end protection layer is clogged with poisonous substances or the like and $NO_x$ output decreases, as a result of the porosity of the leading end protection layer being larger than the porosity of the porous diffusion layer.

A gas sensor element according to a second aspect may be the gas sensor according to the first aspect that further includes a diffusion control portion configured to apply predetermined diffusion resistance to the measurement target gas in the internal space. For example, the diffusion control portion has a porosity lower than the porosity of the porous diffusion layer, and is located upstream of measurement electrode in the flow direction of the measurement target gas. The flow path has at least one face defined by the diffusion control portion.

The gas sensor element of this configuration also includes the diffusion control portion that is located upstream of the measurement electrode and has a porosity lower (smaller) than the porosity of the porous diffusion layer. Further, the flow path has at least one face defined (demarcated) by the diffusion control portion. In other words, at least one face of the flow path of the measurement target gas moving toward the measurement electrode is defined by the diffusion control portion, which is denser (has a lower porosity) than the porous diffusion layer. Hence, the gas sensor element can guide the measurement target gas to the measurement electrode using the flow path that has at least one face defined by the diffusion control portion, which is denser than the porous diffusion layer. The gas sensor element can reduce the likelihood of a situation where, for example, the measurement target gas leaks out from an intermediate portion of the flow path and reaches the measurement electrode without the diffusion mode being changed by the porous diffusion layer. Thus, the gas sensor element can bring the diffusion mode of the measurement target gas moving toward the measurement electrode closer to a favorable diffusion mode, such as Knudsen diffusion, by means of the porous diffusion layer that blocks the predetermined region of the flow path through which the measurement target gas is guided.

A gas sensor element according to a third aspect may be the gas sensor element according to the second aspect wherein the porous diffusion layer is in contact with the diffusion control portion and a face defining the internal space.

In this configuration, the porous diffusion layer is in contact with diffusion control portion and the face defining the internal space. In other words, no space (gap) is present between the porous diffusion layer and the diffusion control portion and between the porous diffusion layer and the face defining the internal space. The gas sensor element can achieve the following effects as a result of the gap being eliminated between the porous diffusion layer and the diffusion control portion and the gap between the porous diffusion layer and the face defining the internal space. That is, the gas sensor element can prevent the measurement target gas from reaching the measurement electrode from at least either the gap between the porous diffusion layer and the diffusion control portion or the gap between the porous diffusion layer and the face defining the internal space. This means that the gas sensor element can reduce the likelihood of a situation where, for example, the measurement target gas leaks out from an intermediate portion of the flow path and reaches the measurement electrode without the diffusion mode being changed by the porous diffusion layer. Thus, the gas sensor element can bring the diffusion mode of the measurement target gas moving toward the measurement electrode closer to a favorable diffusion mode, such as Knudsen diffusion, by means of the porous diffusion layer that blocks the predetermined region of the flow path through which the measurement target gas is guided.

A gas sensor element according to a fourth aspect may be the gas sensor element according to the second or third aspect wherein the flow path has at least two faces defined by the diffusion control portion.

In this configuration, at least two faces of the flow path are defined by the diffusion control portion, and the diffusion control portion is denser (i.e. has a lower porosity) than the porous diffusion layer, as mentioned above. In other words, the gas sensor element defines (demarcates) at least two faces of the flow path that guides the measurement target gas to the measurement electrode, by means of the diffusion control portion that is denser than the porous diffusion layer. Hence, the gas sensor element can guide the measurement target gas to the measurement electrode using the flow path that has at least two faces defined by the diffusion control portion that is denser than the porous diffusion layer. The gas sensor element can further reduce the likelihood of a situation where, for example, the measurement target gas leaks out from an intermediate portion of the flow path and reaches to the measurement electrode without the diffusion mode being changed by the porous diffusion layer. Thus, the gas sensor element can bring the diffusion mode of the measurement target gas moving toward the measurement electrode closer to a favorable diffusion mode, such as Knudsen diffusion, by means of the porous diffusion layer that blocks the predetermined region of the flow path through which the measurement target gas is guided.

A gas sensor element according to a fifth aspect may be the gas sensor element according to any one of the first to fourth aspects wherein a distance from an outermost face of the leading end protection layer to the gas inlet is 0.2 mm or more.

5

In the gas sensor element of this configuration, the distance from the outermost face of the leading end protection layer to the gas inlet is 0.2 mm or more. The gas sensor element can achieve the following effects as a result of the distance from the outermost face of the leading end protection layer to the gas inlet being sufficiently long (specifically, 0.2 mm or more), i.e. the thickness of the leading end protection layer being sufficiently large. That is, the gas sensor element can reliably trap (capture) poisonous substances or the like in the leading end protection layer even in a harsh environment with a large amount of poisonous substances or the like, and can prevent clogging caused by poisonous substances or the like in the vicinity of the gas inlet and avoid a decrease in $NO_x$ sensitivity.

A gas sensor element according to a sixth aspect may be the gas sensor element according to any one of the first to fifth aspects wherein the leading end protection layer includes at least: an internal leading end protection layer in contact with the face of the element substrate in which the gas inlet is open; and an external leading end protection layer constituting an outermost face of the leading end protection layer. The internal leading end protection layer has a porosity larger than a porosity of the external leading end protection layer. The internal leading end protection layer has a thickness that is 30% or more and 90% or less of a thickness of the leading end protection layer.

In this configuration, the leading end protection layer includes at least the internal leading end protection layer that is in contact with the face of the element substrate in which the gas inlet is open, and the external leading end protection layer that constitutes the outermost face of the leading end protection layer. The porosity of the internal leading end protection layer is larger than porosity of the external leading end protection layer, and the thickness of the internal leading end protection layer is 30% or more and 90% or less of the thickness of the leading end protection layer.

The gas sensor element can prevent clogging caused by poisonous substances or the like in the vicinity of the gas inlet and avoid a decrease in $NO_x$ sensitivity, as a result of the porosity of the internal leading end protection layer being larger than the porosity of the external leading end protection layer.

Particularly, the gas sensor element can achieve the following effects due to an increased thickness of the internal leading end protection layer that has a porosity larger than the external leading end protection layer, i.e. an increased proportion of the thickness of the internal leading end protection layer to the thickness of the leading end protection layer. That is, securing a sufficient thickness of the internal leading end protection layer having a large porosity makes it possible to prevent clogging caused by poisonous substances or the like in the vicinity of the gas inlet, particularly to reduce the likelihood of clogging in a layer close to the gas inlet (i.e. the internal leading end protection layer). In other words, the internal leading end protection layer that is in contact with the gas inlet can be prevented from clogged with poisonous substances or the like, due to the proportion of the thickness of the internal leading end protection layer having a larger porosity to the thickness of the leading end protection layer being 30% to 90%.

A gas sensor according to one aspect of the invention may be configured to measure an amount of a specific gas component in the measurement target gas, using the gas sensor element according to each of the above aspects. This gas sensor changes the diffusion mode of $NO_x$ that reaches the measurement electrode from molecular diffusion to a mode of diffusing while repeatedly colliding with a wall face of a sufficiently narrow flow path. Thus, in this gas sensor, the porous diffusion layer can suppress fluctuations in $NO_x$ output and deterioration of the measurement electrode, which are considered to be caused by molecular diffusion of $NO_x$ under high $H_2O$ concentration.

According to the present invention, it is possible to provide a gas sensor element or the like in which the diffusion mode of $NO_x$ that reaches the measurement electrode is changed from molecular diffusion to a mode of diffusing while repeatedly colliding with a wall face of a sufficiently narrow flow path.

EMBODIMENT OF THE INVENTION

Figure 1:
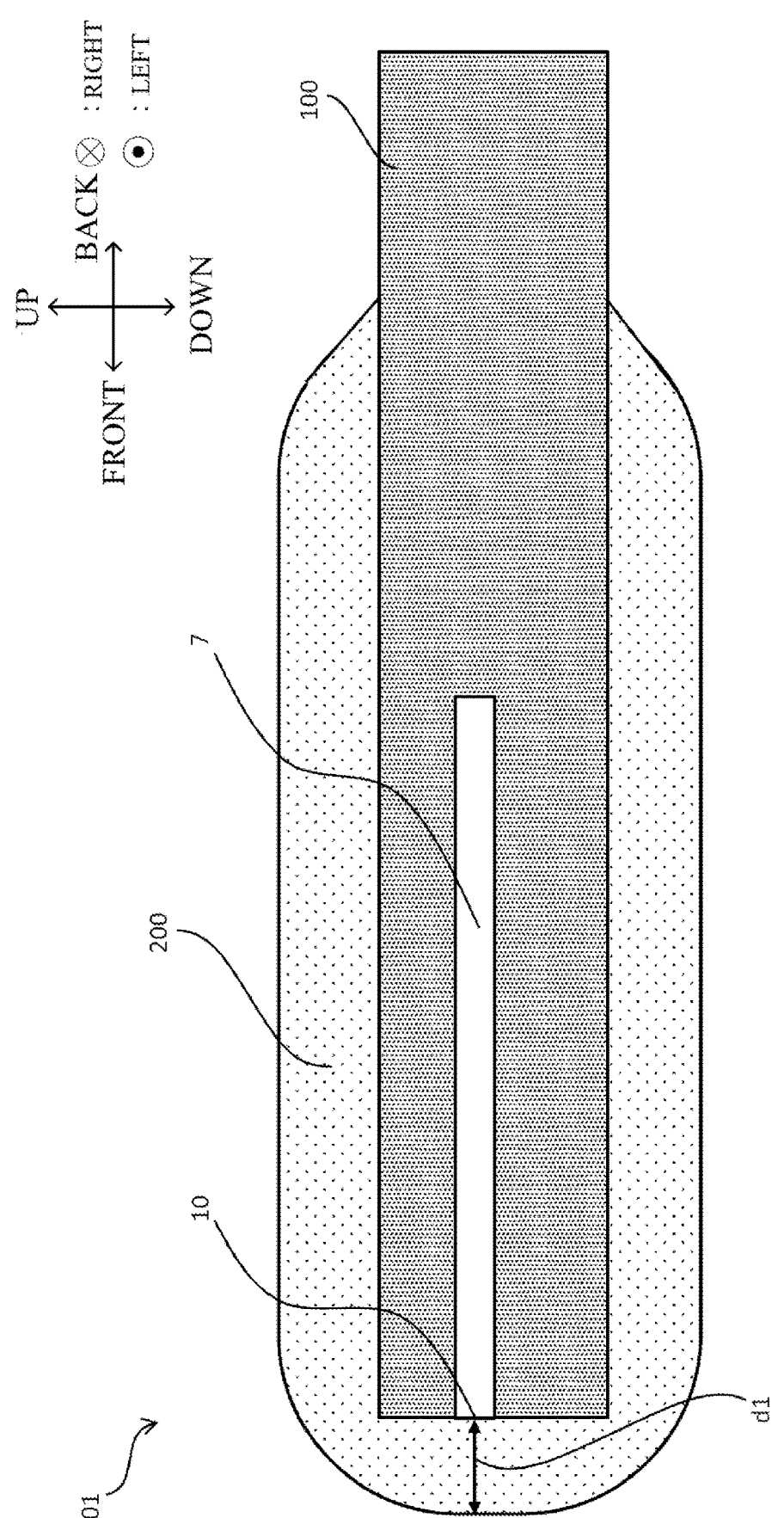
FIG. 1 is a cross-sectional schematic view that schematically shows an example of a configuration of a sensor element according to an embodiment.

An embodiment of one aspect of the present invention (hereinafter also referred to as "the present embodiment") will be described below with reference to the drawings. Note that the following embodiment is in all respects merely illustrative of the invention. It goes without saying that various modifications and variations can be made without departing from the scope of the invention. That is, specific configurations according to the embodiment may be adopted, as appropriate, to implement the invention.

The inventors confirmed that the higher the $H_2O$ concentration in a measurement target gas is, the more likely $NO_x$ output is to vary, and the quicker the measurement electrode degrades. For example, it was confirmed that $NO_x$ output is more likely to vary and the measurement electrode deteriorates more quickly in an environment with higher $H_2O$ concentration (under higher $H_2O$ concentration) where the $H_2O$ concentration in the measurement target gas is 20% or more (specifically, around 25%). One possible contributing factor to this problem, namely fluctuations in $NO_x$ output and the deterioration of the measurement electrode under high $H_2O$ concentration, is that the diffusion mode around a measurement electrode 44 is molecular diffusion. The inventors then confirmed that the aforementioned problem could be solved by changing the diffusion mode around the measurement electrode 44 from molecular diffusion to a mode of diffusing while repeatedly colliding with a wall face of a sufficiently narrow flow path, as in Knudsen diffusion.

In a gas sensor element 101 according to the present embodiment, a porous diffusion layer 91, whose porosity is 5% or more and 25% or less, is provided around the measurement electrode 44. Specifically, the porous diffusion layer 91 is located at a position that is upstream of the measurement electrode 44 in a flow direction DR of a measurement target gas and where the distance to the measurement electrode 44 is 0.15 mm or less. The porous diffusion layer 91 blocks a predetermined region of a flow path CH of the measurement target gas moving toward the measurement electrode 44. Specifically, the area of a face of the porous diffusion layer 91 that is orthogonal to the flow direction DR of the measurement target gas accounts for (blocks) 70% or more of the area of a cross-section of the flow path CH of the measurement target gas that is orthogonal to the flow direction DR of the measurement target gas. The gas sensor element 101 makes the diffusion mode around the measurement electrode 44 favorable by means of the porous diffusion layer 91, which is located at a position that is upstream of the measurement electrode 44 and where the distance to measurement electrode 44 is 0.15 mm or less, and which blocks a predetermined region of flow path CH. Specifically, the gas sensor element 101 changes the diffusion mode around the measurement electrode 44 from molecular diffusion to a mode of diffusing while repeatedly colliding with a wall face of a sufficiently narrow flow path, as in Knudsen diffusion, by means of the porous diffusion layer 91. This allows the gas sensor element 101 to reduce the impact of $H_2O$ gas on $NO_x$ gas (and $0_2$ gas) even if $H_2O$ gas is present in the measurement target gas, and to suppress fluctuations in $NO_x$ output and the deterioration of the measurement electrode 44, by means of the porous diffusion layer 91. That is, the gas sensor element 101 suppresses the deterioration of the measurement electrode 44 under high $H_2O$ concentration, e.g. when the measurement electrode 44 is driven for a long period of time under high $H_2O$ concentration. The gas sensor element 101 also suppresses fluctuations in $NO_x$ output under high $H_2O$ concentration, e.g. reduces $H_2O$ dependence of $NO_x$ output while the $NO_x$ gas is flowing, and thus increases the accuracy of $NO_x$ concentration measurements. Although the details will be described later, the porosity in the present embodiment is a value derived, for example, by applying a known image processing method (e.g. binarization) to an image (SEM image)

observed and obtained using a scanning electron microscope (SEM). For example, the gas sensor element 101 is cut to obtain a face to be observed that is a cross-section of a certain layer, and the cut face is resin-filled and polished to make an observation sample. The SEM image of this layer is then obtained by capturing an image of the face to be obtained of the observation sample using a SEM photograph (secondary electron image with an accelerating voltage of 15 kV, a magnification of 1000×; however, if a magnification of 1000× is not appropriate, a magnification greater than 1000× and 5000× or less is used). Next, the obtained image is subjected to image analysis to determine a threshold value using a discriminant analysis method (Otsu binarization) based on the luminance distribution of luminance data of pixels in the image. Thereafter, each pixel in the image is binarized into an object part and a pore part based on the determined threshold value, and the area of the object part and the area of the pore part are calculated. Then, the ratio of the area of the pore part to the total area (total area of the object part and the pore part) is derived as the porosity [%] of the layer.

Further, in the gas sensor element 101 according to the present embodiment, a leading end protection layer 200 covers at least a face of an element substrate 100 in which a gas inlet 10 is open. The gas sensor element 101 traps (captures) poisonous substances or the like that cause clogging in the porous diffusion layer 91 that blocks the predetermined region of the flow path CH around the measurement electrode 44, by means of the leading end protection layer 200. Specifically, the gas sensor element 101 traps poisonous substances or the like by means of the leading end protection layer 200 whose porosity is larger than that of the porous diffusion layer 91, thus preventing clogging around the measurement electrode 44, e.g. clogging in the porous diffusion layer 91. Hence, the gas sensor element 101 can prevent the porous diffusion layer 91 that blocks the predetermined region of the flow path CH around the measurement electrode 44 from being clogged with poisonous substances or the like, resulting in lower $NO_x$ output and lower measurement accuracy. The gas sensor element 101 according to the present embodiment will be described below in detail with reference to FIG. 1.

Example Configuration

FIG. 1 is a cross-sectional schematic view that schematically shows an example of a configuration of the gas sensor element 101 according to the present embodiment. As illustrated in FIG. 1, the gas sensor element 101 includes an element substrate 100 and a leading end protection layer 200. The element substrate 100 has a gas inlet 10 that is open in a surface thereof, and a measurement target gas is introduced from the gas inlet 10 to a measurement target gas flow portion 7, which is an internal space in the element substrate 100. In the example shown in FIG. 1, the gas inlet is open in a front surface (on the leading end side) of the element substrate 100. In the following description, there are cases where the front surface (on the leading end side) of the element substrate 100 is referred to as a "leading end face" of the element substrate 100. In FIG. 1, the front (the leading end) side of the element substrate 100 corresponds to the left side of the sheet.

Leading End Protection Layer

The leading end protection layer 200 covers at least the face of the element substrate 100 (the leading end face of element substrate 100) in which the gas inlet 10 is open. In the example shown in FIG. 1, the leading end protection layer 200 covers the leading end face of the element substrate 100 and four side faces of the element substrate 100 that are continuous with the leading end face.

As will be described later in detail, providing the leading end protection layer 200 enables poisonous substances or the like that cause clogging in the porous diffusion layer 91 provided around the measurement electrode 44 to be trapped (captured) by the leading end protection layer 200. That is, the gas sensor element 101 can prevent the porous diffusion layer 91 from being clogged, as a result of the leading end protection layer 200 capturing poisonous substances or the like. Further, the porosity of the leading end protection layer 200 is higher than the porosity of the porous diffusion layer 91 that is provided around the measurement electrode 44. The gas sensor element 101 can thus prevent a situation where the leading end protection layer 200 itself is clogged with poisonous substances or the like, resulting in a decrease in $NO_x$ output of the gas sensor element 101.

The leading end protection layer 200 has a predetermined thickness; specifically, a distance d1 from the outermost face of the leading end protection layer 200 to the gas inlet 10 is 0.2 mm or more. The gas sensor element 101 can achieve the following effects as a result of the distance d1 from the outermost face of the leading end protection layer 200 to the gas inlet 10 being sufficiently long (specifically, 0.2 mm or more), i.e. the leading end protection layer 200 being sufficiently thick. That is, even in a harsh environment with a large amount of poisonous substances or the like, the leading end protection layer 200 can reliably trap (capture) the poisonous substances or the like can, thus preventing clogging caused by the poisonous substances or the like in the vicinity of the gas inlet 10 and avoiding a decrease in $NO_x$ sensitivity.

Element Substrate

Figure 2:
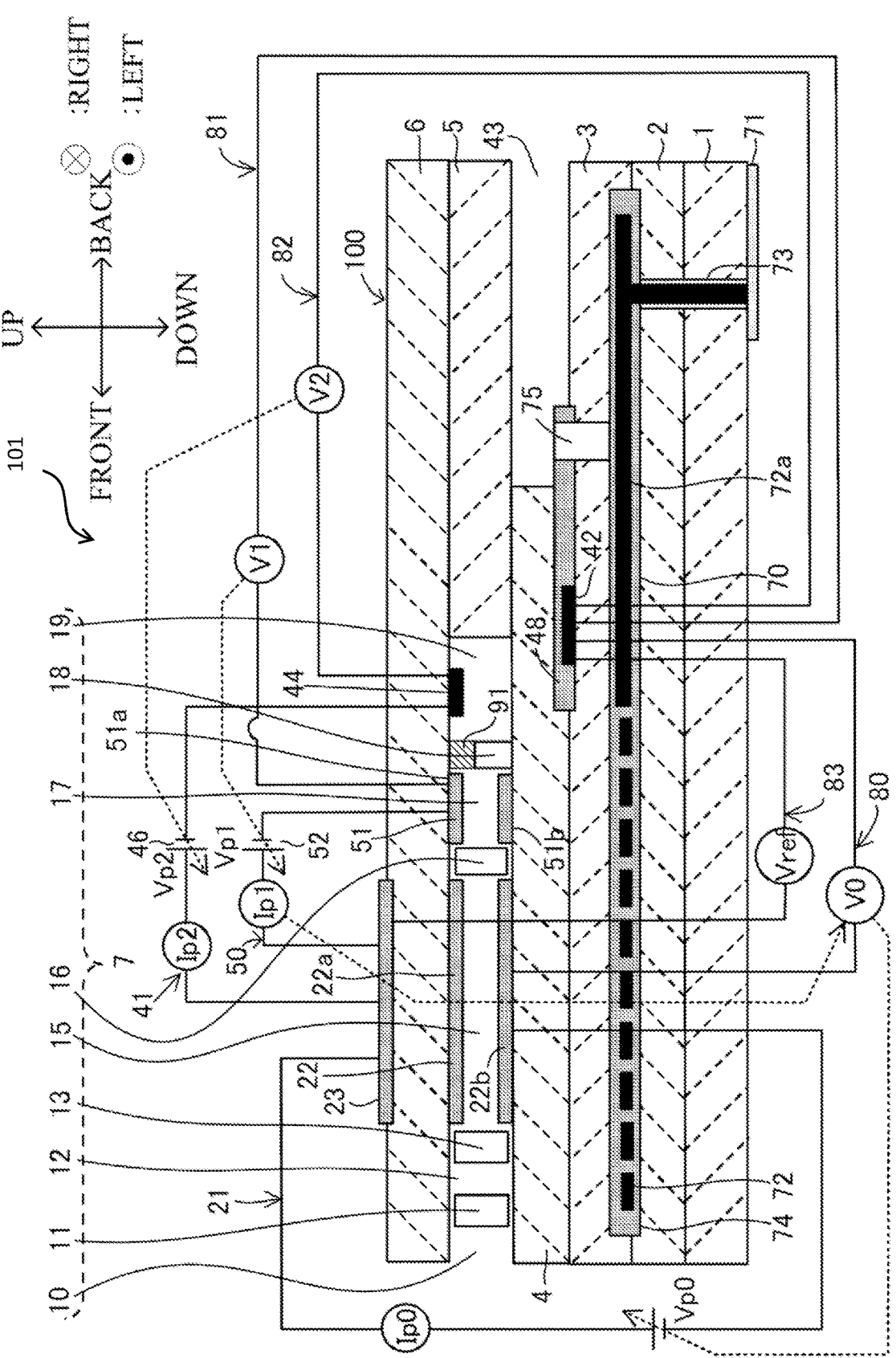
FIG. 2 shows a cross-sectional schematic view that shows an example of a configuration of an element substrate included in the sensor element in FIG. 1.

FIG. 2 is a cross-sectional schematic view that schematically shows an example of a configuration of the element substrate 100 of the gas sensor element 101. The element substrate 100 has a slender and elongated plate shape extending in a lengthwise direction (axial direction), for example, and also has a rectangular shape, for example. The element substrate 100 illustrated in FIG. 2 has a leading end portion and a rear end portion as end portions in the lengthwise direction. In the following description, the leading end portion corresponds to the left end portion (i.e. front end portion) in FIG. 2, and the rear end portion corresponds to the right end portion (i.e. rear end portion) in FIG. 2. Note that the shape of the element substrate 100 need not be limited to this example, and may be selected as appropriate, according to the mode of implementation. In the following description, the distal side of the sheet of FIG. 2 corresponds to the right side of the element substrate 100, and the proximal side of the sheet corresponds to the left side of the element substrate 100.

As illustrated in FIG. 2, the element substrate 100 includes a laminate formed by stacking a first substrate layer 1, a second substrate layer 2, a third substrate layer 3, a first solid electrolyte layer 4, a spacer layer 5, and a second solid electrolyte layer 6, in this order from the bottom. The layers 1 to 6 are each constituted by an oxygen-ion-conductive solid electrolyte layer made of zirconia ($ZrO_2$) or the like. The solid electrolyte that forms the layers 1 to 6 may be dense. Being dense means having a porosity of 5% or less.

For example, the element substrate 100 is produced by performing steps of predetermined processing, wiring pattern printing, and the like, on a ceramic green sheet corresponding to each layer, then stacking the processed layers, and firing and integrate the layers. As an example, the element substrate 100 is a laminate of a plurality of ceramic layers. In the present embodiment, an upper face of the second solid electrolyte layer 6 constitutes an upper face of the element substrate 100, a lower face of the first substrate layer 1 constitutes a lower face of the element substrate 100, and side faces of the layers 1 to 6 constitute side faces of the element substrate 100.

In the present embodiment, an internal space that receives the measurement target gas from an external space is present at one leading end portion of the element substrate 100, between the lower face of the second solid electrolyte layer 6 and the upper face of the first solid electrolyte layer 4. The internal space according to the present embodiment includes the gas inlet 10, a first diffusion control portion 11, a buffer space 12, a second diffusion control portion 13, a first internal cavity 15, a third diffusion control portion 16, a second internal cavity 17, a fourth diffusion control portion 18, and a third internal cavity 19, which are adjacent to each other and connected in this order. In other words, the internal space according to the present embodiment has a three-cavity structure (the first internal cavity 15, the second internal cavity 17, and the third internal cavity 19).

In one example, the internal space is provided by hollowing out a portion of the spacer layer 5. An upper portion of the internal space is demarcated by the lower face of the second solid electrolyte layer 6. A lower portion of the internal space is demarcated by the upper face of the first solid electrolyte layer 4. Side portions of the internal space are demarcated by the side faces of the spacer layer 5.

The first diffusion control portion 11 is a member (portion) that applies predetermined diffusion resistance to the measurement target gas. In the example shown in FIG. 2, the first diffusion control portion 11 forms two slits (flow paths CH through which the measurement target gas flows) that are laterally elongated (i.e. have openings whose lengthwise direction is a direction perpendicular to the drawing). For example, the first diffusion control portion 11 is a bridging portion (a first bridging portion) that bridges the hollowed space in the spacer layer 5, and the space between the first diffusion control portion 11 and the layer 6 and the space between the first diffusion control portion 11 and the layer 4 serve as the slits, i.e. the flow paths CH through which the measurement target gas flows. Similarly, the second diffusion control portion 13, the third diffusion control portion 16, and the fourth diffusion control portion 18 are members that apply predetermined diffusion resistance to the measurement target gas. The second diffusion control portion 13, the third diffusion control portion 16, and the fourth diffusion control portion 18 each have a hole (a flow path CH through which the measurement target gas flows) whose length in a direction perpendicular to the drawing is shorter than the lengths of the first internal cavity 15, the second internal cavity 17, and the third internal cavity 19.

As illustrated in FIG. 2, the second diffusion control portion 13 and the third diffusion control portion 16 may both form two slits (flow paths CH) that are laterally elongated (i.e. have openings whose lengthwise direction is perpendicular to the drawing), similarly to the first diffusion control portion 11. Meanwhile, the fourth diffusion control portion 18 may form one slit (a flow path CH) that is laterally elongated (i.e. has an opening whose lengthwise direction is perpendicular to the drawing) and formed as a gap between the fourth diffusion control portion 18 and the lower face of the second solid electrolyte layer 6. That is, the fourth diffusion control portion 18 may be in contact with the upper face of the first solid electrolyte layer 4. For example, the second diffusion control portion 13 serves as a bridging portion (a second bridging portion) that bridges the hollowed space in the spacer layer 5, and the space between the second diffusion control portion 13 and the layer 6 and the space between the second diffusion control portion 13 and the layer 4 serve as the slits, i.e. the flow paths CH through which the measurement target gas flows. For example, the third diffusion control portion 13 serves as a bridging portion (a third bridging portion) that bridges the hollowed space in the spacer layer 5, and the space between the third diffusion control portion 16 and the layer 6 and the space between the third diffusion control portion 16 and the layer 4 serve as the slits, i.e. the flow paths CH through which the measurement target gas flows. For example, the fourth diffusion control portion 18 serves as a bridging portion (a fourth bridging portion) that bridges the hollowed space in the spacer layer 5, and the space between the fourth diffusion control portion 18 and the layer 6 serves as a slit, i.e. the flow path CH through which the measurement target gas flows. The second diffusion control portion 13, the third diffusion control portion 16, and the fourth diffusion control portion 18 will be described later in more detail. The portion (internal space) from the gas inlet 10 to the third internal cavity 19 is referred to as a measurement target gas flow portion 7.

A reference gas introduction space 43 is located farther from the leading end side (i.e. the front side of the element substrate 100) than the measurement target gas flow portion 7, at a position between the upper face of the third substrate layer 3 and the lower face of the spacer layer 5 at which side portions are demarcated by the side faces of the first solid electrolyte layer 4. A reference gas, such as air, is introduced into the reference gas introduction space 43. Note that the configuration of the element substrate 100 need not be limited to this example. As another example, the first solid electrolyte layer 4 may extend to the rear end of the element substrate 100, and the reference gas introduction space 43 may be omitted. In this case, an air introduction layer 48 may extend to the rear end of the element substrate 100.

The air introduction layer 48 is provided at a portion of the upper face of the third substrate layer 3 adjacent to the reference gas introduction space 43. The air introduction layer 48 is made of porous alumina, and the reference gas is introduced thereinto via the reference gas introduction space 43. In addition, the air introduction layer 48 covers a reference electrode 42.

The reference electrode 42 is sandwiched between the upper face of the third substrate layer 3 and the first solid electrolyte layer 4, and is surrounded by the air introduction layer 48 that is connected to the reference gas introduction space 43. The reference electrode 42 is used to measure the oxygen concentration (oxygen partial pressure) within the first internal cavity 15 and the second internal cavity 17. The details will be described later.

The gas inlet 10 is a portion of the measurement target gas flow portion 7 that is open to the external space. The element substrate 100 takes the measurement target gas thereinto from the external space through the gas inlet 10. The gas inlet 10 of the present embodiment is disposed in the leading end face (front face) of the element substrate 100, as illustrated in FIG. 2. In other words, the measurement target gas flow portion 7 has an opening in the leading end face of the element substrate 100. Note that it is not essential for the measurement target gas flow portion 7 to have an opening in the leading end face of the element substrate 100, i.e. to dispose the gas inlet 10 in the leading end face of the element substrate 100. The element substrate 100 need only be capable of taking the measurement target gas into the measurement target gas flow portion 7 from the external space, and the gas inlet 10 may alternatively be disposed in the right face or the left face of the element substrate 100, for example.

The first diffusion control portion 11 is a portion that applies predetermined diffusion resistance to the measurement target gas taken in from the gas inlet 10.

The buffer space 12 is a space for guiding the measurement target gas introduced from the first diffusion control portion 11 to the second diffusion control portion 13.

The second diffusion control portion 13 is a portion that applies predetermined diffusion resistance to the measurement target gas introduced into the first internal cavity 15 from the buffer space 12.

When the measurement target gas is introduced from the space outside the element substrate 100 into the first internal cavity 15, there are cases where the measurement target gas is rapidly taken from the gas inlet into the element substrate 100 due to pressure fluctuations in the measurement target gas in the external space (i.e. pulsations in exhaust pressure if the measurement target gas is exhaust gas of an automobile). Even in this case, this configuration causes the measurement target gas to not be introduced directly into the first internal cavity 15, but introduced into the first internal cavity 15 after the concentration fluctuations in the measurement target gas have been cancelled out through the first diffusion control portion 11, the buffer space 12, and the second diffusion control portion 13. This makes the concentration fluctuations in the measurement target gas introduced into the first internal cavity 15 substantially negligible.

The first internal cavity 15 is provided as a space for adjusting the oxygen partial pressure in the measurement target gas introduced through the second diffusion control portion 13 (i.e. through the flow paths CH formed by the second diffusion control portion 13). The oxygen partial pressure is adjusted by operation of the main pump cell 21.

The main pump cell 21 is an electro-chemical pump cell constituted by the internal pump electrode 22, the external pump electrode 23, and the second solid electrolyte layer 6 that is sandwiched by these electrodes. The internal pump electrode 22 has a ceiling electrode portion 22a provided on substantially the entirety of the lower face of the second solid electrolyte layer 6 adjoining (facing) the first internal cavity 15. The external pump electrode 23 is provided in a region of the upper face of the second solid electrolyte layer 6 that corresponds to the ceiling electrode portion 22a so as to adjoin the external space.

The internal pump electrode 22 is formed so as to extend across the upper and lower solid electrolyte layers that define the first internal cavity 15 (i.e. the second solid electrolyte layer 6 and the first solid electrolyte layer 4), and the spacer layer 5 that forms side walls. Specifically, the ceiling electrode portion 22a is formed on the lower face of the second solid electrolyte layer 6 that forms a ceiling face of the first internal cavity 15, and a bottom electrode portion 22b is formed on the upper face of the first solid electrolyte layer 4 that forms a bottom face. Side electrode portions (not shown) that connect the ceiling electrode portion 22a and the bottom electrode portion 22b are formed on side wall faces (internal faces) of the spacer layer 5 that forms two side wall portions of the first internal cavity 15. In other words, the internal pump electrode 22 is provided in the form of a tunnel in the region in which the side electrode portions are disposed.

The internal pump electrode 22 and the external pump electrode 23 are formed as porous cermet electrodes (e.g. cermet electrodes formed with $ZrO_2$ and Pt containing 1%

Au). Note that the internal pump electrode 22, which comes into contact with the measurement target gas, is made of a material that has a lowered capability of reducing a nitrogen oxide ($NO_x$) component in the measurement target gas.

The element substrate 100 (the gas sensor element 101) is configured such that the main pump cell 21 can apply a desired pump voltage Vp0 between the internal pump electrode 22 and the external pump electrode 23, thereby causing a pump current Ip0 to flow in a positive direction or a negative direction between the internal pump electrode 22 and the external pump electrode 23, so that oxygen in the first internal cavity 15 is pumped out to the external space, or oxygen in the external space is pumped into the first internal cavity 15.

Furthermore, in order to detect the oxygen concentration (oxygen partial pressure) in the atmosphere in the first internal cavity 15, the internal pump electrode 22, the second solid electrolyte layer 6, the spacer layer 5, the first solid electrolyte layer 4, the third substrate layer 3, and the reference electrode 42 constitute an oxygen partial pressure detection sensor cell 80 for main pump control (i.e., an electro-chemical sensor cell).

The element substrate 100 (the gas sensor element 101) is configured to be capable of identifying the oxygen concentration (oxygen partial pressure) in the first internal cavity 15 by measuring an electromotive force V0 in the oxygen partial pressure detection sensor cell 80 for main pump control. Furthermore, the pump current Ip0 is controlled by performing feedback control on Vp0 such that the electromotive force V0 is kept constant. Accordingly, the oxygen concentration in the first internal cavity 15 can be kept at a predetermined constant value.

The third diffusion control portion 16 is a region that applies predetermined diffusion resistance to the measurement target gas whose oxygen concentration (oxygen partial pressure) has been controlled by operation of the main pump cell 21 in the first internal cavity 15, thereby guiding the measurement target gas to the second internal cavity 17.

The second internal cavity 17 is provided as a space for further adjusting the oxygen partial pressure in the measurement target gas that has been introduced through the third diffusion control portion 16 (i.e. through the flow paths CH formed by the third diffusion control portion 16). The oxygen partial pressure is adjusted by operation of the auxiliary pump cell 50.

The auxiliary pump cell 50 is an auxiliary electro-chemical pump cell constituted by an auxiliary pump electrode 51, the external pump electrode 23 (which is not limited to the external pump electrode 23, and may be any appropriate electrode outside the element substrate 100), and the second solid electrolyte layer 6. The auxiliary pump electrode 51 has a ceiling electrode portion 51a provided on substantially the entirety of the lower face of the second solid electrolyte layer 6 facing the second internal cavity 17.

The auxiliary pump electrode 51 with this configuration is disposed inside the second internal cavity 17 in the form of a tunnel similar to the above-described internal pump electrode 22 provided inside the first internal cavity 15. That is, the ceiling electrode portion 51a is formed on the lower face of the second solid electrolyte layer 6 that forms the ceiling face of the second internal cavity 17, and a bottom electrode portion 51b is formed on the upper face of the first solid electrolyte layer 4 that forms the bottom face of the second internal cavity 17. Side electrode portions (not shown) that connect the ceiling electrode portion 51a and the bottom electrode portion 51b are formed on two wall faces of the spacer layer 5 that form side walls of the second internal cavity 17. Thus, the auxiliary pump electrode 51 is in the form of a tunnel.

Note that the auxiliary pump electrode 51 is also made of a material that has a lowered capability of reducing a nitrogen oxide component in the measurement target gas, similarly to the internal pump electrode 22.

The element substrate 100 (the gas sensor element 101) is configured such that the auxiliary pump cell 50 can apply a desired voltage Vp1 between the auxiliary pump electrode 51 and the external pump electrode 23, so that oxygen in the atmosphere in the second internal cavity 17 is pumped out to the external space, or oxygen is pumped from the external space into the second internal cavity 17.

Furthermore, in order to control the oxygen partial pressure in the atmosphere in the second internal cavity 17, the auxiliary pump electrode 51, the reference electrode 42, the second solid electrolyte layer 6, the spacer layer 5, the first solid electrolyte layer 4, and the third substrate layer 3 constitute an oxygen partial pressure detection sensor cell 81 for auxiliary pump control (i.e., an electro-chemical sensor cell).

Note that the auxiliary pump cell 50 performs pumping using a variable power source 52 whose voltage is controlled based on an electromotive force V1 detected by the oxygen partial pressure detection sensor cell 81 for auxiliary pump control. Accordingly, the oxygen partial pressure in the atmosphere in the second internal cavity 17 is controlled to be a partial pressure that is low enough to substantially not affect the $NO_x$ measurement.

Furthermore, a pump current Ip1 is used to control the electromotive force of the oxygen partial pressure detection sensor cell 80 for main pump control. Specifically, the pump current Ip1 is input as a control signal to the oxygen partial pressure detection sensor cell 80 for main pump control, and the electromotive force V0 is controlled so as to keep a constant gradient of the oxygen partial pressure in the measurement target gas that is introduced from the third diffusion control portion 16 into the second internal cavity 17. In the case where the sensor is used as a $NO_x$ sensor, the oxygen concentration in the second internal cavity 17 is kept at a constant value of about 0.001 ppm by operation of the main pump cell 21 and the auxiliary pump cell 50.

The fourth diffusion control portion 18 is a portion that applies predetermined diffusion resistance to the measurement target gas whose oxygen concentration (oxygen partial pressure) has been controlled by operation of the auxiliary pump cell 50 in the second internal cavity 17, and guides this measurement target gas to the third internal cavity 19. The fourth diffusion control portion 18 forms a flow path CH of the measurement target gas from the second internal cavity 17 to the third internal cavity 19. In the example shown in FIG. 2, the fourth diffusion control portion 18 forms the flow path CH as a slit (gap) between the fourth diffusion control portion 18 and the lower face the second solid electrolyte layer 6. That is, the fourth diffusion control portion 18 defines the lower face of the flow path CH of the measurement target gas moving toward the measurement electrode 44, upstream of the measurement electrode 44 in the flow direction DR of the measurement target gas (from the left side to the right side of the sheet in the example shown in FIG. 2).

The fourth diffusion control portion 18 has a porosity lower than that of the later-described porous diffusion layer 91, i.e. is denser than the porous diffusion layer 91. Although the details will be described below with reference to FIGS. 8 and 10 and other figures, if the measurement electrode 44 is provided on the surface (e.g. lower face) of the fourth diffusion control portion, the fourth diffusion control portion is constituted by an oxygen-ion-conductive solid electrolyte layer made or zirconia ($ZrO_2$) or the like. That is, in the case of providing the measurement electrode 44 on the surface of the fourth diffusion control portion, this fourth diffusion control portion is configured as an oxygen-ion-conductive layer that is dense (i.e. has a porosity of 5% or less).

The porous diffusion layer 91 is disposed on a flow path CH. In the example shown in FIG. 2, the porous diffusion layer 91 is provided in contact with the upper face of the fourth diffusion control portion 18, on the flow path CH between the upper face of the fourth diffusion control portion 18 and the lower face of the second solid electrolyte layer 6.

The porous diffusion layer 91 is made of a porous material with a porosity that is 5% or more and 25% or less and is lower than that of the leading end protection layer 200, and may be a porous film that is mainly made of alumina ($Al_2O_3$), for example.

The porous diffusion layer 91 is located upstream of the measurement electrode 44 in the flow direction DR of the measurement target gas, and makes the diffusion mode of the measurement target gas moving toward the measurement electrode 44 favorable. Specifically, the porous diffusion layer 91 makes the diffusion mode around the measurement electrode 44 a mode of diffusing while repeatedly colliding with a wall face of a sufficiently narrow flow path, as in Knudsen diffusion.

The porous diffusion layer 91 is provided on a flow path CH, upstream of the measurement electrode 44 in the flow direction DR of the measurement target gas. In the example shown in FIG. 2, the porous diffusion layer 91 is provided on the flow path CH formed by the fourth diffusion control portion 18 so as to be in contact with the upper face of the fourth diffusion control portion 18, which forms the flow path CH of the measurement target gas from the second internal cavity 17 to the third internal cavity 19.

Although the details will be described later with reference to FIG. 3 and other figures, the porous diffusion layer 91 is provided on the flow path CH at a position where a distance d2 to the measurement electrode 44 is 0.15 mm or less. The area of a face of the porous diffusion layer 91 that is orthogonal to the flow direction DR of the measurement target gas accounts for 70% or more of the area of a cross-section of the flow path CH that is orthogonal to the flow direction DR of the measurement target gas. The gas sensor element 101 achieves the following effects by means of the porous diffusion layer 91, which is located at a position that is upstream of the measurement electrode 44 and where the distance d2 to the measurement electrode 44 is 0.15 mm or less, and which accounts for 70% or more of the area of a cross-section of the flow path CH that is orthogonal to the flow direction DR of the measurement target gas. That is, the gas sensor element 101 makes the diffusion mode around the measurement electrode 44 a mode of diffusing while repeatedly colliding with a wall face of a sufficiently narrow flow path, as in Knudsen diffusion, by means of the porous diffusion layer 91. The gas sensor element 101 can thus suppress fluctuations in $NO_x$ output and the deterioration of the measurement electrode under high $H_2O$ concentration that occur when the diffusion mode around the measurement electrode 44 is molecular diffusion.

The following will describe an example where the porous diffusion layer 91 is a porous layer having a constant porosity of 5% or more and 25% or less throughout. Note that the porosity of the porous diffusion layer 91 need not be constant over the entire porous diffusion layer 91. The porous diffusion layer 91 may alternatively include a plurality of faces (layers) with different porosities. That is, the porosities of two faces of the porous diffusion layer 91 that face opposite sides may be different. For example, the porosity of the porous diffusion layer 91 may be different between an upstream face and a downstream face. Particularly, the porous diffusion layer 91 may have different porosities between a face opposing (facing) the measurement electrode 44 and a face not opposing (not facing) the measurement electrode 44 (e.g. a face facing the measurement target gas flow portion 7). If the porous diffusion layer 91 includes a plurality of faces (layers) with different porosities, the average porosity of the porous diffusion layer 91 is 5% or more and 25% or less and is lower than the porosity of the leading end protection layer 200.

As described above, the gas sensor element 101 includes the fourth diffusion control portion 18 (diffusion control portion) that applies predetermined diffusion resistance to the measurement target gas in the measurement target gas flow portion 7 (internal space). The fourth diffusion control portion 18 is located upstream of the measurement electrode 44 in the flow direction DR of the measurement target gas. The porosity of the fourth diffusion control portion 18 is lower than the porosity of the porous diffusion layer 91; i.e. the fourth diffusion control portion 18 is denser than the porous diffusion layer 91. In the gas sensor element 101, the fourth diffusion control portion 18 defines (demarcates) at least one face of the flow path CH that has a predetermined region blocked by the porous diffusion layer 91. In the example shown in FIG. 2, the fourth diffusion control portion 18 defines the lower face of the flow path CH.

In this configuration, the gas sensor element 101 also includes the fourth diffusion control portion 18 that is located upstream of the measurement electrode 44 and has a porosity lower (smaller) than that of the porous diffusion layer 91. The fourth diffusion control portion 18 defines (demarcates) at least one face of the flow path CH, which has a predetermined region blocked by the porous diffusion layer 91. That is, the fourth diffusion control portion 18, which is denser (has a lower porosity) than the porous diffusion layer 91, defines at least one face of the flow path CH of the measurement target gas moving toward the measurement electrode 44. Hence, the gas sensor element 101 can guide the measurement target gas to the measurement electrode 44 using the flow path CH having at least one face defined by the fourth diffusion control portion 18, which is denser than the porous diffusion layer 91. The gas sensor element 101 can reduce the likelihood of a situation where, for example, the measurement target gas leaks out from an intermediate portion of the flow path CH and reaches the measurement electrode 44 without the diffusion mode being changed by the porous diffusion layer 91. Accordingly, the gas sensor element 101 can bring the diffusion mode of the measurement target gas moving toward the measurement electrode 44 closer to a favorable diffusion mode, such as Knudsen diffusion, by means of the porous diffusion layer 91 that blocks the predetermined region of the flow path CH through which the measurement target gas is guided.

The third internal cavity 19 is provided as a space for performing processing regarding measurement of the concentration of nitrogen oxide ($NO_x$) in the measurement target gas that was introduced via the fourth diffusion control portion 18 (i.e. through the flow path CH that is formed by the fourth diffusion control portion 18 and in which the porous diffusion layer 91 is provided). The $NO_x$ concentration is measured by operation of a measurement pump cell 41. In this embodiment, the oxygen concentration (oxygen partial pressure) is adjusted in the first internal cavity 15, and thereafter, the auxiliary pump cell 50 further adjusts, in the second internal cavity 17, the oxygen partial pressure in the measurement target gas that was introduced through the third diffusion control portion 16. The oxygen concentration in the measurement target gas that is introduced from the second internal cavity 17 into the third internal cavity 19 can thus be kept constant with high accuracy. This enables the element substrate 100 according to this embodiment to measure the NO$_x$ concentration with high accuracy.

The measurement pump cell 41 measures the concentration of nitrogen oxide in the measurement target gas, in the third internal cavity 19. The measurement pump cell 41 is an electro-chemical pump cell constituted by a measurement electrode 44, the external pump electrode 23, the second solid electrolyte layer 6, the spacer layer 5, and the first solid electrolyte layer 4. The measurement electrode 44 in the example in FIG. 2 is provided on the lower face of the second solid electrolyte layer 6 adjoining (facing) the third internal cavity 19. As will be described later with reference to FIGS. 8 and 10, the measurement electrode 44 may alternatively be provided on a surface (e.g. lower face) of the fourth diffusion control portion.

Figure 5:
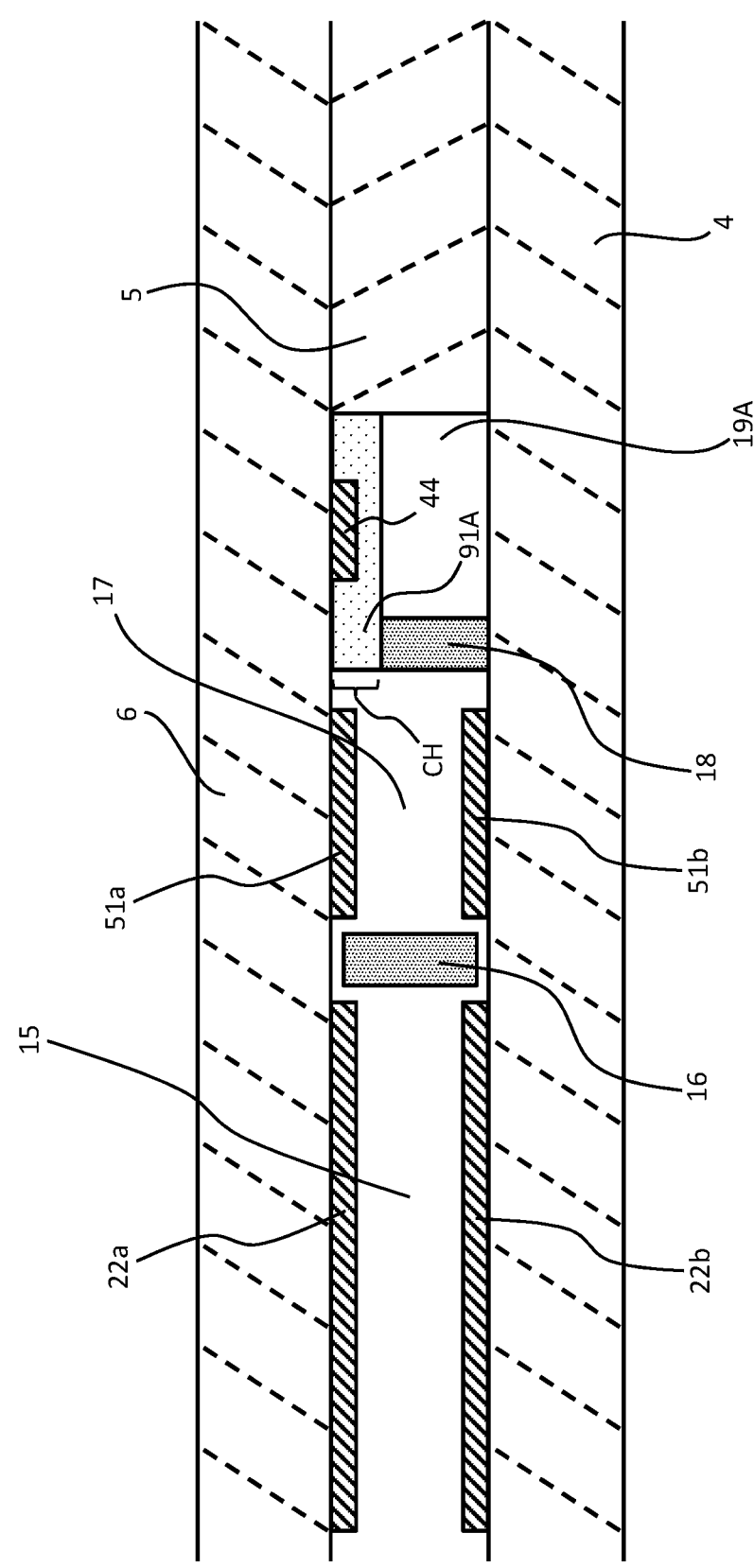
FIG. 5 is an illustrative enlarged view of key parts of an element substrate that includes a porous diffusion layer according to a variation.
Figure 7:
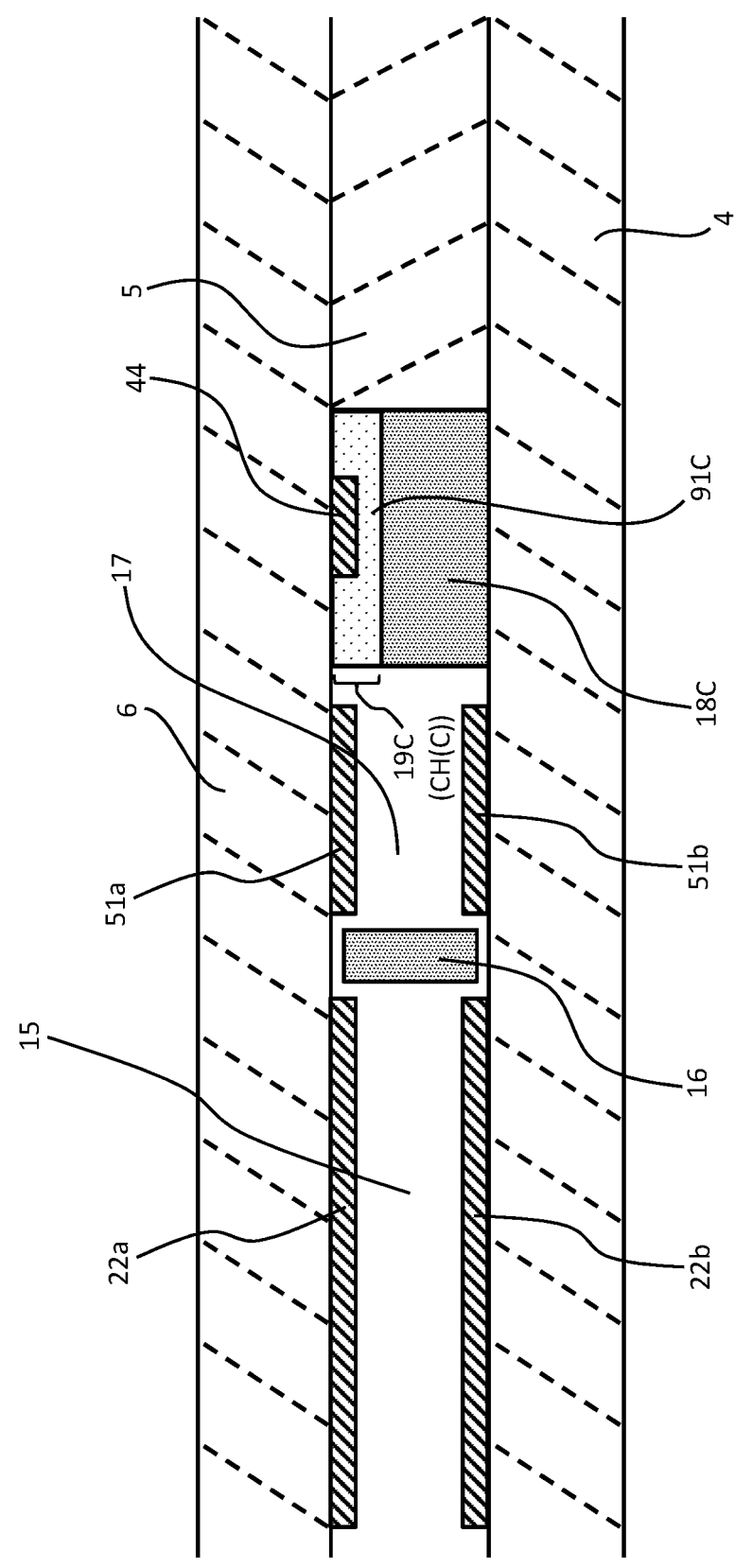
FIG. 7 is an illustrative enlarged view of key parts of an element substrate that includes a porous diffusion layer and a diffusion control portion according to a variation.
Figure 10:
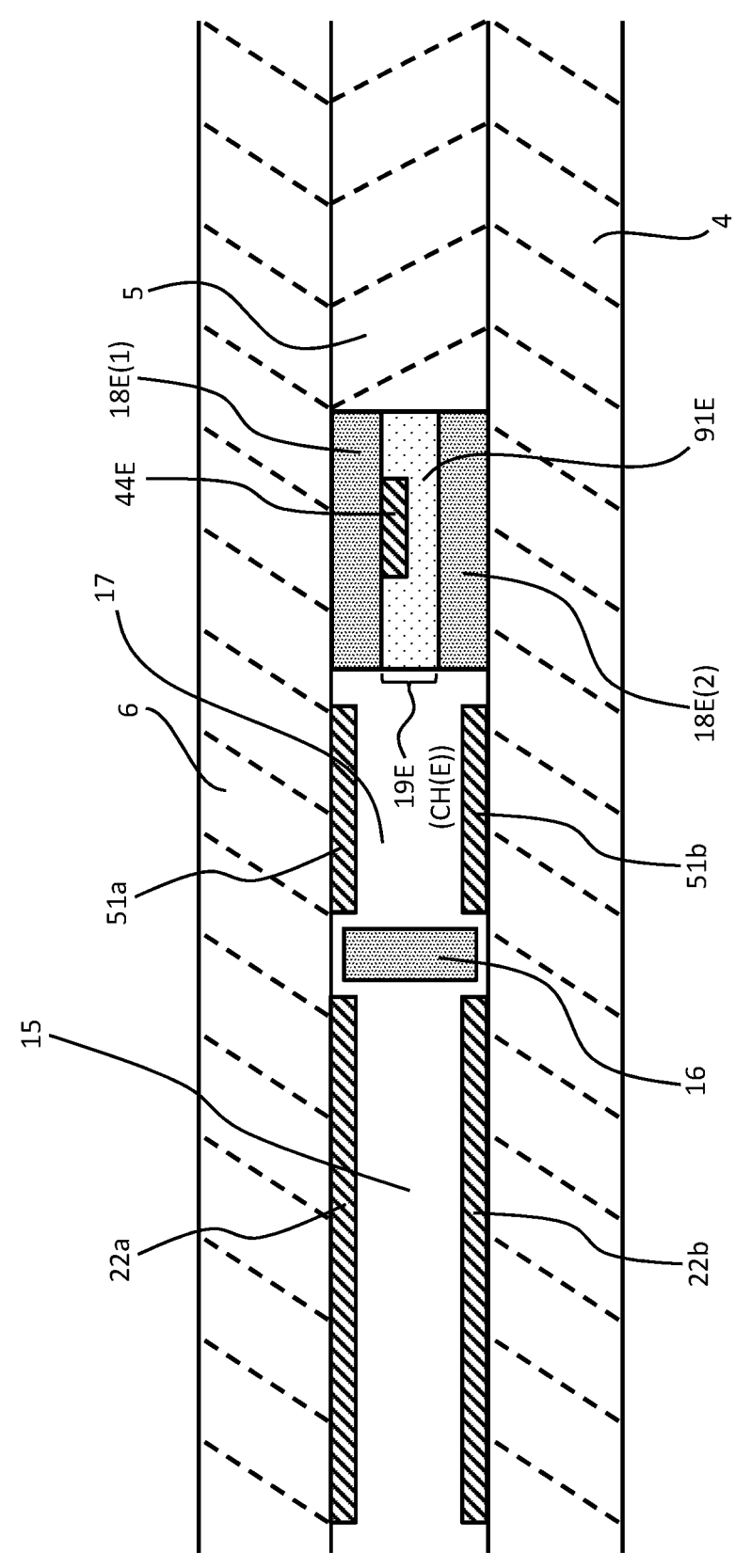
FIG. 10 is an illustrative enlarged view of key parts of an element substrate that includes the same flow path as that illustrated in FIG. 8 and a porous diffusion layer different from that illustrated in FIG. 8.

The measurement electrode 44 is a porous cermet electrode, and may contain at least either silica (SiO$_2$) or alumina (Al$_2$O$_3$). For example, the measurement electrode 44 contains 80 to 90% by weight of Pt, 9.5 to 19.8% by weight of a constituent material of the first solid electrolyte layer 4 (e.g. ZrO$_2$), and 0.2 to 0.5% by weight of a mixture containing at least either silica or alumina. The measurement electrode 44 has a higher content ratio of precious metal than that of the constituent material of the first solid electrolyte layer 4. This strengthens the adhesion between the first solid electrolyte layer 4 and the measurement electrode 44. Moreover, the measurement electrode 44 of this embodiment contains 0.2 to 0.5% by weight of a mixture containing at least either silica or alumina. Here, if NO$_x$ is measured at a high temperature (e.g. 700 to 800 degrees Celsius), the measurement electrode 44 will expand and contract constantly and repeatedly. Even in such an environment, the following effects can be achieved as a result of the measurement electrode 44 containing at least either silica or alumina. This means that the expansion and contraction at the measurement electrode 44 is suppressed, and the phenomenon in which the measurement electrode 44 peels away from the first solid electrolyte layer 4 does not occur. In addition, in the case where the measurement electrode 44 and the porous diffusion layer 91 are in contact with each other, particularly where the porous diffusion layer 91 covers the measurement electrode 44 as illustrated in FIGS. 5, 7 and 10, which will be described later, the following effects can be achieved as a result of the measurement electrode 44 containing at least either silica or alumina. This means that the expansion and contraction at the measurement electrode 44 is suppressed, thereby preventing cracks, splitting, or the like in the porous diffusion layer 91 that is in contact with the measurement electrode 44. Particularly, in the case where the porous diffusion layer 91 is in contact with the measurement electrode 44 and covers the measurement electrode 44, the effect of preventing cracks, splitting, or the like in the porous diffusion layer 91 that is in contact with the measurement electrode 44 is useful. Note that it is not essential for the measurement electrode 44 and the porous diffusion layer 91 to be in contact with each other in the gas sensor element 101. In the gas sensor element 101, the porous diffusion layer 91 need only be located at a position that is upstream of the measurement electrode 44 and where the distance d2 to the measurement electrode 44 is 0.15 mm or less, and need only block the predetermined region of the flow path CH of the measurement target gas.

The measurement electrode 44 also functions as a NO$_x$ reduction catalyst that reduces NO$_x$ present in the atmosphere in the third internal cavity 19. In one example in FIG. 2, the measurement electrode 44 is exposed within the third internal cavity 19. In another example, the measurement electrode 44 may be covered by a diffusion control portion or a porous diffusion layer (e.g. any of the porous diffusion layers 91A, 91C, and 91E illustrated in FIGS. 5, 7 and 10). This diffusion control portion may be constituted by a porous film mainly made of alumina (Al$_2$O$_3$). The diffusion control portion or the porous diffusion layer that coats (covers) the measurement electrode 44 serves to limit the amount of NO$_x$ flowing into the measurement electrode 44, and also acts as a protective film for the measurement electrode 44.

The element substrate 100 is configured such that the measurement pump cell 41 can pump out oxygen generated through decomposition of nitrogen oxide in the atmosphere around the measurement electrode 44, and can detect the amount of generated oxygen as a pump current Ip2.

Furthermore, in order to detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute an oxygen partial pressure detection sensor cell 82 for measurement pump control (i.e., an electro-chemical sensor cell). A variable power source 46 is controlled based on a voltage (an electromotive force) V2 detected by the oxygen partial pressure detection sensor cell 82 for measurement pump control.

The measurement target gas guided into the third internal cavity 19 reaches the measurement electrode 44 in a state in which the oxygen partial pressure has been controlled. Nitrogen oxide in the measurement target gas around the measurement electrode 44 is reduced to generate oxygen (2NO→N$_2$+O$_2$). The generated oxygen is pumped by the measurement pump cell 41, and, at that time, a voltage Vp2 of the variable power source is controlled such that the control voltage V2 detected by the oxygen partial pressure detection sensor cell 82 for measurement pump control is kept constant. The amount of oxygen generated around the measurement electrode 44 is proportional to the concentration of nitrogen oxide in the measurement target gas, and thus, it is possible to calculate the concentration of nitrogen oxide in the measurement target gas using the pump current Ip2 in the measurement pump cell 41.

Furthermore, if the measurement electrode 44, the first solid electrolyte layer 4, the third substrate layer 3, and the reference electrode 42 are combined to constitute an oxygen partial pressure detection means as an electro-chemical sensor cell, it becomes possible to detect an electromotive force that corresponds to a difference between the amount of oxygen generated through reduction of a NO$_x$ component in the atmosphere around the measurement electrode 44 and the amount of oxygen contained in reference air. This enables the measurement of the concentration of the nitrogen oxide component in the measurement target gas.

Furthermore, the second solid electrolyte layer 6, the spacer layer 5, the first solid electrolyte layer 4, the third substrate layer 3, the external pump electrode 23, and the reference electrode 42 constitute an electro-chemical sensor cell 83. The element substrate 100 is configured to be capable of detecting the oxygen partial pressure in the measurement target gas outside the sensor, based on an electromotive force Vref obtained by the sensor cell 83.

In the element substrate 100 having the above-described configuration, when the main pump cell 21 and the auxiliary pump cell 50 operate, the measurement target gas whose oxygen partial pressure is always kept at a constant low value (a value that substantially does not affect the $NO_x$ measurement) can be supplied to the measurement pump cell 41. Accordingly, the element substrate 100 is configured to be capable of identifying the nitrogen oxide concentration in the measurement target gas, based on the pump current Ip2 that flows when oxygen generated through reduction of $NO_x$ is pumped out by the measurement pump cell 41, substantially in proportion to the nitrogen oxide concentration in the measurement target gas.

Furthermore, the element substrate 100 includes a heater 70, which serves to adjust temperature to heat the element substrate 100 and keep the temperature thereof in order to increase oxygen ion conductivity of the solid electrolyte. In one example in FIG. 2, the heater 70 includes a heater electrode 71, a heat generating unit 72, a lead portion 73, a heater insulating layer 74, and a pressure dispersing hole 75. The lead portion 73 may be constituted by a through-hole.

The heater 70 of the present embodiment is disposed closer to the lower face of the element substrate 100 than to the upper face of the element substrate 100, in the thickness direction (vertical direction/stacking direction) of the element substrate 100. Note that the location of the heater 70 need not be limited to this example, and may be selected as appropriate, according to the mode of implementation.

The heater electrode 71 is an electrode in contact with the lower face of the first substrate layer 1 (the lower face of the element substrate 100). Electricity can be supplied from the outside to the heater 70 by connecting the heater electrode 71 to an external power source.

The heat generating unit 72 is an electrical resistor formed in a manner held between the second substrate layer 2 and the third substrate layer 3 from above and below. The heat generating unit 72 is connected via the lead portion 73 to the heater electrode 71. When electricity is supplied from the outside via the heater electrode 71, the heat generating unit 72 generates heat, thereby heating the solid electrolyte constituting the element substrate 100 and keeping the temperature thereof.

The heat generating unit 72 is buried across the entire region of the first internal cavity 15 to the second internal cavity 17, and enables the entire element substrate 100 to be adjusted at a temperature at which the aforementioned solid electrolyte is activated.

The heater insulating layer 74 is an insulating layer formed using insulators that are made of alumina or the like, on the upper and lower faces of the heat generating unit 72. The heater insulating layer 74 is formed for the purpose of providing electrical insulation between the second substrate layer 2 and the heat generating unit 72, and electrical insulation between the third substrate layer 3 and the heat generating unit 72.

The pressure dispersing hole 75 is a portion that extends through the third substrate layer 3 and is connected to the reference gas introduction space 43, and is formed for the purpose of mitigating the increase in internal pressure caused by a temperature rise in the heater insulating layer 74.

Porous Diffusion Layer

Figure 3:
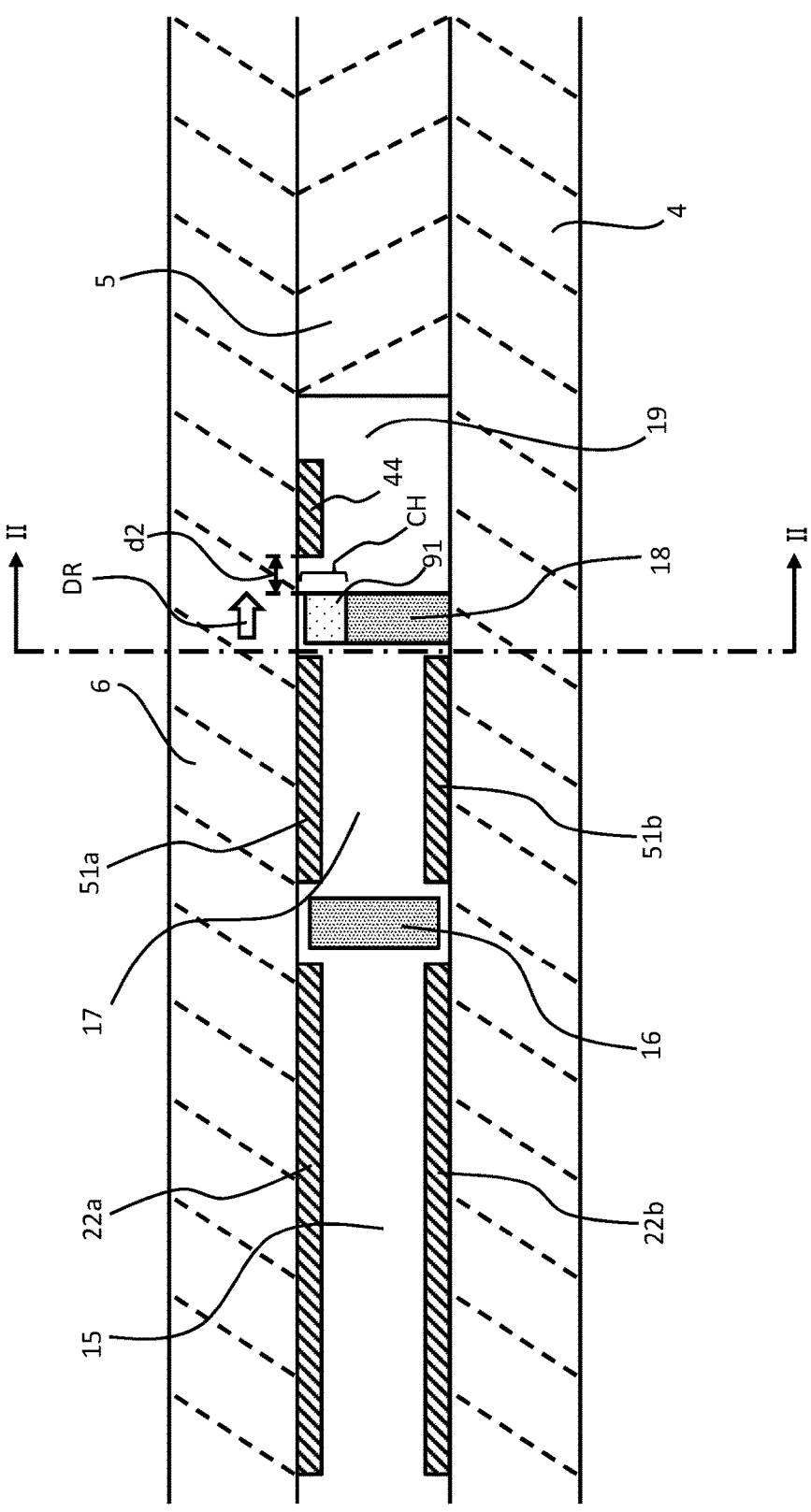
FIG. 3 is an illustrative enlarged view of key parts of the element substrate in FIG. 2.

FIG. 3 is an illustrative enlarged view of key parts of the element substrate 100. Specifically, FIG. 3 shows the details of the porous diffusion layer 91 that is disposed on the flow path CH formed (defined) by the fourth diffusion control portion 18. The porous diffusion layer 91 is a porous layer (porous body) having a porosity that is 5% or more and 25% or less and is lower than the porosity of the leading end protection layer 200. The porous diffusion layer 91 is located at a position that is upstream of the measurement electrode 44 in the flow direction DR of the measurement target gas (from the left side to the right side of the sheet in the example shown in FIG. 3) on the flow path CH and where the distance d2 to the measurement electrode 44 is 0.15 mm or less. In the example shown in FIG. 3, the porous diffusion layer 91 is provided on the flow path CH formed between the upper face of the fourth diffusion control portion 18 and the lower face of the second solid electrolyte layer 6, so as to be in contact with the upper face of the fourth diffusion control portion 18, at a position where the distance d2 to the measurement electrode 44 is 0.15 mm or less. For example, the porous diffusion layer 91 is located upstream of the measurement electrode 44 on the flow path CH such that the distance d2 from the side face thereof closest to the measurement electrode 44 (the face facing (opposing) the measurement electrode 44) to the measurement electrode 44 is 0.15 mm or less. In the example shown in FIG. 3, the porous diffusion layer 91 is located upstream of the measurement electrode 44 on the flow path CH such that the distance d2 from the face of the porous diffusion layer 91 on the downstream side in the flow direction DR of the measurement target gas (the face facing the measurement electrode 44) to the measurement electrode 44 is 0.15 mm or less.

The area of the face of the porous diffusion layer 91 that is orthogonal to the flow direction DR of the measurement target gas accounts for 70% or more of the area of the cross-section of the flow path CH that is orthogonal to the flow direction DR of the measurement target gas, as will be described in more detail later with reference to FIG. 4. The porous diffusion layer 91 can make the diffusion mode around the measurement electrode 44 a mode of diffusing while repeatedly colliding with a wall face of a sufficiently narrow flow path, as in Knudsen diffusion. This suppresses fluctuations in $NO_x$ output and the deterioration of the measurement electrode 44 under high $H_2O$ concentration that occur when the diffusion mode around the measurement electrode 44 is molecular diffusion.

The element substrate 100 illustrated in FIG. 3 includes an internal space (the measurement target gas flow portion 7) that is provided by hollowing out a portion of the spacer layer 5 between the first solid electrolyte layer 4 and the second solid electrolyte layer 6, as described with reference to FIG. 2. An upper portion (upper face) of the measurement target gas flow portion 7 is demarcated (defined) by the lower face of the second solid electrolyte layer 6, and a lower portion (lower face) is demarcated (defined) by the upper face of the first solid electrolyte layer 4. The measurement target gas flow portion 7 includes the first internal cavity 15, the second internal cavity 17, and the third internal cavity 19.

The first internal cavity 15 is a space for adjusting the oxygen partial pressure in the measurement target gas by means of the main pump cell 21, which is constituted by the internal pump electrode 22 (the ceiling electrode portion 22a and the bottom electrode 22b), the external pump electrode 23 (not shown in FIG. 3), and the second solid electrolyte layer 6.

The third diffusion control portion 16 applies predetermined diffusion resistance to the measurement target gas, whose oxygen concentration (oxygen partial pressure) has been controlled by operation of the main pump cell 21 in the first internal cavity 15, and guides the measurement target gas to the second internal cavity 17. That is, the third diffusion control portion 16 forms a flow path of the measurement target gas from the first internal cavity 15 to the second internal cavity 17.

In the second internal cavity 17, the auxiliary pump cell 50 further adjusts the oxygen partial pressure in the measurement target gas. The auxiliary pump cell 50 is constituted by an auxiliary pump electrode 51 (the ceiling electrode portion 51a and the bottom electrode portion 51b), the external pump electrode 23 (not shown in FIG. 3), and the second solid electrolyte layer 6.

The fourth diffusion control portion 18 applies predetermined diffusion resistance to the measurement target gas whose oxygen concentration (oxygen partial pressure) has been controlled by operation of the auxiliary pump cell 50 in the second internal cavity 17, and guides the measurement target gas to the third internal cavity 19. The fourth diffusion control portion 18 forms the flow path CH of the measurement target gas from the second internal cavity 17 to the third internal cavity 19. In the example shown in FIG. 3, the flow path CH is formed as a slit (gap) between the fourth diffusion control portion 18 and the lower face of the second solid electrolyte layer 6.

The porous diffusion layer 91 having a porosity of 5% or more and 25% or less is disposed on the flow path CH. The porous diffusion layer 91 is located at a position that is upstream of the measurement electrode 44 in the flow direction DR of the measurement target gas (from the left side to the right side of the sheet in the example shown in FIG. 3) and where the distance d2 to the measurement electrode 44 is 0.15 mm or less. The porous diffusion layer 91 located at this position blocks a predetermined region (specifically, 70% or more) of the flow path CH.

The measurement target gas whose oxygen partial pressure has been adjusted by the auxiliary pump cell 50 in the second internal cavity 17 is subjected to measurement of the nitrogen oxide concentration by the measurement pump cell 41 in the third internal cavity 19. The measurement pump cell 41 is constituted by the measurement electrode 44, the second solid electrolyte layer 6, the spacer layer 5, the first solid electrolyte layer 4, and the external pump electrode 23 (not shown in FIG. 3).

The porous diffusion layer 91 that has a porosity of 5% or more and 25% or less and blocks the predetermined region of the flow path CH of the measurement target gas is disposed around the measurement electrode 44, specifically, at a position that is upstream of the measurement electrode 44 and where the distance d2 to the measurement electrode 44 is 0.15 mm or less. The porous diffusion layer 91 can make the diffusion mode of the measurement target gas (particularly, $NO_x$ gas) around the measurement electrode 44 a mode of diffusing while repeatedly colliding with a wall face of a sufficiently narrow flow path, as in Knudsen diffusion. That is, the gas sensor element 101 makes the diffusion mode of the measurement target gas moving toward the measurement electrode 44 a favorable mode, such as Knudsen diffusion, by means of the porous diffusion layer 91 that blocks the predetermined region (specifically, 70% or more) of the flow path CH of the measurement target gas moving toward the measurement electrode 44.

Here, if the porous diffusion layer 91 having large diffusion resistance is provided around the measurement electrode 44, it is possible that the porous diffusion layer 91 will be clogged with poisonous substances or the like. To prevent this, the gas sensor element 101 has the leading end protection layer 200 that covers at least the face of the element substrate 100 in which the gas inlet is open, as illustrated in FIG. 1. Further, the porosity of the porous diffusion layer 91 is lower than the porosity of the leading end protection layer 200, i.e. the porosity of the leading end protection layer 200 is higher than the porosity of the porous diffusion layer 91.

Adopting this configuration enables poisonous substances or the like that cause clogging in the porous diffusion layer 91 to be captured in advance by the leading end protection layer 200. Thus, the amount of poisonous substances or the like in the measurement target gas that reaches the porous diffusion layer 91 and the measurement electrode 44 is negligible. This can reduce the likelihood of the porous diffusion layer 91 being clogged with poisonous substances or the like. Even if a poisonous substance or the like reaches the measurement electrode 44 and adheres to the measurement electrode 44, the poisonous substance will hardly affect the oxidation/reduction capacity of the electrode metal.

Thus, the gas sensor element 101 according to the present embodiment can prevent clogging in the porous diffusion layer 91 caused by poisonous substances or the like, and can also reduce the impact of poisonous substances or the like on the oxidation/reduction capacity of the measurement electrode 44. Specifically, a decrease in the measurement accuracy of the gas sensor element 101 resulting from use is favorably prevented, i.e. the measurement accuracy thereof is kept stable even after repeated use.

Figure 4:
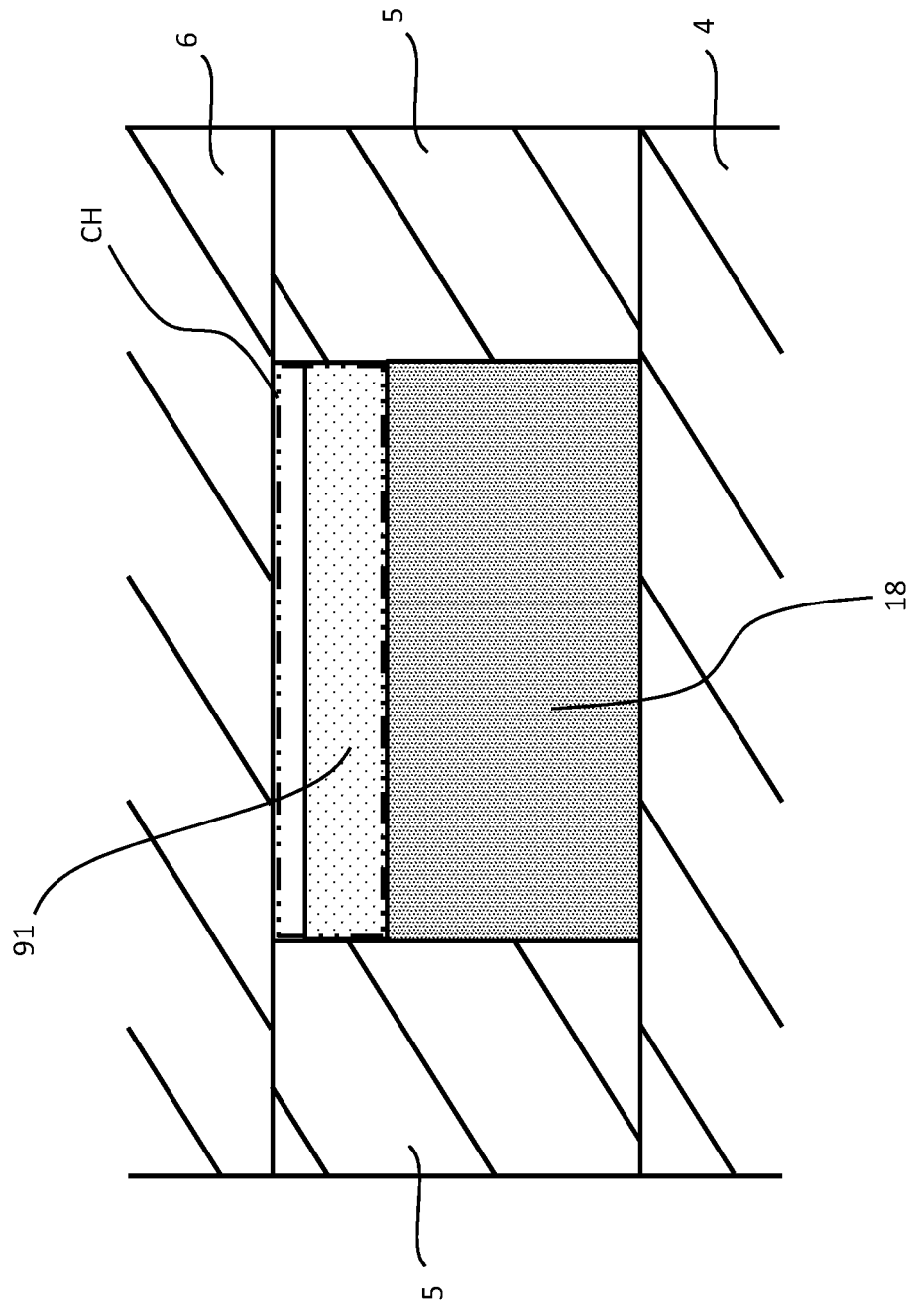
FIG. 4 shows an example of a cross-section of the element substrate in FIG. 3 taken along a line defined by arrows II-II.

FIG. 4 shows an example of a cross-section of the element substrate 100 in FIG. 3 taken along a line defined by arrows II-II. The area of the face of the porous diffusion layer 91 that is orthogonal to the flow direction DR of the measurement target gas (from the proximal side to the distal side of the sheet in the example shown in FIG. 4) accounts for 70% or more of the area of the cross-section of the flow path CH that is orthogonal to the flow direction DR of the measurement target gas. In the example shown in FIG. 4, the flow path CH of the measurement target gas from the second internal cavity 17 to the third internal cavity 19 is formed (defined) by the fourth diffusion control portion 18. Specifically, the flow path CH is formed as a slit (gap) between the fourth diffusion control portion 18 and the second solid electrolyte layer 6. That is, the lower face of the second solid electrolyte layer 6 demarcates (defines) the upper face of the flow path CH, which is illustrated by chain double-dashed lines in FIG. 4, the upper face of the fourth diffusion control portion 18 demarcates (defines) the lower face of the flow path CH, and the side faces of the spacer layer 5 demarcate (define) the two side faces of the flow path CH. The area of the face of the porous diffusion layer 91 that is orthogonal to the flow direction DR of the measurement target gas accounts for 70% or more of the area of the cross-section of the flow path CH that is orthogonal to the flow direction DR of the measurement target gas. That is, the porous diffusion layer 91, which is in contact with the upper face of the fourth diffusion control portion 18, accounts for (blocks) 70% or more of the area of the cross-section of the flow path CH that is orthogonal to the flow direction DR of the measurement target gas.

In the example shown in FIG. 4, a space (gap) is present between the upper face of the porous diffusion layer 91 and the lower face of the second solid electrolyte layer 6. In other words, in the example shown in FIG. 4, the proportion of the area of the face of the porous diffusion layer 91 that is orthogonal to the flow direction DR of the measurement target gas to the area of the cross-section of the flow path CH that is orthogonal to the flow direction DR of the measurement target gas is not 100%. Note that the proportion of the area of the face of the porous diffusion layer 91 that is orthogonal to the flow direction DR of the measurement target gas to the area of the cross-section of the flow path CH that is orthogonal to the flow direction DR of the measurement target gas need only be 70% or more, and may be 100%. In other words, the face of the porous diffusion layer 91 that is orthogonal to the flow direction DR of the measurement target gas may occupy an entire cross-section of the flow path CH that is orthogonal to the flow direction DR of the measurement target gas. In the example shown in FIG. 4, the porous diffusion layer 91 and the second solid electrolyte layer 6 may be in contact with each other; specifically, the upper face of the porous diffusion layer 91 and the lower face of the second solid electrolyte layer 6 may be in contact with each other.

The porous diffusion layer 91 illustrated in FIGS. 3 and 4 has a constant porosity throughout; specifically, the porosity of the porous diffusion layer 91 is 5% or more and 25% or less and is lower than the porosity of the leading end protection layer 200. However, it is not essential for the gas sensor element 101 (the element substrate 100) that the entire porous diffusion layer, which is located at a position that is upstream of the measurement electrode 44 and where the distance d2 to the measurement electrode 44 is 0.15 mm or more, has a constant porosity throughout.

In the gas sensor element 101, the porous diffusion layer, which is located at a position that is upstream of the measurement electrode 44 and where the distance d2 to the measurement electrode 44 is 0.15 mm or less, may include a plurality of faces (layers) with different porosities. In this case, it is desirable that the porosity of a face opposing (facing) the measurement electrode 44, of two faces of the porous diffusion layer that face opposite sides, is higher, specifically, 10% or more higher than the porosity of a face not opposing (not facing) the measurement electrode 44. For example, in the example shown in FIG. 3, the porosity of the face facing the downstream side and opposing the measurement electrode 44, of the two faces of the porous diffusion layer 91 that face opposite sides, may be higher than the porosity of the face facing the upstream side and opposing (facing) the second internal cavity 17. Particularly, the porosity of the face opposing (facing) the measurement electrode 44, of the two faces of the porous diffusion layer 91 that face opposite sides, may be 10% or more higher than the porosity of the face not opposing the measurement electrode 44. The gas sensor element 101 can achieve the following effects as a result of the porosity of the face opposing the measurement electrode 44, of the two faces of the porous diffusion layer that face opposite sides, being higher than the porosity of the face not opposing the measurement electrode 44. That is, the gas sensor element 101 can reduce the impact in the case where $H_2O$ on the surface of the measurement electrode 44 decomposes to generate $H_2$, and thus, the light-off time can be shortened that is required from when the gas sensor starts until when it enters a steady operation state. Particularly, the light-off time of the gas sensor element 101 can be further shortened as a result of the porosity of the face opposing the measurement electrode 44 being 10% higher than the porosity of the face not opposing the measurement electrode 44.

In the case where the porosity of the face opposing (facing) the measurement electrode 44, of the two faces of the porous diffusion layer that face opposite sides, is higher than the porosity of the face not opposing the measurement electrode 44, the porous diffusion layer satisfies the following conditions. That is, the porous diffusion layer has an average porosity that is 5% or more and 25% or less and is lower than the porosity of the leading end protection layer 200. The details of the porous diffusion layer that includes a plurality of faces (layers) with different porosities will be described later with reference to FIG. 5 and other figures.

Need for Contact Between Porous Diffusion Layer and Measurement Electrode

To make the diffusion mode around the measurement electrode 44 favorable, the porous diffusion layer 91 is located at a position that is upstream of the measurement electrode 44 and where the distance d2 to the measurement electrode 44 is 0.15 mm or less, and blocks the predetermined region (specifically, 70% or more) of the flow path CH. The porous diffusion layer 91 may be in contact with the measurement electrode 44, or may alternatively be located upstream of the measurement electrode 44 without being in contact with the measurement electrode 44 such that the distance d2 to the measurement electrode 44 is 0.15 mm or less. That is, the porous diffusion layer 91 illustrated in FIGS. 2 and 3 is located upstream of the measurement electrode 44 such that the distance d2 to the measurement electrode 44 is 0.15 mm or less, without being in contact with the measurement electrode 44. However, the porous diffusion layer 91 located at a position that is upstream of the measurement electrode 44 and where the distance d2 to the measurement electrode 44 is 0.15 mm or less may alternatively be in contact with the measurement electrode 44. An example of the porous diffusion layer 91 that is in contact with the measurement electrode 44 will be described below with reference to FIG. 5.

Example where Porous Diffusion Layer and Measurement Electrode are in Contact with Each Other FIG. 5 is an illustrative enlarged view of key parts of the element substrate 100 (the gas sensor element 101) that includes a porous diffusion layer 91A according to a variation. Specifically, FIG. 5 shows an example of the porous diffusion layer 91A, which is located at a position that is upstream of the measurement electrode 44 in the flow direction DR of the measurement target gas (from the left side to the right side of the sheet in the example shown in FIG. 5), blocks the predetermined region of the flow path CH, and is in contact with the measurement electrode 44. The gas sensor element 101 may include the porous diffusion layer 91A, which will be described in more detail below, instead of the porous diffusion layer 91. Note that the first solid electrolyte layer 4, the spacer layer 5, the second solid electrolyte layer 6, and other members in FIG. 5 are the same as those described with reference to FIGS. 2 and 3 and others figures, and the description thereof is not repeated.

The porous diffusion layer 91 illustrated in FIGS. 2 and 3 is located upstream of the measurement electrode 44 on the flow path CH such that the distance d2 to the measurement electrode 44 is 0.15 mm or less, without being in contact with the measurement electrode 44. However, it is not essential for the gas sensor element 101 that a space (gap) is present between the measurement electrode 44 and the porous diffusion layer that is located at a position that is upstream of the measurement electrode 44 and where the distance d2 to the measurement electrode 44 is 0.15 mm or less and that blocks the predetermined region on the flow path CH. In the gas sensor element 101, the porous diffusion layer that is located at a position that is upstream of the measurement electrode 44 and where the distance d2 to the measurement electrode 44 is 0.15 mm or less and that blocks the predetermined region of the flow path CH may be in contact with the measurement electrode 44, as the porous diffusion layer 91A illustrated in FIG. 5 is.

The porous diffusion layer 91A illustrated in FIG. 5 is the same as the porous diffusion layer 91 illustrated in FIGS. 2 and 3 in that it is located upstream of the measurement electrode 44. Meanwhile, the porous diffusion layer 91A disposed upstream of the measurement electrode 44 extends downstream, specifically, extends toward the measurement electrode 44 and is in contact with the measurement electrode 44. Particularly, the porous diffusion layer 91A illustrated in FIG. 5 extends downstream of the measurement electrode 44 and covers the measurement electrode 44.

Here, the porous diffusion layer 91A that is in contact with the measurement electrode 44 covers the measurement electrode 44 in the example shown in FIG. 5. However, it is not essential for the gas sensor element 101 that the porous diffusion layer 91A in contact with the measurement electrode 44 covers the measurement electrode 44. In the gas sensor element 101, the porous diffusion layer 91A may alternatively be in contact with the measurement electrode 44 without covering the measurement electrode 44.

In the example shown in FIG. 5, the porous diffusion layer 91A that covers the measurement electrode 44 is in contact with the measurement electrode 44, i.e. the face of the porous diffusion layer 91A that opposes (faces) the measurement electrode 44 is in contact with the measurement electrode 44. However, the gas sensor element 101 may alternatively have a porous diffusion layer that surrounds the measurement electrode 44 without being in contact with the measurement electrode 44. In the gas sensor element 101, it is not essential for the porous diffusion layer that covers the measurement electrode 44 to be in contact with the measurement electrode 44, and the porous diffusion layer that covers the measurement electrode 44 need not be in contact with the measurement electrode 44. That is, the gas sensor element 101 may include a porous diffusion layer that covers the measurement electrode 44, and a space (gap) may be present between this porous diffusion layer and the measurement electrode 44. If a gap is present between the measurement electrode 44 and the porous diffusion layer covering the measurement electrode 44, the distance d2 from the face opposing the measurement electrode 44, of the porous diffusion layer covering the measurement electrode 44, to the measurement electrode 44 is 0.15 mm or less. That is, the porous diffusion layer that makes the diffusion mode around the measurement electrode 44 favorable in the gas sensor element 101 need only be located at a position that is upstream of the measurement electrode 44 and where the distance d2 to the measurement electrode 44 is 0.15 mm or less.

To summarize the above description, in the gas sensor element 101, the porous diffusion layer that is located upstream of the measurement electrode 44 and blocks the predetermined region (specifically, 70% or more) of the flow path CH may be in contact with the measurement electrode 44, as the porous diffusion layer 91A illustrated in FIG. 5 is. In the gas sensor element 101, the porous diffusion layer that is located upstream of the measurement electrode 44 and blocks the predetermined region of the flow path CH need only be located at a position where the distance d2 to the measurement electrode 44 is 0.15 mm or less, and may be, but need not necessarily be in contact with the measurement electrode 44. Further, the porous diffusion layer that is located upstream of the measurement electrode 44 and blocks the predetermined region of the flow path CH in the gas sensor element 101 may cover the measurement electrode 44, as the porous diffusion layer 91A does.

That is, in the gas sensor element 101, the porous diffusion layer having a porosity that is lower than the porosity of the leading end protection layer 200 and is 5% or more and 25% or less need only satisfy the following conditions. In other words, this porous diffusion layer need only be located at a position that is upstream of the measurement electrode 44 on the flow path CH of the measurement target gas and where the distance d2 to the measurement electrode 44 is 0.15 mm or less, and block the predetermined region (70% or more) of the flow path CH. In the gas sensor element 101, the porous diffusion layer may be, but need not necessarily be in contact with the measurement electrode 44. Further, in the gas sensor element 101, the porous diffusion layer may, but need not necessarily cover the measurement electrode 44. The face of the porous diffusion layer that opposes (faces) the measurement electrode 44 may be, but need not necessarily be in contact with the measurement electrode 44. However, if the face of the porous diffusion layer that opposes the measurement electrode 44 is not in contact with the measurement electrode 44, the distance d2 from the face of the porous diffusion layer that opposes the measurement electrode 44 to the measurement electrode 44 is 0.15 mm or less.

The porous diffusion layer 91A illustrated in FIG. 5 is in contact with the fourth diffusion control portion 18 (diffusion control portion) and a face defining the measurement target gas flow portion 7 (internal space) (the second solid electrolyte layer 6; particularly, the lower face of the second solid electrolyte layer 6 in the example shown in FIG. 5). That is, no space (gap) is present between the porous diffusion layer 91A and the fourth diffusion control portion 18, and between the porous diffusion layer 91A and the face defining the measurement target gas flow portion 7. The gas sensor element 101 can achieve the following effects as a result of gaps being eliminated between the porous diffusion layer 91A and the fourth diffusion control portion 18 and between the porous diffusion layer 91A and the face defining the measurement target gas flow portion 7. That is, the gas sensor element 101 can prevent the measurement target gas from reaching the measurement electrode 44 from at least either a gap between the porous diffusion layer 91A and the fourth diffusion control portion 18 or a gap between the porous diffusion layer 91A and the face defining the measurement target gas flow portion 7. This means that the gas sensor element 101 can reduce the likelihood of a situation where, for example, the measurement target gas leaks out from an intermediate portion of the flow path CH and reaches the measurement electrode 44 without the diffusion mode being changed by the porous diffusion layer 91A. Thus, the gas sensor element 101 can bring the diffusion mode of the measurement target gas moving toward the measurement electrode 44 closer to a favorable diffusion mode, such as Knudsen diffusion, by means of the porous diffusion layer 91A that blocks the predetermined region of the flow path CH through which the measurement target gas is guided.

Note that the porous diffusion layer 91A illustrated in FIG. 5 has a porosity that is lower than the porosity of the leading end protection layer 200 and is 5% or more and 25% or less, as the porous diffusion layer 91 illustrated in FIGS. 2 and 3 does. Further, the porous diffusion layer 91A is located at a position that is upstream of the measurement electrode 44 in the flow direction DR of the measurement target gas and where the distance to the measurement electrode 44 is 0.15 mm or less, and blocks 70% or more of the flow path CH of the measurement target gas moving toward the measurement electrode 44. Particularly, the porous diffusion layer 91A illustrated in FIG. 5 accounts for the entirety (i.e. 100%) of the flow path CH formed by the fourth diffusion control portion 18 (specifically, the flow path CH formed as a slit (gap) between the fourth diffusion control portion 18 and the second solid electrolyte layer 6). That is, the face of the porous diffusion layer 91A that is orthogonal to the flow direction DR of the measurement target gas accounts for 70% or more of the area of the cross-section of the flow path CH that is orthogonal to the flow direction DR of the measurement target gas.

The porous diffusion layer 91A illustrated in FIG. 5 has a constant porosity of 5% or more and 25% or less throughout. However, it is not essential for the gas sensor element 101 (the element substrate 100) that the porous diffusion layer, which is located at a position that is upstream of the measurement electrode 44 and where the distance d2 to the measurement electrode 44 is 0.15 mm or less, has a porosity that is constant throughout the entire porous diffusion layer. In the gas sensor element 101, the porous diffusion layer located at a position that is upstream of the measurement electrode 44 and where the distance d2 to the measurement electrode 44 is 0.15 mm or less may alternatively be configured as follows. That is, the porous diffusion layer may be configured such that the porosity is different between two faces of the porous diffusion layer that face opposite sides, one of the two faces being a face opposing (facing) the measurement electrode 44 and the other being a face not opposing (not facing) the measurement electrode 44.

Specifically, the porosity of the face opposing (in contact with) the measurement electrode 44, of the two faces of the porous diffusion layer 91A that face opposite sides, may be higher than the porosity of the face not facing (not in contact with) the measurement electrode 44. For example, the porous diffusion layer 91A may have two faces facing opposite sides that are configured as follows. That is, the porous diffusion layer 91A may have a face not opposing the measurement electrode 44 but facing the measurement target gas flow portion 7 that is constituted by a first porous diffusion layer, which is a porous layer, and may have a face opposing the measurement electrode 44 that is constituted by a second porous diffusion layer, which is a porous layer. The first porous diffusion layer and the second porous diffusion layer may have different porosities, and the porosity of the second porous diffusion layer may be higher than the porosity of the first porous diffusion layer.

The following effects can be achieved as a result of the porosity of the face opposing (in contact with) the measurement electrode 44, of the two faces of the porous diffusion layer 91A that face opposite sides, being higher than the porosity of the face not opposing (not in contact with) the measurement electrode 44. That is, it is possible to reduce the impact in the case where $H_2O$ on the surface of the measurement electrode 44 decomposes to generate $H_2$, and shorten the light-off time required from when the gas sensor starts until when the gas sensor enters the steady operation state. This is for the following reasons.

If $H_2O$ on the surface of the measurement electrode 44 decomposes to generate $H_2$ immediately after the gas sensor is driven, the potential difference (i.e. oxygen concentration difference) between the measurement electrode 44 and the reference electrode 42 increases. Thus, pumping oxygen into the measurement electrode 44 may result in an undershoot waveform and a longer light-off time.

In contrast, the gas sensor element 101 achieves the following effects as a result of the porosity of the face opposing (in contact with) the measurement electrode 44 being higher than the porosity of the face not opposing (in contact with) the measurement electrode 44, for the porous diffusion layer that makes the diffusion mode around the measurement electrode 44 favorable. That is, the gas sensor element 101 can quickly diffuse $H_2$ generated in the vicinity of the surface of the measurement electrode 44 as a result of the porosity of the face opposing the measurement electrode 44 being higher than the porosity of the face not facing the measurement electrode 44. In other words, $H_2$ generated due to decomposition of $H_2O$ on the surface of the measurement electrode 44 can be quickly diffused by the face opposing (in contact with) the measurement electrode 44 that has a porosity larger than that of the face not opposing (not in contact with) the measurement electrode 44. Accordingly, in the gas sensor element 101, the potential difference between the measurement electrode 44 and the reference electrode 42 does not excessively increase during constant control, and the light-off time of the gas sensor element 101 can be shortened. In other words, even if $H_2O$ on the surface of the measurement electrode 44 decomposes to generate $H_2$, the gas sensor element 101 can reduce the impact of $H_2$ and prevent an increase in the light-off time.

Particularly, if no space is present between the porous diffusion layer 91A and the measurement electrode 44, i.e. if they are in contact with each other, it is desirable that the porous diffusion layer 91A is configured as follows. That is, it is desirable that the porous diffusion layer 91A is configured such that the porosity of the face in contact with the measurement electrode 44, of the two faces of the porous diffusion layer 91A that face opposite sides, is higher than the porosity of the face not in contact with the measurement electrode 44. Specifically, in the case where the porous diffusion layer 91A and the measurement electrode 44 are in contact with each other, it is desirable that the porosity of the face of the porous diffusion layer 91A that is in contact with the measurement electrode 44 is higher than the porosity of the face not in contact with the measurement electrode 44 (e.g. the face facing the measurement target gas flow portion 7). Even when the porous diffusion layer 91A and the measurement electrode 44 are in contact with each other, the porous diffusion layer 91A can achieve the following effects as a result of the porosity of the face of the porous diffusion layer 91A in contact with the measurement electrode 44 being higher than the porosity of the face not in contact with the measurement electrode 44. That is, the porous diffusion layer 91A can reduce the impact in the case where $H_2O$ on the surface of the measurement electrode 44 decomposes to generate $H_2$, and can shorten the light-off time.

Note that the porosity is a value derived, for example, by applying a known image processing method (e.g. binarization) to an image (SEM image) obtained by observation using a scanning electron microscope (SEM). Specifically, the porosity of the face of the porous diffusion layer 91A that opposes (is in contact with) the measurement electrode 44 was derived as follows, for example. That is, first, a SEM image was obtained in the vicinity of the center of the measurement electrode 44 when viewed in the lengthwise direction (the axial direction of the sensor element), in the range from 10 to 15 μm from the interface between the measurement electrode 44 and the porous diffusion layer 91A. Next, the porosity of the face of the porous diffusion layer 91A that opposes (is in contact with) the measurement electrode 44 was obtained by applying a known image processing method, such as binarization, to the obtained SEM image. The same approach was applied to obtain the porosity of the face of the porous diffusion layer 91A that does not oppose (is not in contact with) the measurement electrode 44. That is, first, a SEM image was obtained from the face (surface, e.g. the upper face) of the porous diffusion layer 91A that does not oppose (is not in contact with) the measurement electrode 44, in the range from 10 to 15 μm. Then, the porosity of the face of the porous diffusion layer 91A that does not oppose (is not in contact with) the measurement electrode 44 was derived by applying a known image processing method to the SEM image.

As mentioned above, the porosity of the face opposing (in contact with) the measurement electrode 44, of the two faces of the porous diffusion layer 91A that face opposite sides, may be higher than the porosity of the face not opposing (not in contact with) the measurement electrode 44. Particularly, the porosity of the face of the porous diffusion layer 91A that opposes (is in contact with) the measurement electrode 44 may be 10% higher than the porosity of the face not opposing (not in contact with) the measurement electrode 44.

Here, the inventors confirmed that the light-off time is shorter when the porosity of the face opposing (in contact with) the measurement electrode 44 is 10% or more higher than the porosity of the face not opposing (not in contact with) the measurement electrode 44, than when the former is less than 10% higher than the latter. Hence, in the porous diffusion layer 91A, it is desirable that the difference between the porosity of the face opposing (in contact with) the measurement electrode 44 and the porosity of the face not opposing (not in contact with) the measurement electrode 44 is 10% or more. Specifically, it is desirable that the porosity of the face opposing (in contact with) the measurement electrode 44, of the two faces of the porous diffusion layer 91A that face opposite sides, is 10% or more higher than the porosity of the face not opposing (not in contact with) the measurement electrode 44. The light-off time of the gas sensor element 101 can be shortened as a result of the porosity of the face of the porous diffusion layer 91A that opposes (is in contact with) the measurement electrode 44 being 10% or more higher than the porosity of the face not opposing (not in contact with) the measurement electrode 44, compared to when the former is less than 10% higher than the latter. For example, the light-off time of the gas sensor element 101 can be further shortened as a result of the porosity of the face of the porous diffusion layer 91A that opposes the measurement electrode 44 being 10% or more higher than the porosity of the face that does not oppose the measurement electrode 44 but faces the measurement target gas flow portion 7.

As described above, the face opposing (in contact with) the measurement electrode 44, of the two faces of the porous diffusion layer 91A that face opposite sides, may be higher than the porosity of the face not opposing (not in contact with) the measurement electrode 44, e.g. by 10% or more. Here, the mode of the change in porosity from the face of the porous diffusion layer 91A that opposes (is in contact with) the measurement electrode 44 toward the face not opposing (not in contact with) the measurement electrode 44 is not particularly limited.

The porosity of the porous diffusion layer 91A may change stepwise (discontinuously) from the face opposing (in contact with) the measurement electrode 44 toward the face not opposing (not in contact with) the measurement electrode 44 (e.g. the face facing the measurement target gas flow portion 7). Specifically, the porous diffusion layer 91A may have the following two faces with different porosities as the two faces facing opposite sides. That is, the porous diffusion layer 91A may include a first porous diffusion layer that is a porous layer that does not face the measurement electrode 44 but faces the measurement target gas flow portion 7, and a second porous diffusion layer that is a porous layer facing the measurement electrode 44. In this case, it is desirable that the porosity of the first porous diffusion layer is lower than the porosity of the second porous diffusion layer; specifically, it is desirable that the porosity of the first porous diffusion layer is 10% or more lower than the porosity of the second porous diffusion layer. That is, the porous diffusion layer 91A may include a plurality of layers with different porosities, and the porosity of the porous diffusion layer 91A may change stepwise (discontinuously) from the face opposing (in contact with) the measurement electrode 44 toward the face not opposing (not in contact with) the measurement electrode 44.

Alternatively, the porosity of the porous diffusion layer 91A may continuously vary from the face opposing (in contact with) the measurement electrode 44 toward the face not opposing (not in contact with) the measurement electrode 44 (e.g. the face facing the measurement target gas flow portion 7). That is, the porosity may continuously vary from the face opposing (in contact with) the measurement electrode 44 toward the face not facing (not in contact with) the measurement electrode 44, of the two faces of the porous diffusion layer 91A that face opposite sides. For example, the porous diffusion layer 91A may be configured such that the porosity gradually decreases from the face opposing the measurement electrode 44 toward the face not opposing the measurement electrode 44 (e.g. the face facing the measurement target gas flow portion 7), resulting in a difference in the porosity therebetween of 10% or more.

As described above, the porosity of the face opposing (in contact with) the measurement electrode 44, of the two faces of the porous diffusion layer 91A that face opposite sides, may be higher than the porosity of the face not opposing (not in contact with) the measurement electrode 44, particularly, by 10% or more. Further, there is no particular limitation on the mode of the change in porosity from the face opposing (in contact with) the measurement electrode 44 toward the face not opposing (not in contact with) the measurement electrode 44. For example, the change may be stepwise (discontinuous) or continuous.

If the porous diffusion layer that is located at a position that is upstream of the measurement electrode 44 and where the distance d2 to the measurement electrode 44 is 0.15 mm or less and that blocks the predetermined region of the flow path CH has a plurality of faces (layers) with different porosities, the average porosity of the porous diffusion layer satisfies the following conditions. That is, if the porous diffusion layer has a plurality of faces with different porosities, the average porosity of the porous diffusion layer is 5% or more and 25% or less, and is lower than the porosity of the leading end protection layer 200. For example, if the porosity differs between the face of the porous diffusion layer 91A that opposes (is in contact with) the measurement electrode 44 and the face thereof that does not oppose (is not in contact with) the measurement electrode 44, the average porosity of the porous diffusion layer 91A is 5% or more and 25% or less, and is lower than the porosity of the leading end protection layer 200. Specifically, the average porosity of the porous diffusion layer 91A that is calculated based on the porosities of the aforementioned first and second porous diffusion layers is 5% or more and 25% or less, and is lower than the porosity of the leading end protection layer 200. That is, if the porous diffusion layer 91A includes a plurality of faces (layers), particularly, a plurality of faces with different porosities, the average porosity of the porous diffusion layer 91A is 5% or more and 25% or less, and is lower than the porosity of the leading end protection layer 200.

Length of Porous Diffusion Layer and Diffusion Control Portion in Axial Direction The porous diffusion layer 91 illustrated in FIGS. 2 and 3 and the porous diffusion layer 91A illustrated in FIG. 5 both have a width (length in the axial direction of the gas sensor element 101) that is larger than or equal to the width (length in the axial direction of the gas sensor element 101) of the fourth diffusion control portion 18. That is, the width of the porous diffusion layer 91 is the same as the width of the fourth diffusion control portion 18, while the width of the porous diffusion layer 91A is larger than the width of the fourth diffusion control portion 18. However, it is not essential that the porous diffusion layer located at a position that is upstream of the measurement electrode 44 in the gas sensor element 101 (the element substrate 100) and where the distance d2 to the measurement electrode 44 is 0.15 mm or less has a width larger than or equal to the width of the fourth diffusion control portion 18. In the gas sensor element 101, the porous diffusion layer located at a position that is upstream of the measurement electrode 44 and where the distance d2 to the measurement electrode 44 is 0.15 mm or less may have a width smaller than the width of the fourth diffusion control portion 18. That is, in the gas sensor element 101, the diffusion control portion (e.g. the fourth diffusion control portion 18) that forms the flow path CH having a predetermined region blocked by the porous diffusion layer may have a width larger than the width of this porous diffusion layer. The following is a description of an example of the fourth diffusion control portion 18 having a width larger than the width of the porous diffusion layer for making the diffusion mode around the measurement electrode 44 favorable, with reference to FIG. 6.

Figure 6:
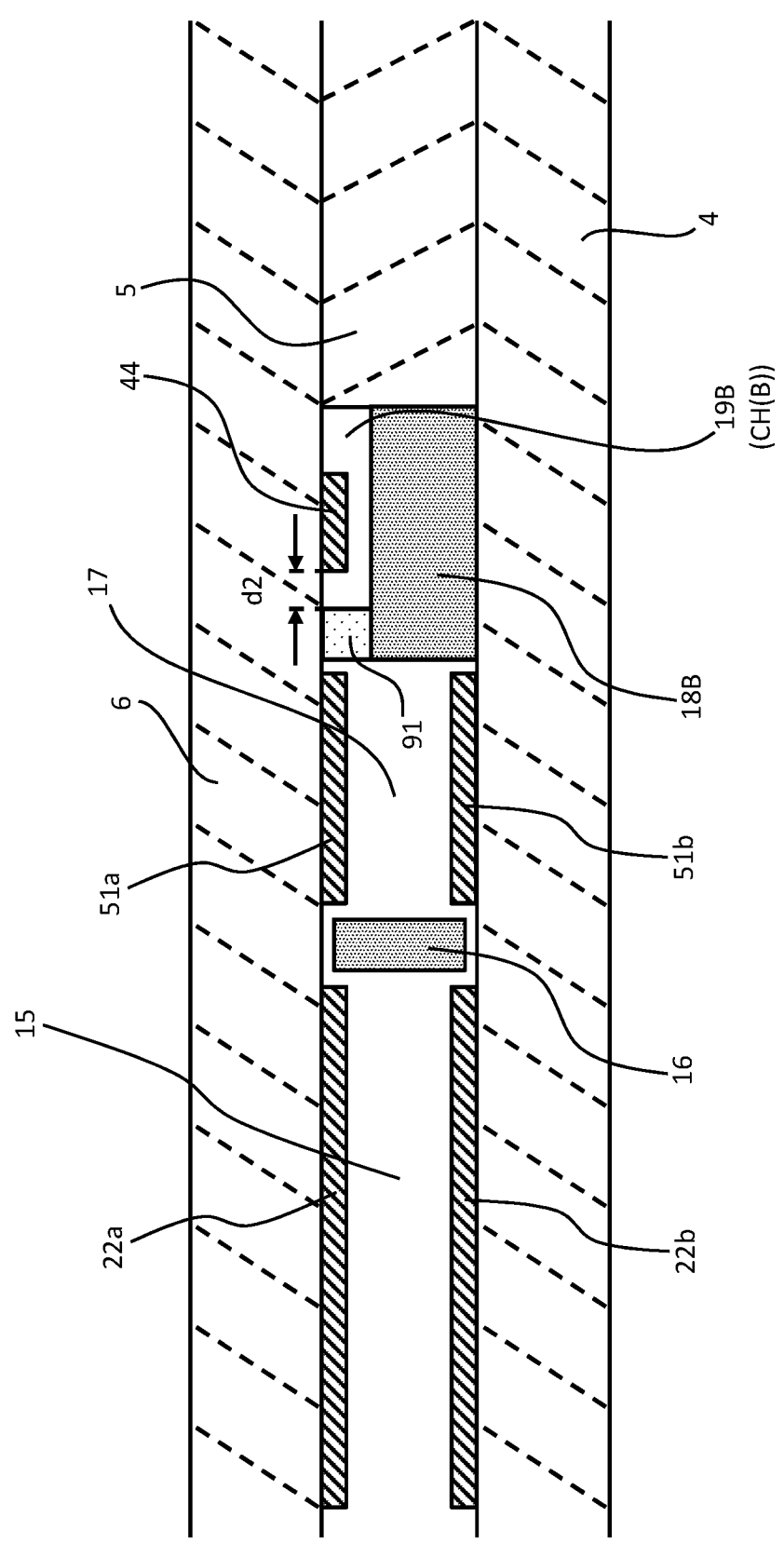
FIG. 6 is an illustrative enlarged view of key parts of an element substrate that includes a diffusion control portion according to a variation.

Example of Diffusion Control Portion Having Width Longer than that of Porous Diffusion Layer FIG. 6 is an illustrative enlarged view of key parts of the element substrate 100 (gas sensor element 101) that includes a fourth diffusion control portion 18B according to a variation. Specifically, FIG. 6 shows an example of the fourth diffusion control portion 18B that has a width (length in the axial direction in the gas sensor element 101) larger than the width of the fourth diffusion control portion 18 illustrated in FIGS. 2, 3, and 5. Note that the first solid electrolyte layer 4, the spacer layer 5, the second solid electrolyte layer 6, and other members in FIG. 6 are the same as those described with reference to FIGS. 2, 3 and other figures, and the description thereof is not repeated.

The basic configuration of the fourth diffusion control portion 18B is the same as that of the fourth diffusion control portion 18. That is, the fourth diffusion control portion 18B applies predetermined diffusion resistance to the measurement target gas in the measurement target gas flow portion 7 (internal space). The porosity of the fourth diffusion control portion 18B is lower than the porosity of the porous diffusion layer 91, i.e. the fourth diffusion control portion 18B is denser than the porous diffusion layer 91. Furthermore, the fourth diffusion control portion 18B is located upstream of the measurement electrode 44 in the flow direction DR of the measurement target gas.

Meanwhile, the fourth diffusion control portion 18B differs from the fourth diffusion control portion 18 on the following points. Specifically, the fourth diffusion control portion 18B located upstream of the measurement electrode 44 extends downstream, i.e. toward the measurement electrode 44, and particularly, up to a position downstream of the measurement electrode 44. In the example shown in FIG. 6, the fourth diffusion control portion 18B disposed upstream of the measurement electrode 44 extends downstream of the measurement electrode 44 and is in contact with the spacer layer 5. Thus, the width of the fourth diffusion control portion 18B (length in the axial direction of the gas sensor element 101) is larger than the width of the porous diffusion layer 91.

In the example shown in FIG. 6, a flow path CH(B), which is defined by the fourth diffusion control portion 18B and the second solid electrolyte layer 6, is integrated with a third internal cavity 19B, in which the measurement electrode 44 is disposed. That is, the fourth diffusion control portion 18B extends downstream, particularly, extends downstream of the measurement electrode 44 and is in contact with the spacer layer 5. The flow path CH(B) of the measurement target gas moving toward the measurement electrode 44 is defined by the fourth diffusion control portion 18B and the second solid electrolyte layer 6. Specifically, in the example shown in FIG. 6, the flow path CH(B) (i.e. the third internal cavity 19B) has an upper face defined (demarcated) by the second solid electrolyte layer 6, a lower face defined by the fourth diffusion control portion 18B, and side and rear faces defined by the spacer layer 5. Further, the entrance of the flow path CH(B) (i.e. the third internal cavity 19B) is blocked by the porous diffusion layer 91, which is separated from the measurement electrode 44 by the distance d2 that is 0.15 mm or less.

That is, the fourth diffusion control portion 18B defines (demarcates) at least one face of the flow path CH(B) of the measurement target gas moving toward the measurement electrode 44. In the example shown in FIG. 6, the fourth diffusion control portion 18B defines the lower face of the flow path CH(B). A predetermined region of the flow path CH(B) formed (defined) by the fourth diffusion control portion 18B is blocked by the porous diffusion layer 91 located at a position that is upstream of the measurement electrode 44 and where the distance d2 to the measurement electrode 44 is 0.15 mm or less.

The gas sensor element 101 may alternatively have a flow path CH(B) having a predetermined region (specifically, 70% or more) blocked by the porous diffusion layer 91, instead of the flow path CH described with reference to FIG. 2 and other figures. In the gas sensor element 101, the diffusion control portion that defines the flow path CH(B) may extend downstream, as the fourth diffusion control portion 18B does. Specifically, the diffusion control portion may extend downstream of the measurement electrode 44. In the example shown in FIG. 6, the fourth diffusion control portion 18B disposed upstream of the measurement electrode 44 extends downstream of the measurement electrode 44. Further, the porous diffusion layer 91 blocks the entrance of the flow path CH(B) (i.e. the third internal cavity 19B) defined by the fourth diffusion control portion 18B disposed upstream of the measurement electrode 44 and extending downstream of the measurement electrode 44, and the second solid electrolyte layer 6.

Like the flow path CH, the flow path CH(B) has at least one face defined (demarcated) by the fourth diffusion control portion 18B, as described above. In the example shown in FIG. 6, the lower face of the flow path CH(B) is defined by the fourth diffusion control portion 18B. The gas sensor element 101 can guide the measurement target gas to the measurement electrode 44 using the flow path CH(B) having at least one face defined by the fourth diffusion control portion 18B. Thus, the gas sensor element 101 can bring the diffusion mode of the measurement target gas moving toward the measurement electrode 44 closer to a favorable diffusion mode, such as Knudsen diffusion, by means of the porous diffusion layer 91 that blocks the predetermined region of the flow path CH(B) through which the measurement target gas is guided.

A face of the flow path CH(B) other than the face defined by the fourth diffusion control portion 18B (the upper face in the example shown in FIG. 6) is defined (demarcated) by the second solid electrolyte layer 6. The porous diffusion layer 91 is disposed at the entrance of the flow path CH(B), i.e. upstream of the measurement electrode 44, and is, particularly, disposed at a position where the distance d2 to the measurement electrode 44 is 0.15 mm or less. This porous diffusion layer 91 blocks the predetermined region of the entrance of the flow path CH(B), specifically, blocks 70% or more.

Particularly, in the example shown in FIG. 6, the porous diffusion layer 91 is in contact with the fourth diffusion control portion 18B (diffusion control portion) and a face defining the measurement target gas flow portion 7 (internal space) (the second solid electrolyte layer 6; particularly, the lower face of the second solid electrolyte layer 6 in the example shown in FIG. 6). In other words, no space (gap) is present between the porous diffusion layer 91 and the fourth diffusion control portion 18B and between the porous diffusion layer 91 and the face defining the measurement target gas flow portion 7. The gas sensor element 101 can thus prevent the measurement target gas from reaching the measurement electrode 44 from at least either the gap between the porous diffusion layer 91 and the fourth diffusion control portion 18B or the gap between the porous diffusion layer 91 and the face defining the measurement target gas flow portion 7. Accordingly, the gas sensor element 101 can bring the diffusion mode of the measurement target gas moving toward the measurement electrode 44 closer to a favorable diffusion mode, such as Knudsen diffusion, by means of the porous diffusion layer 91 that blocks the predetermined region of the flow path CH(B) through which the measurement target gas is guided.

Porous Diffusion Layer and Diffusion Control Portion According to Variation

As described above, the porous diffusion layer for making the diffusion mode around the measurement electrode 44 favorable in the gas sensor element 101 may be in contact with the measurement electrode 44. The flow path having a predetermined region blocked by the porous diffusion layer may be defined by a diffusion control portion. This diffusion control portion may extend downstream, e.g. may extend downstream of the measurement electrode 44. The following is a description of an example of the gas sensor element 101 (element substrate 100) that includes a porous diffusion layer in contact with the measurement electrode 44, and a diffusion control portion extending downstream of the measurement electrode 44, with reference to FIG. 7.

FIG. 7 is an illustrative enlarged view of key parts of the element substrate 100 (gas sensor element 101) that includes a porous diffusion layer 91C and a fourth diffusion control portion 18C according to a variation. Specifically, FIG. 7 shows an example of the porous diffusion layer 91C and the fourth diffusion control portion 18C, which are located upstream of the measurement electrode 44 and extend downstream (i.e. toward the measurement electrode 44). Note that the first solid electrolyte layer 4, the spacer layer 5, the second solid electrolyte layer 6, and other members in FIG. 7 are the same as those described with reference to FIGS. 2, 3 and other figures, and the description thereof is not repeated. The gas sensor element 101 may include the porous diffusion layer 91C, which will be described in more detail below, instead of the porous diffusion layer 91.

Like the porous diffusion layer 91A, the porous diffusion layer 91C is disposed upstream of the measurement electrode 44 and extends downstream, specifically, toward the measurement electrode 44, and is in contact with the measurement electrode 44. Particularly, the porous diffusion layer 91C illustrated in FIG. 7 extends downstream of the measurement electrode 44, and covers the measurement electrode 44. Like the above-described porous diffusion layers 91 and 91A, the porous diffusion layer 91C has a porosity lower than the porosity of the leading end protection layer 200, and is 5% or more and 25% or less. Like the porous diffusion layers 91 and 91A, the porous diffusion layer 91C is located upstream of the measurement electrode 44, and blocks a predetermined region (specifically, 70% or more) of a flow path CH(C) of the measurement target gas.

Like the fourth diffusion control portion 18B, the fourth diffusion control portion 18C is disposed upstream of the measurement electrode 44, and extends downstream (i.e. toward the measurement electrode 44). Particularly, the fourth diffusion control portion 18C illustrated in FIG. 7 extends downstream of the measurement electrode 44. Specifically, the fourth diffusion control portion 18C disposed upstream of the measurement electrode 44 extends downstream and is in contact with the spacer layer 5. In addition, like the fourth diffusion control portions 18 and 18B, the fourth diffusion control portion 18C has a porosity lower than the porosity of the porous diffusion layer 91; i.e. the fourth diffusion control portion 18C is denser than the porous diffusion layer 91C. The fourth diffusion control portion 18C applies predetermined diffusion resistance to the measurement target gas in the measurement target gas flow portion 7 (internal space).

In the example shown in FIG. 7, the flow path CH(C) defined by the fourth diffusion control portion 18C and the second solid electrolyte layer 6 is integrated with the third internal cavity 19C in which the measurement electrode 44 is disposed. That is, the fourth diffusion control portion 18C extends downstream, particularly, downstream of the measurement electrode 44 and is in contact with the spacer layer 5. The flow path CH(C) of the measurement target gas moving toward the measurement electrode 44 is defined by the fourth diffusion control portion 18C and the second solid electrolyte layer 6. Specifically, in the example shown in FIG. 7, the flow path CH(C) (i.e. the third internal cavity 19C) has an upper face defined (demarcated) by the second solid electrolyte layer 6, a lower face defined by the fourth diffusion control portion 18C, and side and rear faces defined by the spacer layer 5. The porous diffusion layer 91C blocks the entirety of the flow path CH(C) (i.e. the third internal cavity 19C) defined by the fourth diffusion control portion 18C and the second solid electrolyte layer 6.

Like the flow path CH and CH(B), the flow path CH(C) has at least one face defined (demarcated) by the fourth diffusion control portion 18C. In the example shown in FIG. 7, the lower face of the flow path CH(C) is defined by the fourth diffusion control portion 18C. The gas sensor element 101 can guide the measurement target gas to the measurement electrode 44 using the flow path CH(C) having at least one face defined by the fourth diffusion control portion 18C. Accordingly, the gas sensor element 101 can bring the diffusion mode of the measurement target gas moving toward the measurement electrode 44 closer to a favorable diffusion mode, such as Knudsen diffusion, by means of the porous diffusion layer 91 that blocks the predetermined region of the flow path CH(C) through which the measurement target gas is guided.

A face (the upper face in the example shown in FIG. 7) of the flow path CH(C) other than the face defined by the fourth diffusion control portion 18C is defined (demarcated) by the second solid electrolyte layer 6. The porous diffusion layer 91C is disposed at the entrance of the flow path CH(C), i.e. upstream of the measurement electrode 44, extends downstream, and is in contact with the measurement electrode 44. The porous diffusion layer 91 blocks the predetermined region, specifically, 70% or more of a cross-section of the flow path CH(C) (i.e. the third internal cavity 19C) that is orthogonal to the flow direction DR of the measurement target gas.

Particularly, the porous diffusion layer 91C in the example shown in FIG. 7 is in contact with the fourth diffusion control portion 18C (diffusion control portion) and the face defining the measurement target gas flow portion 7 (internal space) (the second solid electrolyte layer 6; particularly, the lower face of the second solid electrolyte layer 6 in the example shown in FIG. 7). That is, no space (gap) is present between the porous diffusion layer 91C and the fourth diffusion control portion 18C and between the porous diffusion layer 91C and the face defining the measurement target gas flow portion 7. The gas sensor element 101 can thus prevent the measurement target gas from reaching the measurement electrode 44 from at least either the gap between the porous diffusion layer 91C and the fourth diffusion control portion 18C or the gap between the porous diffusion layer 91C and the face defining the measurement target gas flow portion 7. Accordingly, the gas sensor element 101 can bring the diffusion mode of the measurement target gas moving toward the measurement electrode 44 closer to a favorable diffusion mode, such as Knudsen diffusion, by means of the porous diffusion layer 91C that blocks the predetermined region of the flow path CH(C) through which the measurement target gas is guided.

Flow Path According to Variations

All of the above-described flow paths CH, CH(B) and CH(C) have one face (e.g. the lower face) defined (demarcated) by a diffusion control portion (any of the fourth diffusion control portions 18, 18B, and 18C). However, it is not essential that the flow path having a predetermined region blocked by a porous diffusion layer (any of the porous diffusion layers 91, 91A and 91C) for making the diffusion mode around the measurement electrode 44 favorable has one face defined by a diffusion control portion. The flow path having a predetermined region blocked by a porous diffusion layer for making the diffusion mode around the measurement electrode 44 favorable may have a plurality of faces defined by diffusion control portions; for example, at least two faces may be defined by diffusion control portions. Alternatively, the flow path having a predetermined region blocked by a porous diffusion layer for making the diffusion mode around the measurement electrode 44 favorable need not be defined by a diffusion control portion. An example where a flow path having a predetermined region blocked by a porous diffusion layer has a plurality of faces defined by porous diffusion layers will be described below with reference to FIGS. 8 to 10. Also, an example where a flow path having a predetermined region blocked by a porous diffusion layer is not defined (demarcated) by a diffusion control portion will be described with reference to FIG. 11.

Figure 8:
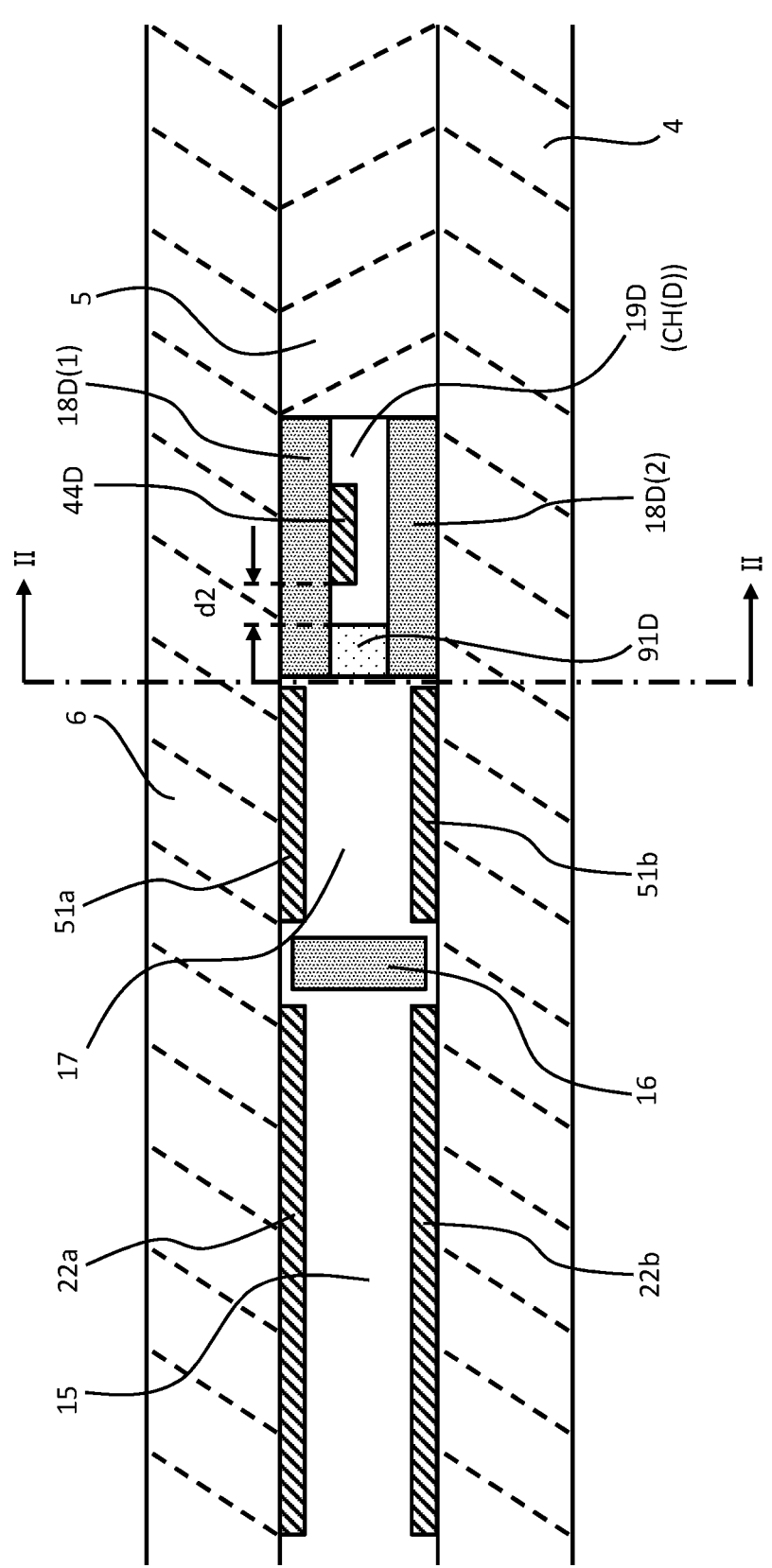
FIG. 8 is an illustrative enlarged view of key parts of an element substrate that includes a flow path according to a variation.

Example 1 of Flow Path Having a Plurality of Faces Defined by Diffusion Control Portions FIG. 8 is an illustrative enlarged view of key parts of the element substrate 100 (the gas sensor element 101) that includes a flow path CH(D) according to a variation. Specifically, FIG. 8 shows an example of the flow path CH(D) having an upper face and a lower face that are defined (demarcated) by a fourth diffusion control portion 18D(1) and a fourth diffusion control portion 18D(2), respectively. In the following description, the fourth diffusion control portion 18D(1) and the fourth diffusion control portion 18D(2) will both be referred to as fourth diffusion control portions 18D, unless a distinction is specifically made therebetween. The first solid electrolyte layer 4, the spacer layer 5, the second solid electrolyte layer 6, and other members in FIG. 8 are the same as those described with reference to FIGS. 2 and 3 and other figures, and the description thereof is not repeated. The gas sensor element 101 may have the flow path CH(D) and a porous diffusion layer 91D, which will be described in detail below, instead of the flow path CH and the porous diffusion layer 91 that have been described with reference to FIG. 2 and other figures.

All of the flow paths CH, CH(B) and CH(C) that have been described above have one face defined (demarcated) by a diffusion control portion (any of the fourth diffusion control portions 18, 18B and 18C). Specifically, the flow path CH and the other flow paths all have a lower face defined (demarcated) by a diffusion control portion (any of the fourth diffusion control portions 18, 18B and 18C) and an upper face defined (demarcated) by the second solid electrolyte layer 6. In contrast, the flow path CH(D) has at least two faces defined by diffusion control portions (specifically, the fourth diffusion control portions 18D). That is, the flow path CH(D) has an upper face defined by the fourth diffusion control portion 18D(1) and a lower face defined by the fourth diffusion control portion 18D(2).

The flow path CH(D), which has an upper face and a lower face that are defined by the fourth diffusion control portion 18D(1) and the fourth diffusion control portion 18D(2), is integrated with a third internal cavity 19D, in which a measurement electrode 44D is disposed. Specifically, in the example shown in FIG. 8, the flow path CH(D) (i.e. the third internal cavity 19D) has an upper face and a lower face defined (demarcated) by the fourth diffusion control portions 18D, and side and rear faces defined (demarcated) by the spacer layer 5. The entrance of the flow path CH(D) (i.e. the third internal cavity 19D) defined by the fourth diffusion control portion 18D(1) and the fourth diffusion control portion 18D(2) is blocked by the porous diffusion layer 91D, which is separated from the measurement electrode 44D by the distance d2 that is 0.15 mm or less.

The basic configuration of the fourth diffusion control portions 18D are similar to that of the above-described fourth diffusion control portion 18. That is, the fourth diffusion control portions 18D apply predetermined diffusion resistance to the measurement target gas in the measurement target gas flow portion 7 (internal space). In addition, the fourth diffusion control portions 18D have a porosity lower than that of the porous diffusion layer 91D, i.e. is denser than the porous diffusion layer 91D.

Meanwhile, the fourth diffusion control portions 18D are constituted by oxygen-ion-conductive solid electrolyte layers made of zirconia ($ZrO_2$) or the like. The measurement electrode 44D illustrated in FIG. 8 is provided on a surface of one of the fourth diffusion control portions 18D. Thus, the fourth diffusion control portions 18D are constituted by oxygen-ion-conductive solid electrolyte layers such that oxygen can be pumped in and out via the fourth diffusion control portions 18D.

Like the fourth diffusion control portions 18B and 18C, the fourth diffusion control portions 18D are located upstream of the measurement electrode 44D and extend downstream (i.e. toward the measurement electrode 44D). Particularly, like the fourth diffusion control portions 18B and 18C, the fourth diffusion control portions 18D illustrated in FIG. 8 extend downstream of the measurement electrode 44D and are in contact with the spacer layer 5.

The measurement electrode 44D is the same as the above-described measurement electrode 44, except that the measurement electrode 44D is provided on the lower face of the fourth diffusion control portion 18D(1) instead of the lower face of the second solid electrolyte layer 6 adjoining (facing) the third internal cavity 19. The measurement pump cell 41 includes the measurement electrode 44, the external pump electrode 23, the second solid electrolyte layer 6, the spacer layer 5, the first solid electrolyte layer 4, and the oxygen-ion-conductive fourth diffusion control portions 18D. It is not essential that the measurement electrode 44D is provided on the lower face of the fourth diffusion control portion 18D(1), and the measurement electrode 44D may alternatively be provided on the upper face of the fourth diffusion control portion 18D(2).

The porous diffusion layer 91D is the same as the above-described porous diffusion layer 91, except that the porous diffusion layer 91D is disposed on the flow path CH(D) having at least two faces (the upper and lower faces in the example shown in FIG. 8) defined by the fourth diffusion control portions 18D. That is, the porosity of the porous diffusion layer 91D is lower than the porosity of the leading end protection layer 200, and is 5% or more and 25% or less. The porous diffusion layer 91D is located at a position that is upstream of the measurement electrode 44D in the flow direction DR of the measurement target gas and where the distance to the measurement electrode 44D is 0.15 mm or less. This porous diffusion layer 91D blocks a predetermined region of the entrance of the flow path CH(D). Specifically, the area of a face of the porous diffusion layer 91D that is orthogonal to the flow direction DR of the measurement target gas accounts for (blocks) 70% or more of the area of a cross-section of the flow path CH(D) of the measurement target gas that is orthogonal to the flow direction DR of the measurement target gas, as will be described later with reference to FIG. 9.

Figure 9:
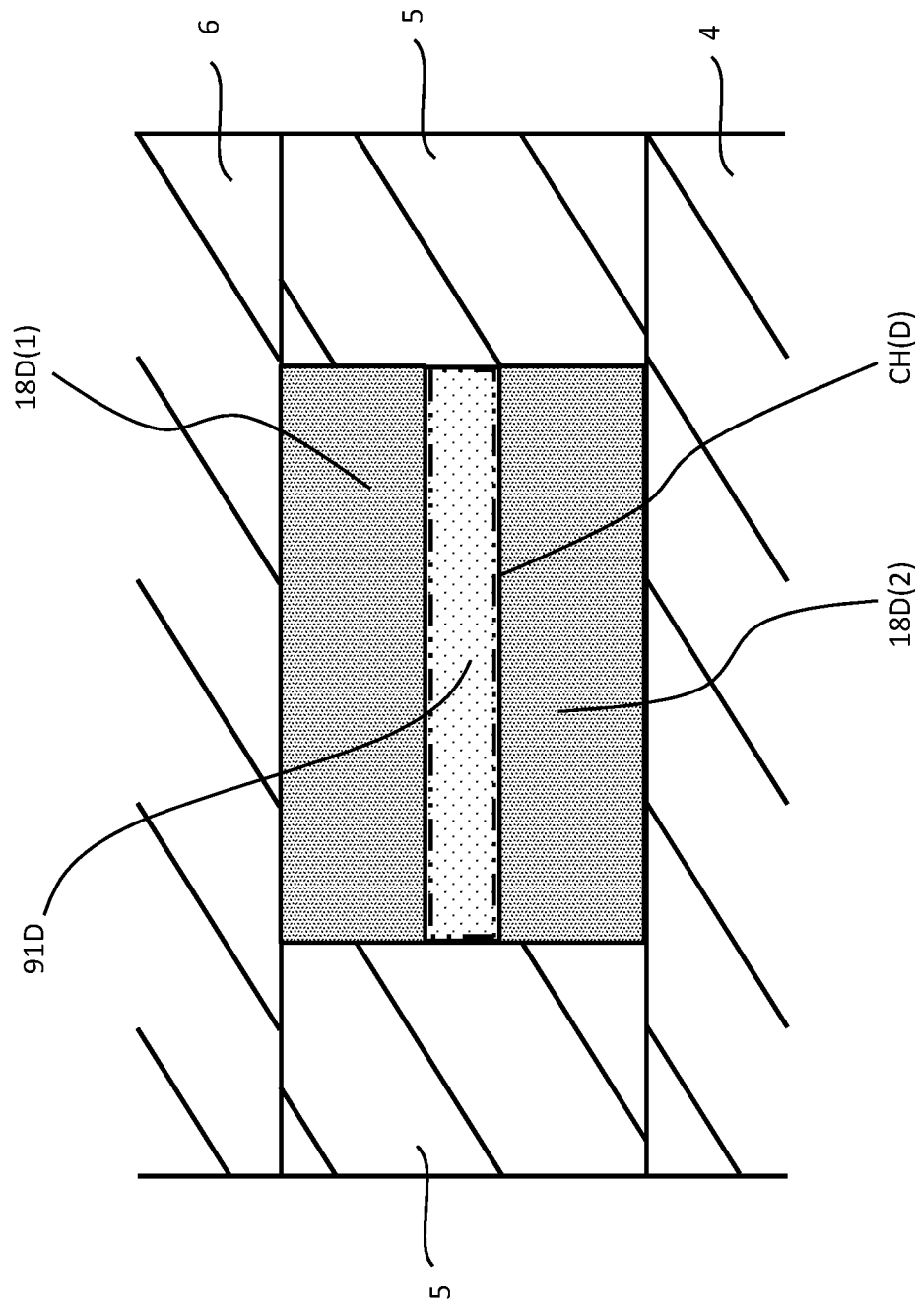
FIG. 9 shows an example of a cross-section of the element substrate shown in FIG. 8 taken along a line defined by arrows II-II.

FIG. 9 shows an example of a cross-section of the element substrate 100 shown in FIG. 8 taken along a line defined by arrows II-II. The area of the face of the porous diffusion layer 91D that is orthogonal to the flow direction DR of the measurement target gas (from the proximal side to the distal side of the sheet in the example shown in FIG. 9) accounts for 70% or more of the area of the cross-section of the flow path CH(D) that is orthogonal to the flow direction DR of the measurement target gas. In the example shown in FIG. 9, the flow path CH(D) of the measurement target gas from the second internal cavity 17 to the third internal cavity 19 is formed (defined) by the fourth diffusion control portions 18D. Specifically, the flow path CH(D) is formed as a slit (gap) between the fourth diffusion control portion 18D(1) and the fourth diffusion control portion 18D(2). That is, the flow path CH illustrated by two-dot chain lines in FIG. 9 has an upper face demarcated (defined) by the lower face of the fourth diffusion control portion 18D(1), a lower face demarcated (defined) by the upper face of the fourth diffusion control portion 18D(2), and side faces demarcated (defined) by the spacer layer 5. The face of the porous diffusion layer 91D that is orthogonal to the flow direction DR of the measurement target gas accounts for 70% or more of the area of the cross-section of the flow path CH(D) that is orthogonal to the flow direction DR of the measurement target gas. That is, the porous diffusion layer 91D that is in contact with the upper face of the fourth diffusion control portion 18D(2) accounts for (blocks) 70% or more of the flow path CH(D).

In the example shown in FIG. 9, no space (gap) is present between the upper face of the porous diffusion layer 91D and the lower face of the fourth diffusion control portion 18D(1). That is, in the example shown in FIG. 9, the proportion of the area of the face of the porous diffusion layer 91D that is orthogonal to the flow direction DR of the measurement target gas to the area of the cross-section of the flow path CH(D) that is orthogonal to the flow direction DR of the measurement target gas is 100%. However, the proportion of the area of the face of the porous diffusion layer 91D that is orthogonal to the flow direction DR of the measurement target gas to the area of the cross-section of the flow path CH(D) that is orthogonal to the flow direction DR of the measurement target gas need only be 70% or more, and need not necessarily be 100%. In other words, the face of the porous diffusion layer 91D that is orthogonal to the flow direction DR of the measurement target gas need not occupy the entire section of the flow path CH(D) that is orthogonal to the flow direction DR of the measurement target gas. In the example shown in FIG. 9, the porous diffusion layer 91D and the fourth diffusion control portion 18D(1) need not be in contact with each other; specifically, the upper face of the porous diffusion layer 91D and the lower face of the fourth diffusion control portion 18D(1) need not be in contact with each other.

As described above, at least two faces (the upper and lower faces in the example shown in FIG. 8) of the flow path CH(D) are defined by the fourth diffusion control portions 18D. Furthermore, the fourth diffusion control portions 18D are denser than (i.e. have a porosity lower than) the porous diffusion layer 91D, as mentioned above. In other words, in the gas sensor element 101, the fourth diffusion control portions 18D that are denser than the porous diffusion layer 91D define (demarcate) at least two faces of the flow path CH(D) that guides the measurement target gas to the measurement electrode 44D. The gas sensor element 101 can thus guide the measurement target gas to the measurement electrode 44D using the flow path CH(D) having at least two faces defined by the fourth diffusion control portions 18D, which are denser than the porous diffusion layer 91D. The gas sensor element 101 can further reduce the likelihood of a situation where, for example, the measurement target gas leaking out from an intermediate portion of the flow path CH(D) reaches the measurement electrode 44D without the diffusion mode being changed by the porous diffusion layer 91D. Accordingly, the gas sensor element 101 can bring the diffusion mode of the measurement target gas moving toward the measurement electrode 44D closer to a favorable diffusion mode, such as Knudsen diffusion, by means of the porous diffusion layer 91D that blocks the predetermined region of the flow path CH(D) through which the measurement target gas is guided.

Example 2 of Flow Path Having a Plurality of
Faces Defined by Diffusion Control Portions FIG. 10 is an illustrative enlarged view of key parts of the element substrate 100 (gas sensor element 101) that includes a flow path CH(E), which is the same as the flow path CH(D) illustrated in FIG. 8, and a porous diffusion layer 91E, which is different from the porous diffusion layer 91D illustrated in FIG. 8. Specifically, FIG. 10 shows an example of the flow path CH(E) having an upper face and a lower face that are defined (demarcated) by a fourth diffusion control portion 18E(1) and a fourth diffusion control portion 18E(2), respectively, and the porous diffusion layer 91E that extends downstream. In the following description, the fourth diffusion control portion 18E(1) and the fourth diffusion control portion 18E(2) are both referred to as fourth diffusion control portions 18E, unless a distinction is specifically made therebetween. The first solid electrolyte layer 4, the spacer layer 5, the second solid electrolyte layer 6, and other members in FIG. are the same as those described with reference to FIGS. 2, 3 and other figures, and the description thereof is not repeated.

Like the flow path CH(D), the flow path CH(E) has at least two faces (the upper face and the lower face in the example shown in FIG. 10) defined (demarcated) by the fourth diffusion control portions 18E. That is, the flow path CH(E) has an upper face defined by the fourth diffusion control portion 18E(1) and a lower face defined by the fourth diffusion control portion 18E(2), and is integrated with a third internal cavity 19E, in which the measurement electrode 44 is disposed. Specifically, in the example shown in FIG. 10, the flow path CH(E) (i.e. the third internal cavity 19E) has the upper and lower faces defined (demarcated) by the fourth diffusion control portions 18E, and side and rear faces defined (demarcated) by the spacer layer 5. The entire flow path CH(E) (i.e. the third internal cavity 19E) is blocked by the porous diffusion layer 91E.

The fourth diffusion control portions 18E have the same configuration as the fourth diffusion control portions 18D. That is, the fourth diffusion control portions 18E apply predetermined diffusion resistance to the measurement target gas in the measurement target gas flow portion 7 (internal space). The fourth diffusion control portions 18E have a porosity lower than the porosity of the porous diffusion layer 91E, i.e. are denser than the porous diffusion layer 91E. The fourth diffusion control portions 18E are constituted by oxygen-ion-conductive solid electrolyte layers made of zirconia ($ZrO_2$) or the like. The fourth diffusion control portions 18E are located upstream of a measurement electrode 44E and extend downstream (i.e. toward the measurement electrode 44E); particularly, the fourth diffusion control portions 18E illustrated in FIG. 10 extend downstream of the measurement electrode 44E. Specifically, the fourth diffusion control portions 18E disposed upstream of the measurement electrode 44E extend downstream and are in contact with the spacer layer 5.

As described above, at least two faces of the flow path CH(E) (the upper and lower faces in the example shown in FIG. 10) are defined by the fourth diffusion control portions 18E. In addition, the fourth diffusion control portions 18E are denser than (i.e. have a porosity lower than) the porous diffusion layer 91E, as mentioned above. In other words, in the gas sensor element 101, the fourth diffusion control portions 18E that are denser than the porous diffusion layer 91E define (demarcate) at least two faces of the flow path CH(E) that guides the measurement target gas to the measurement electrode 44E. The gas sensor element 101 can thus guide the measurement target gas to the measurement electrode 44E using the flow path CH(E) having at least two faces defined by the fourth diffusion control portions 18E, which are denser than the porous diffusion layer 91E. The gas sensor element 101 can further reduce the likelihood of a situation where, for example, the measurement target gas leaking out from an intermediate portion of the flow path CH(E) reaches the measurement electrode 44E without the diffusion mode being changed by the porous diffusion layer 91E. Accordingly, the gas sensor element 101 can bring the diffusion mode of the measurement target gas moving toward the measurement electrode 44E closer to a favorable diffusion mode, such as Knudsen diffusion, by means of the porous diffusion layer 91E that blocks the predetermined region of the flow path CH(E) through which the measurement target gas is guided.

Like the measurement electrode 44D, the measurement electrode 44E is provided on the lower face of the fourth diffusion control portion 18E(1). The measurement pump cell 41 includes the measurement electrode 44, the external pump electrode 23, the second solid electrolyte layer 6, the spacer layer 5, the first solid electrolyte layer 4, and the oxygen-ion-conductive fourth diffusion control portions 18E. It is not essential that the measurement electrode 44E is provided on the lower face of the fourth diffusion control portion 18E(1), and the measurement electrode 44E may alternatively be provided on the upper face of the fourth diffusion control portion 18E(2).

The porous diffusion layer 91E is the same as the porous diffusion layer 91D, except that the porous diffusion layer 91E is in contact with the measurement electrode 44E. That is, like the porous diffusion layers 91A and 91C, the porous diffusion layer 91E is located upstream of the measurement electrode 44E and extends downstream; specifically, the porous diffusion layer 91E extends toward the measurement electrode 44E and is in contact with the measurement electrode 44E. Particularly, the porous diffusion layer 91E illustrated in FIG. 10 extends downstream of the measurement electrode 44E and covers the measurement electrode 44E. Like the above-described porous diffusion layer 91 and the other porous diffusion layers, the porosity of the porous diffusion layer 91E is lower than the porosity of the leading end protection layer 200, and is 5% or more and 25% or less. The area of a face of the porous diffusion layer 91E that is orthogonal to the flow direction DR of the measurement target gas accounts for (blocks) 70% or more of the area of a cross-section of the flow path CH(E) of the measurement target gas that is orthogonal to the flow direction DR of the measurement target gas.

Example of Flow Path that is not Defined by
Diffusion Control Portion

Figure 11:
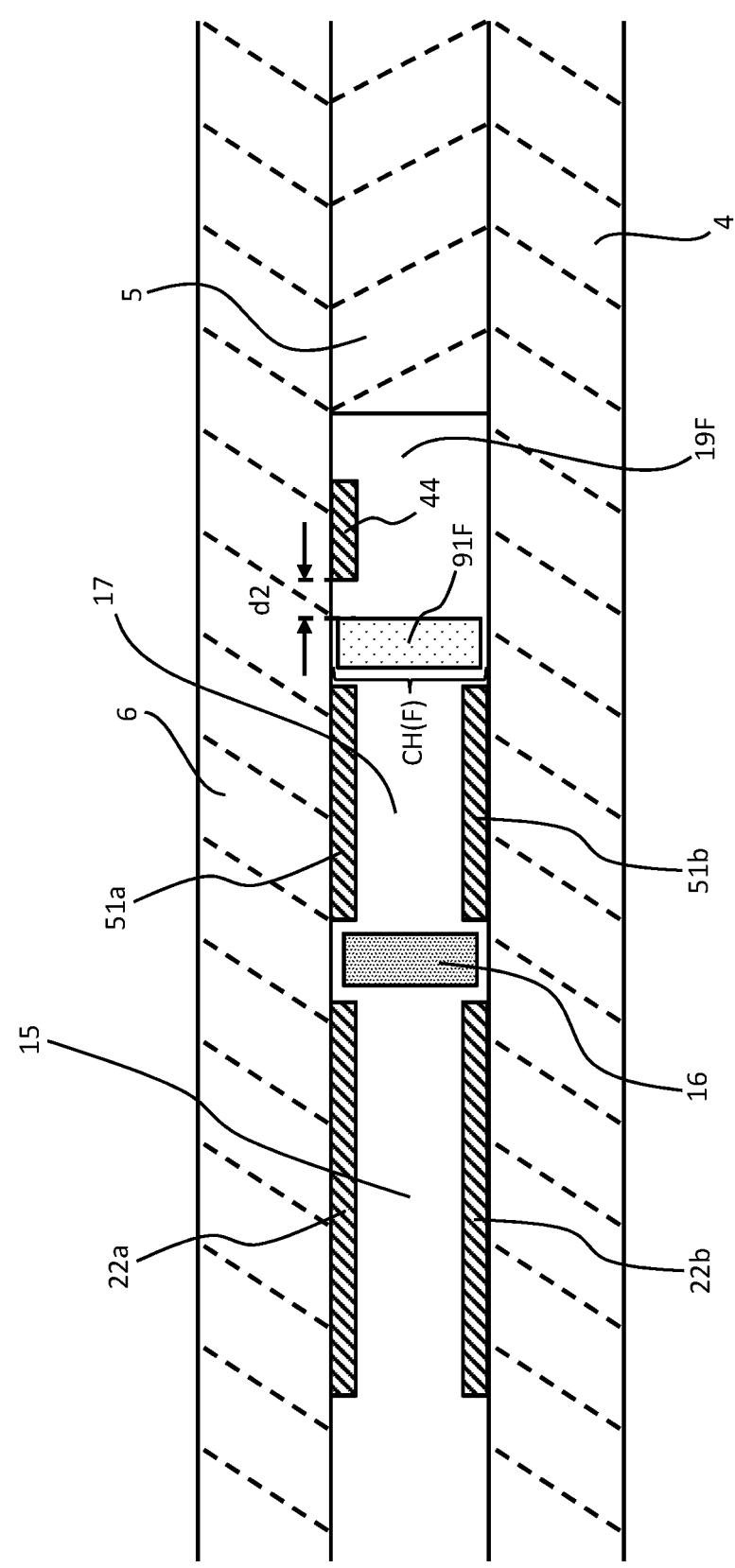
FIG. 11 is an illustrative enlarged view of key parts of an element substrate that includes a flow path not defined by the diffusion control portion.

FIG. 11 is an illustrative enlarged view of key parts of the element substrate 100 (the gas sensor element 101) that includes a flow path CH(F) that is not defined by a diffusion control portion (e.g. the fourth diffusion control portion 18). Specifically, FIG. 11 shows an example of a porous diffusion layer 91F that blocks the predetermined region of the flow path CH(F) of the measurement target gas moving toward the measurement electrode 44, without the fourth diffusion control portion 18. The gas sensor element 101 may have the flow path CH(F) and the porous diffusion layer 91F, both of which will be described in more detail below, instead of the flow path CH and the porous diffusion layer 91 that have been described with reference to FIG. 2 and other figures.

All of the above-described flow paths CH, CH(B), CH(C), CH(D), and CH(E) have at least one face (e.g. a lower face) defined (demarcated) by a diffusion control portion (e.g. the fourth diffusion control portion 18). In other words, the above-described gas sensor element 101 has a diffusion control portion that applies predetermined diffusion resistance to the measurement target gas in the measurement target gas flow portion 7, has a porosity lower than the porosity of the porous diffusion layer, and is located upstream of the measurement electrode 44. The flow path (e.g. the above-described flow path CH), which has a predetermined region (specifically, 70% or more) blocked by the porous diffusion layer 91 or the like, has at least one face defined by the diffusion control portion.

In contrast, the flow path CH(F) illustrated in FIG. 11 does not have any face defined by the diffusion control portion (e.g. the fourth diffusion control portion 18). Specifically, the flow path CH(F) illustrated in FIG. 11 is the measurement target gas flow portion 7, and has an upper face defined (demarcated) by the lower face of the second solid electrolyte layer 6, a lower face defined (demarcated) by the upper face of the first solid electrolyte layer 4, and side faces defined (demarcated) by the spacer layer 5.

A face of the porous diffusion layer 91F that is orthogonal to the flow direction DR of the measurement target gas accounts for 70% or more of a cross-section of the flow path CH(F) that is orthogonal to the flow direction DR of the measurement target gas (from the left side to the right side of the sheet in the example shown in FIG. 11). That is, the area of the face of the porous diffusion layer 91F that is orthogonal to the flow direction DR of the measurement target gas accounts for (blocks) 70% or more of the area of the cross-section of the flow path CH(F) (i.e. the measurement target gas flow portion 7) that is orthogonal to the flow direction DR of the measurement target gas.

The porous diffusion layer 91F is the same as the above-described porous diffusion layer 91 and the other porous diffusion layers, except that the porous diffusion layer 91F blocks a predetermined region (specifically, 70% or more) of the flow path CH(F), which does not have any face defined by the diffusion control portion (e.g. the fourth diffusion control portion 18). That is, the porosity of the porous diffusion layer 91F is lower than the porosity of the leading end protection layer 200, and is 5% or more and 25% or less. The porous diffusion layer 91F is located at a position that is upstream of the measurement electrode 44 in the flow direction DR of the measurement target gas and where the distance to the measurement electrode 44 is 0.15 mm or less. Furthermore, the area of the face of the porous diffusion layer 91F that is orthogonal to the flow direction DR of the measurement target gas accounts for (blocks) 70% or more of the area of the cross-section of the flow path CH(F) that is orthogonal to the flow direction DR of the measurement target gas. The gas sensor element 101 makes the diffusion mode around the measurement electrode 44 a mode of diffusing while repeatedly colliding with a wall face of a sufficiently narrow flow path, as in Knudsen diffusion, by means of the porous diffusion layer 91F.

The measurement electrode 44 is disposed in a third internal cavity 19F (internal cavity), the upstream side of which is defined (demarcated) by the porous diffusion layer 91F, in the measurement target gas flow portion 7 (the internal space). The measurement target gas that has been introduced into the third internal cavity 19F through the flow path CH(F) having a predetermined region (70% or more) blocked by the porous diffusion layer 91F is subjected to measurement of the nitrogen oxide (NO$_x$) concentration by operation of the measurement pump cell 41. The third internal cavity 19F is the same as the third internal cavity 19, except that the upstream side of the third internal cavity 19F is defined by the porous diffusion layer 91F capable of applying predetermined diffusion resistance to the measurement target gas, instead of the fourth diffusion control portion 18.

In the gas sensor element 101, the flow path of the measurement target gas moving toward the measurement electrode 44 is not limited to a flow path having at least one face defined by the diffusion control portion (e.g. the fourth diffusion control portion 18) that is disposed upstream of the measurement electrode 44, as described with reference to FIG. 11. In the gas sensor element 101, the flow path having a predetermined region blocked by the porous diffusion layer for making the diffusion mode around the measurement electrode 44 favorable is not limited to a flow path having at least one face defined by a diffusion control portion that is disposed upstream of the measurement electrode 44. In the gas sensor element 101, the flow path of the measurement target gas moving toward the measurement electrode 44 need only be such that a face of the aforementioned porous diffusion layer that is orthogonal to the flow direction DR of the measurement target gas accounts for 70% or more of a cross-section of the flow path that is orthogonal to the flow direction DR of the measurement target gas. The porous diffusion layer that makes the diffusion mode around the measurement electrode 44 favorable need only be located at a position that is upstream of the measurement electrode 44 and where the distance to the measurement electrode 44 is 0.15 mm or less, and be capable of blocking a predetermined region (specifically, 70% or more) of the flow path leading to the measurement electrode 44. It is not essential for the gas sensor element 101 that the flow path having a predetermined region blocked by the porous diffusion layer has at least one face defined by the diffusion control portion disposed upstream of the measurement electrode 44.

Note that FIG. 11 shows an example where the lengthwise direction of the measurement target gas flow portion 7 (the lengthwise direction of the gas sensor element 101) coincides with the flow direction DR of the measurement target gas. However, it is not essential for the gas sensor element 101 that the lengthwise direction of the measurement target gas flow portion 7 (the lengthwise direction of the gas sensor element 101) coincides with the flow direction DR of the measurement target gas. In the gas sensor element 101, the flow direction DR of the measurement target gas on the flow path CH(F) may be inclined relative to the lengthwise direction of the measurement target gas flow portion 7, and may be, for example, a direction orthogonal to the lengthwise direction of the measurement target gas flow portion 7.

Example where Leading End Protection Layer has Multi-Layer Structure

The leading end protection layer 200 illustrated in FIG. 1 has a constant porosity throughout. However, it is not essential that the porosity is constant throughout the leading end protection layer of the gas sensor element 101. The leading end protection layer of the gas sensor element 101 may have a multi-layer structure. An example where the leading end protection layer of the gas sensor element 101 has a multi-layer structure will be described below with reference to FIG. 12.

Figure 12:
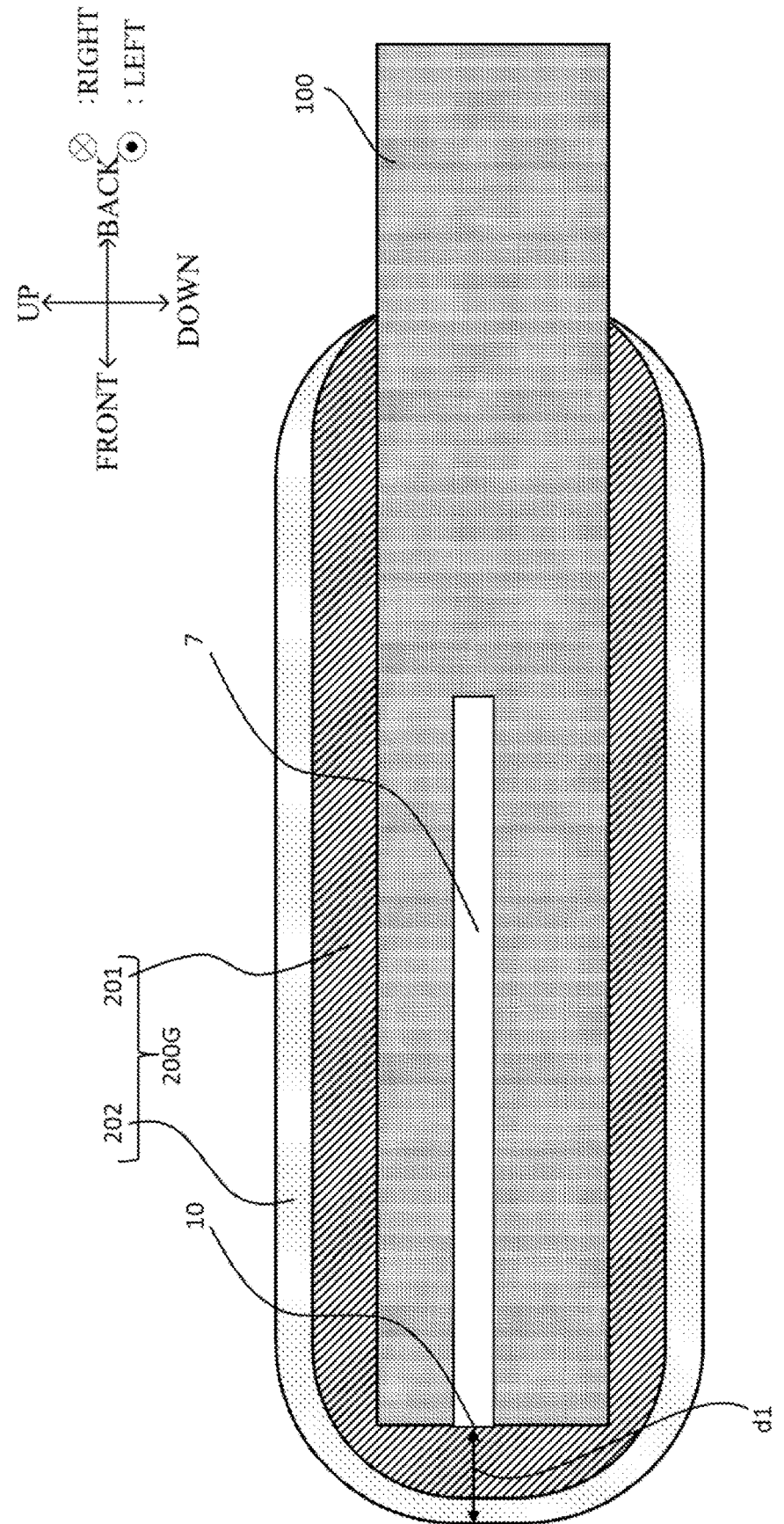
FIG. 12 is a cross-sectional schematic view that schematically shows an example of a configuration of a sensor element that includes a leading end protection layer according to a variation.

FIG. 12 is a cross-sectional schematic view that schematically shows an example of a configuration of the gas sensor element 101 that has a leading end protection layer 200G according to a variation. Specifically, FIG. 12 shows an example of the leading end protection layer 200G, which includes an internal leading end protection layer 201 and an external leading end protection layer 202 that have different porosities. The gas sensor element 101 may have the leading end protection layer 200G illustrated in FIG. 12 that includes the internal leading end protection layer 201 and the external leading end protection layer 202, instead of the leading end protection layer 200 illustrated in FIG. 1.

The leading end protection layer 200G covers at least the face of the element substrate 100 (the leading end face of the element substrate 100) in which the gas inlet 10 is open. In the example shown in FIG. 12, the leading end protection layer 200G covers the leading end face of the element substrate 100 and the four side faces of the element substrate 100 that are continuous with the leading end face.

The leading end protection layer 200G includes at least the internal leading end protection layer 201 and the external leading end protection layer 202. The internal leading end protection layer 201 is in contact with the face of the element substrate 100 in which the gas inlet 10 is open. The external leading end protection layer 202 constitutes an outermost face of the leading end protection layer 200G. The porosity of the internal leading end protection layer 201 is larger than the porosity of the external leading end protection layer 202, and the thickness of the internal leading end protection layer 201 is 30% or more and 90% or less of the thickness of the leading end protection layer 200G. That is, the leading end protection layer 200G includes the internal leading end protection layer 201 and the external leading end protection layer 202, with the porosity of the internal leading end protection layer 201 being larger than the porosity of the external leading end protection layer 202 and the thickness of the internal leading end protection layer 201 being 30% to 90% of the thickness of the leading end protection layer 200G.

In this configuration, the leading end protection layer 200G includes at least two layers, with the internal layer (e.g. the internal leading end protection layer 201) having a porosity larger than that of the external layer (e.g. the external leading end protection layer 202). The gas sensor element 101 can prevent clogging caused by poisonous substances or the like in the vicinity of the gas inlet 10 and avoid a decrease in NO$_x$ sensitivity as a result of the porosity of the internal layer (the internal leading end protection layer 201) being larger than the porosity of the external layer (the external leading end protection layer 202).

Particularly, the gas sensor element 101 achieves the following effects due to a large thickness of the internal leading end protection layer 201 having a porosity larger than the porosity of the external leading end protection layer 202, i.e. a large proportion of the thickness of the internal leading end protection layer 201 to the thickness of the leading end protection layer 200G. That is, the likelihood of clogging caused by poisonous substances or the like in the vicinity of the gas inlet 10 is prevented; particularly, a layer closer to the gas inlet (i.e. the internal leading end protection layer 201) is prevented from being clogged, by ensuring a sufficient thickness of the internal leading end protection layer 201 having a larger porosity. Specifically, the internal leading end protection layer 201 in contact with the gas inlet 10 can be prevented from being clogged with poisonous substances or the like, as a result of the proportion of the thickness of the internal leading end protection layer 201 having a larger porosity to the thickness of the leading end protection layer 200G being 30% to 90%.

Like the leading end protection layer 200, the leading end protection layer 200G has a predetermined thickness; specifically, the distance d1 from the outermost face of the leading end protection layer 200G to the gas inlet 10 is 0.2 mm or more. That is, in the example shown in FIG. 12, the distance d1 from the outermost face of the external leading end protection layer 202 to the gas inlet is 0.2 mm or more. The following effects can be achieved as a result of the distance d1 from the outermost face of the leading end protection layer 200G to the gas inlet 10 being sufficiently long (specifically, 0.2 mm or more), i.e. the thickness of the leading end protection layer 200G being sufficiently large. That is, it is possible to reliably trap (capture) poisonous substances or the like in the leading end protection layer 200G even in a harsh environment with a large amount of poisonous substances or the like, and to prevent clogging caused by poisonous substances or the like in the vicinity of the gas inlet 10 and avoid a decrease in NO$_x$ sensitivity.

The leading end protection layer 200G illustrated in FIG. 12 includes the internal leading end protection layer 201 and the external leading end protection layer 202, i.e. has a two-layer structure. However, it is not essential that the leading end protection layer 200G has a two-layer structure, and the leading end protection layer 200G may include three or more layers. That is, the leading end protection layer 200G may include yet another layer in addition to the internal leading end protection layer 201 and the external leading end protection layer 202. For example, the leading end protection layer 200G may have a three-layer structure, or a multi-layer structure with four or more layers. The leading end protection layer 200G need only include at least the internal leading end protection layer 201 that is in contact with the face of the element substrate 100 in which the gas inlet 10 is open, and the external leading end protection layer 202 that constitutes the outermost face of the leading end protection layer 200G. The leading end protection layer 200G need only be such that the porosity of the internal leading end protection layer 201 is larger than the porosity of the external leading end protection layer 202, and the thickness of the internal leading end protection layer 201 is 30% or more and 90% or less of the thickness of the leading end protection layer 200G.

Features

As described above, the gas sensor element 101 according to the present embodiment includes the element substrate 100, the leading end protection layer 200, the measurement electrode 44, and the porous diffusion layer 91. The gas sensor element 101 may include the leading end protection layer 200G instead of the leading end protection layer 200. Also, the gas sensor element 101 may include either the measurement electrode 44D or the measurement electrode 44E instead of the measurement electrode 44. Further, the gas sensor element 101 may include any of the porous diffusion layers 91A, 91C, 91D, 91E, and 91F instead of the porous diffusion layer 91. For example, the element substrate 100 includes the measurement target gas flow portion 7 as an internal space, and the measurement target gas is introduced into the measurement target gas flow portion 7 from the gas inlet 10, which is open in a surface of the element substrate 100. For example, the leading end protection layer 200 covers at least the face of the element substrate 100 in which the gas inlet 10 is open. The measurement electrode 44 is provided in the measurement target gas flow portion 7. For example, the porosity of the porous diffusion layer 91 is lower than the porosity of the leading end protection layer 200, and is 5% or more and 25% or less. If the porous diffusion layer 91 includes a plurality of faces (layers) with different porosities, the average porosity of the porous diffusion layer 91 is 5% or more and 25% or less, and is lower than the porosity of the leading end protection layer 200. The porous diffusion layer 91 is located at a position that is upstream of the measurement electrode 44 in the flow direction DR of the measurement target gas and where the distance to the measurement electrode 44 is 0.15 mm or less. A face (the area of a face) of the porous diffusion layer 91 that is orthogonal to the flow direction DR of the measurement target gas accounts for (blocks) 70% or more of a cross-section (the area of a cross-section) of the flow path CH of the measurement target gas that is orthogonal to the flow direction DR of the measurement target gas.

In this configuration, the porous diffusion layer 91, whose porosity is 5% or more and 25% or less and is lower than the porosity of the leading end protection layer 200, is located at a position that is upstream of the measurement electrode 44 in the flow direction DR of the measurement target gas and where the distance to the measurement electrode 44 is 0.15 mm or less. A face (the area of a face) of the porous diffusion layer 91 that is orthogonal to the flow direction DR of the measurement target gas accounts for (blocks) 70% or more of a cross-section (the area of a cross-section) of the flow path CH of the measurement target gas that is orthogonal to the flow direction DR of the measurement target gas. That is, the porous diffusion layer 91 is located at a position that is upstream of the measurement electrode 44 in the flow direction DR of the measurement target gas and where the distance to the measurement electrode 44 is 0.15 mm or less, and accounts for (blocks) a predetermined region (70% or more) of the flow path CH.

The above porous diffusion layer 91 can make the diffusion mode around the measurement electrode 44, i.e. the diffusion mode of the measurement target gas moving toward the measurement electrode 44 through the flow path CH a mode of diffusing while colliding with a wall face of a sufficiently narrow flow path, as in Knudsen diffusion. Thus, even if $H_2O$ gas is present in the measurement target gas, the gas sensor element 101 can reduce the impact of $H_2O$ gas on $NO_x$ gas (and $O_2$ gas) by means of the porous diffusion layer 91. Specifically, the gas sensor element 101 can suppress fluctuations in $NO_x$ output and the deterioration of the measurement electrode 44, which are considered to be caused by molecular diffusion of $NO_x$ under high $H_2O$ concentration, by means of the porous diffusion layer 91.

Here, if a porous diffusion layer 91 having large diffusion resistance is provided around the measurement electrode 44, there is a possibility that the porous diffusion layer 91 will be clogged with poisonous substances or the like. The gas sensor element 101 has the leading end protection layer 200 that covers at least the face of the element substrate 100 in which the gas inlet 10 is open. The gas sensor element 101 can thus trap poisonous substances or the like using the leading end protection layer 200, i.e. capture poisonous substances or the like using the leading end protection layer 200.

Particularly, in the gas sensor element 101, the porosity of the leading end protection layer 200 is larger (higher) than the porosity of the porous diffusion layer 91, which blocks a predetermined region of the flow path CH at a position where the distance to the measurement electrode 44 is 0.15 mm or less. The gas sensor element 101 can avoid a situation where the leading end protection layer 200 is clogged with poisonous substances or the like and the $NO_x$ output decreases, as a result of the porosity of the leading end protection layer 200 being larger than the porosity of the porous diffusion layer 91.

As described above, the gas sensor element 101 has the porous diffusion layer (e.g. the porous diffusion layer 91) around the measurement electrode 44, more specifically, upstream of the measurement electrode 44 in the flow direction DR of the measurement target gas. The area of a face of the porous diffusion layer that is orthogonal to the flow direction DR of the measurement target gas accounts for 70% or more of the area of a cross-section of the flow path CH of the measurement target gas that is orthogonal to the flow direction DR of the measurement target gas. The gas sensor element 101 can achieve the following effects by making the diffusion mode of the measurement target gas (particularly, $NO_x$ gas) moving toward the measurement electrode 44 a mode of diffusing while repeatedly colliding with a wall face of a sufficiently narrow flow path, as in Knudsen diffusion, by means of the porous diffusion layer. That is, even if $H_2O$ gas is present in the measurement target gas, the gas sensor element 101 can reduce the impact of the $H_2O$ gas on $NO_x$ gas (and $O_2$ gas) by means of the porous diffusion layer 91.

Here, it is more desirable that the position where the porous diffusion layer is located is closer to the measurement electrode 44, and the porous diffusion layer is located at least at a position where the distance d2 to the measurement electrode 44 is 0.15 mm or less. The porous diffusion layer that makes the diffusion mode around the measurement electrode 44 favorable may be in contact with the measurement electrode 44. The gas sensor element 101 can reduce the impact of $H_2O$ gas on $NO_x$ gas (and $O_2$ gas) by means of the porous diffusion layer located at a position that is upstream of the measurement electrode 44 and where the distance d2 to the measurement electrode 44 is 0.15 mm or less.

The flow path CH having a predetermined region blocked by the porous diffusion layer may have at least one face defined by the fourth diffusion control portion 18. The flow path CH may be configured, for example, as a slit between the second solid electrolyte layer 6 (e.g. the lower face thereof) and the fourth diffusion control portion 18 (e.g. the upper face thereof). However, it is not essential that the flow path having a predetermined region blocked by the porous diffusion layer has at least one face defined by the fourth diffusion control portion 18. The measurement target gas flow portion 7 may be the flow path having a predetermined region (specifically, 70% or more) of a cross-section orthogonal to the flow direction DR of the measurement target gas that is blocked by the porous diffusion layer.

The porous diffusion layer located at a position that is upstream of the measurement electrode 44 and where the distance d2 to the measurement electrode 44 is 0.15 mm or less may also extend downstream, particularly, to the internal cavity where the measurement electrode 44 is disposed. For example, the measurement electrode 44 may be disposed in the third internal cavity 19, and the porous diffusion layer (the porous diffusion layer 91A in the example shown in FIG. 5) disposed at the entrance of the flow path CH (the flow path CH constituted by the fourth diffusion control portion 18 in the example shown in FIG. 5) may extend to the third internal cavity 19.

The gas sensor according to one aspect of the present invention may measure the amount of a specific gas component in the measurement target gas, i.e. the concentration of a specific gas component, using the gas sensor element 101. This gas sensor changes the diffusion mode of $NO_x$ that reaches the measurement electrode 44 from molecular diffusion to a mode of diffusing while repeatedly colliding with a wall face of a sufficiently narrow flow path. Thus, the gas sensor suppresses fluctuations in NO$_x$ output and the deterioration of the measurement electrode 44, which are considered to be caused by molecular diffusion of NO$_x$ under high H$_2$O concentration, by means of any of the porous diffusion layers 91, 91A, 91C, 91D, 91E, and 91F.

Variations

Although an embodiment of the present invention has been described above, the description of the above embodiment is merely an illustration of the invention in all respects. Various improvements and variations may be made to the above embodiment. The constituent elements of the above embodiment may be omitted, replaced, and added as appropriate. The shape and dimensions of each constituent element of the above embodiment may be changed as appropriate, according to the mode of implementation. For example, the following changes are possible. Note that, in the following, the same constituent elements as those of the above embodiment are assigned the same reference numerals, and the description of the same features as the above embodiment is omitted as appropriate. The following variations can be combined as appropriate.

Variation 1

An example has been described where the measurement electrode 44 is provided on the lower face of the second solid electrolyte layer 6, but it is not essential for the gas sensor element 101 that the measurement electrode 44 is provided on the lower face of the second solid electrolyte layer 6. Further, in the above-described example, the porous diffusion layer 91 is provided between the fourth diffusion control portion 18 (particularly, the upper face thereof) and the second solid electrolyte layer 6 (particularly, the lower face thereof) such that the distance d2 to the measurement electrode 44 disposed on the lower face of the second solid electrolyte layer 6 is 0.15 mm or less. However, in the gas sensor element 101, the position where the porous diffusion layer 91 is disposed is not limited to being between the fourth diffusion control portion 18 (particularly, the upper face thereof) and the second solid electrolyte layer 6 (particularly, the lower face thereof).

The measurement electrode 44 may be provided on the upper face of the first solid electrolyte layer 4, for example. In this case, the porous diffusion layer 91 may be provided between the fourth diffusion control portion 18 (specifically, the lower face thereof) and the first solid electrolyte layer 4 (specifically, the upper face thereof) such that the distance d2 to the measurement electrode 44 is 0.15 mm or less. Alternatively, the measurement electrode 44 may be provided on a surface (upper or lower face) of the diffusion control portion (e.g. one of the fourth diffusion control portions 18D or one of the fourth diffusion control portions 18E), as described with reference to FIGS. 8 and 10 and other figures. In the gas sensor element 101, the position where the measurement electrode 44 is disposed can be selected as appropriate, according to the usage status or the like of the gas sensor element 101. The porous diffusion layer (e.g. the porous diffusion layer 91) that makes the diffusion mode around the measurement electrode 44 favorable need only be located at a position that is upstream of the measurement electrode 44 and where the distance to the measurement electrode 44 is 0.15 mm or less, according to the position where the measurement electrode 44 is disposed.

Variation 2

An example where the measurement electrode 44 is disposed in the third internal cavity 19 has been described above. However, it is not essential for the gas sensor element 101 that the measurement electrode 44 is disposed in the third internal cavity 19. It is not essential either that the gas sensor element 101 includes a plurality of internal cavities (e.g. two or three cavities), and the gas sensor element 101 may alternatively have a one-cavity structure, for example. That is, it is not essential for the gas sensor element 101 to include the diffusion control portion (at least one of the first diffusion control portion 11, the second diffusion control portion 13, the third diffusion control portion 16, and the fourth diffusion control portion 18). The gas sensor element 101 need only include the porous diffusion layer (e.g. the porous diffusion layer 91) that blocks the predetermined region of the flow path CH around the measurement electrode 44, and the leading end protection layer (either the leading end protection layer 200 or 200G) that covers at least the face of the element substrate 100 in which the gas inlet 10 is open. Whether the gas sensor element 101 has a one-cavity structure or a multi-cavity structure (a structure with two or more internal cavities) can be selected as appropriate, according to the usage status or the like of the gas sensor element 101. Similarly, the location of the measurement electrode 44 in the gas sensor element 101 can be selected as appropriate, according to the usage status or the like of the gas sensor element 101.

Examples

As described above, the gas sensor element 101 achieves the following effects as a result of including, for example, the porous diffusion layer 91 or the like that makes the diffusion mode of the measurement target gas moving toward the measurement electrode 44 desirable, and the leading end protection layer 200 or the like that covers at least the face of the element substrate 100 in which the gas inlet 10 is open. That is, the gas sensor element 101 can suppress the deterioration of the measurement electrode 44 in an environment with high H$_2$O concentration and improve the durability, by means of the porous diffusion layer 91. The gas sensor element 101 can, for example, prevent the porous diffusion layer 91 from being clogged with poisonous substances or the like and maintain the measurement accuracy over a long period of time, by means of the leading end protection layer 200.

The inventors produced gas sensors according to the following examples and comparative examples, and conducted various tests to verify the above-described effects. Note that the present invention is not limited to the following examples.

TABLE 1

| Criteria | Distance between measurement electrode and porous diffusion layer [mm] | Porosity of porous diffusion layer [%] | With/without leading end protection layer | Porosity of external leading end protection layer [%] | Porosity of internal leading end protection layer [%] | Shortest distance between leading end protection layer and gas inlet [mm] | Thickness of external leading end protection layer [um] |
|---|---|---|---|---|---|---|---|
| Example 1 | 0.1 | 12 | With | 20 | — | 300 | 300 |
| Example 2 | 0.05 | 8 | With | 20 | 60 | 1020 | 280 |
| Example 3 | 0.02 | 13 | With | 17 | 62 | 480 | 400 |
| Example 4 | 0.05 | 10 | With | 25 | 65 | 990 | 360 |

TABLE 1-continued

| | | | | | | | |
|---|---|---|---|---|---|---|---|
| Example 5 | 0.05 | 10 | With | 15 | 50 | 1050 | 200 |
| Example 6 | 0.1 | 15 | With | 23 | 55 | 500 | 350 |
| Example 7 | 0.13 | 20 | With | 30 | — | 200 | 200 |
| Example 8 | 0.1 | 25 | With | 15 | 45 | 900 | 300 |
| Example 9 | 0.15 | 10 | With | 20 | — | 300 | 300 |
| Comparative Example 1 | 0.1 | 10 | Without | — | — | — | — |
| Comparative Example 2 | — | — | With | 15 | — | 250 | 250 |
| Comparative Example 3 | 0.2 | 15 | With | 25 | — | 300 | 300 |
| Comparative Example 4 | 0.1 | 35 | With | 30 | — | 280 | 280 |
| Comparative Example 5 | 0.1 | 10 | With | 20 | — | 100 | 100 |

| Criteria | Thickness of internal leading end protection layer [um] | Proportion of internal leading end protection layer [%] | Evaluation 1 | Evaluation 2 | Evaluation 3 | Evaluation 4 |
|---|---|---|---|---|---|---|
| Example 1 | — | — | B | B | A | B |
| Example 2 | 740 | 73 | A | A | A | A |
| Example 3 | 80 | 17 | A | A | A | B |
| Example 4 | 630 | 64 | A | A | A | A |
| Example 5 | 850 | 81 | A | A | A | A |
| Example 6 | 150 | 30 | A | A | A | A |
| Example 7 | — | — | A | A | B | B |
| Example 8 | 600 | 67 | B | B | A | B |
| Example 9 | — | — | B | B | A | B |
| Comparative Example 1 | — | — | A | A | F | — |
| Comparative Example 2 | — | — | F | F | A | A |
| Comparative Example 3 | — | — | B | F | A | B |
| Comparative Example 4 | — | — | F | F | A | B |
| Comparative Example 5 | — | — | A | A | B | F |

Table 1 shows the configurations of each gas sensor element and the test results of evaluations 1 to 4 for gas sensors that include gas sensor elements according to examples 1 to 9 and comparative examples 1 to 5. In the following description, there are cases where the gas sensors that include the gas sensor elements according to the examples 1 to 9 and the comparative examples 1 to 5 are abbreviated as gas sensors ($NO_x$ sensors) according to the examples 1 to 9 and the comparative examples 1 to 5.

Details of Examples 1 to 9 and Comparative Examples 1 to 5

The example 1 is a gas sensor that includes the gas sensor element 101 that has the leading end protection layer 200 illustrated in FIG. 1 and the porous diffusion layer 91 illustrated in FIG. 3. Specifically, a space (gap) is present between the measurement electrode 44 and the porous diffusion layer 91, and the distance d2 therebetween is 0.1 mm, namely 0.15 mm or less. In the gas sensor according to the example 1, the porous diffusion layer 91 is a porous layer having a porosity that is constant at 5% or more and 25% or less throughout; specifically, the porosity of the porous diffusion layer 91 is 12%. The gas sensor according to the example 1 has the leading end protection layer 200 ('with' in the table), and the leading end protection layer 200 does not include the internal leading end protection layer 201, i.e. has a porosity that is constant throughout. Specifically, the porosity of the external leading end protection layer 202 (the leading end protection layer 200) is 20%, which is higher than the porosity of the porous diffusion layer 91. That is, in the gas sensor according to the example 1, the porosity (12%) of the porous diffusion layer 91 is lower than the porosity (20%) of the external leading end protection layer 202 (the leading end protection layer 200). Further, the shortest distance (d1) between the leading end protection layer 200 and the gas inlet 10, i.e. the distance d1 from the outermost face of the leading end protection layer 200 to the gas inlet is 300 μm, namely 200 μm (0.2 mm) or more. In the gas sensor according to the example 1, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 300 μm. The porosity of the internal leading end protection layer 201, the thickness of the internal leading end protection layer 201, and the thickness proportion of the internal leading end protection layer 201 are all '-' in the table.

The example 2 is a gas sensor that includes the gas sensor element 101 that has the leading end protection layer 200G illustrated in FIG. 12 and the porous diffusion layer 91 illustrated in FIG. 3. Specifically, a space (gap) is present between the measurement electrode 44 and the porous diffusion layer 91, and the distance d2 therebetween is 0.05 mm, namely 0.15 mm or less. In the gas sensor according to the example 2, the porous diffusion layer 91 is a porous layer having a porosity that is constant at 5% or more and 25% or less throughout; specifically, the porosity of the porous diffusion layer 91 is 8%. The gas sensor according to the example 2 has the leading end protection layer 200G ('with' in the table). Unlike the example 1, the leading end protection layer 200G includes the internal leading end protection layer 201. Specifically, the porosity of the external leading end protection layer 202 is 20%, which is higher than the porosity (8%) of the porous diffusion layer 91. That is, in the gas sensor according to the example 2, the porosity (8%) of the porous diffusion layer 91 is lower than the porosity (20%) of the external leading end protection layer 202. Further, the porosity of the internal leading end protection layer 201 included in the leading end protection layer 200G is 60%, which is higher than the porosity (8%) of the porous diffusion layer 91. That is, in the gas sensor according to the example 2, the porosity (8%) of the porous diffusion layer 91 is lower than the porosity (60%) of the internal leading end protection layer 201. The shortest distance (d1) between the leading end protection layer 200G and the gas inlet 10, i.e. the distance d1 from the outermost face of the leading end protection layer 200G to the gas inlet 10 is 1020 μm, namely 200 μm (0.2 mm) or more. The thickness of the external leading end protection layer 202 included in the leading end protection layer 200G is 280 μm, and the thickness of the internal leading end protection layer 201 included in the leading end protection layer 200G is 740 μm. Hence, the thickness proportion of the internal leading end protection layer 201, i.e. the proportion of the thickness of the internal leading end protection layer 201 to the thickness of the leading end protection layer 200G is 73%, namely 30% or more and 90% or less.

The example 3 is a gas sensor that includes the gas sensor element 101 that has the leading end protection layer 200G illustrated in FIG. 12 and the porous diffusion layer 91 illustrated in FIG. 3. Specifically, a space (gap) is present between the measurement electrode 44 and the porous diffusion layer 91, and the distance d2 therebetween is 0.02 mm, namely 0.15 mm or less. In the gas sensor according to the example 3, the porous diffusion layer 91 is a porous layer having a porosity that is constant at 5% or more and 25% or less throughout; specifically, the porosity of the porous diffusion layer 91 is 13%. The gas sensor according to the example 3 has the leading end protection layer 200G ('with' in the table). Unlike the example 1, the leading end protection layer 200G includes the internal leading end protection layer 201. Specifically, the porosity of the external leading end protection layer 202 is 17%, which is higher than the porosity of the porous diffusion layer 91. That is, in the gas sensor according to the example 3, the porosity (13%) of the porous diffusion layer 91 is lower than the porosity (17%) of the external leading end protection layer 202. Further, the porosity of the internal leading end protection layer 201 included in the leading end protection layer 200G is 62%, which is higher than the porosity (13%) of the porous diffusion layer 91. That is, in the gas sensor according to the example 3, the porosity (13%) of the porous diffusion layer 91 is lower than the porosity (62%) of the internal leading end protection layer 201. The shortest distance (d1) between the leading end protection layer 200G and the gas inlet 10, i.e. the distance d1 from the outermost face of the leading end protection layer 200G to the gas inlet 10 is 480 μm, namely 200 μm (0.2 mm) or more. The thickness of the external leading end protection layer 202 included in the leading end protection layer 200G is 400 μm, and the thickness of the internal leading end protection layer 201 included in the leading end protection layer 200G is 80 μm. Hence, the thickness proportion of the internal leading end protection layer 201, i.e. the proportion of the thickness of the internal leading end protection layer 201 to the thickness of the leading end protection layer 200G is 17%, namely less than 30%, unlike the example 2.

The example 4 is a gas sensor that includes the gas sensor element 101 that has the leading end protection layer 200G illustrated in FIG. 12 and the porous diffusion layer 91 illustrated in FIG. 3. Specifically, a space (gap) is present between the measurement electrode 44 and the porous diffusion layer 91, and the distance d2 therebetween is 0.05 mm, namely 0.15 mm or less. In the gas sensor according to the example 4, the porous diffusion layer 91 is a porous layer having a porosity that is constant at 5% or more and 25% or less throughout; specifically, the porosity of the porous diffusion layer 91 is 10%. The gas sensor according to the example 4 has the leading end protection layer 200G ('with' in the table). Unlike the example 1, the leading end protection layer 200G includes the internal leading end protection layer 201. Specifically, the porosity of the external leading end protection layer 202 is 25%, which is higher than the porosity of the porous diffusion layer 91. That is, in the gas sensor according to the example 4, the porosity (10%) of the porous diffusion layer 91 is lower than the porosity (25%) of the external leading end protection layer 202. Further, the porosity of the internal leading end protection layer 201 included in the leading end protection layer 200G is 65%, which is higher than the porosity (10%) of the porous diffusion layer 91. That is, in the gas sensor according to the example 4, the porosity (10%) of the porous diffusion layer 91 is lower than the porosity (65%) of the internal leading end protection layer 201. The shortest distance (d1) between the leading end protection layer 200G and the gas inlet 10, i.e. the distance d1 from the outermost face of the leading end protection layer 200G to the gas inlet 10 is 990 μm, namely 200 μm (0.2 mm) or more. The thickness of the external leading end protection layer 202 included in the leading end protection layer 200G is 360 μm, and the thickness of the internal leading end protection layer 201 included in the leading end protection layer 200G is 630 μm. Hence, the thickness proportion of the internal leading end protection layer 201, i.e. the proportion of the thickness of the internal leading end protection layer 201 to the thickness of the leading end protection layer 200G is 64%, namely 30% or more and 90% or less.

The example 5 is a gas sensor that includes the gas sensor element 101 that has the leading end protection layer 200G illustrated in FIG. 12 and the porous diffusion layer 91 illustrated in FIG. 3. Specifically, a space (gap) is present between the measurement electrode 44 and the porous diffusion layer 91, and the distance d2 therebetween is 0.05 mm, namely 0.15 mm or less. In the gas sensor according to the example 5, the porous diffusion layer 91 is a porous layer having a porosity that is constant at 5% or more and 25% or less throughout; specifically, the porosity of the porous diffusion layer 91 is 10%. The gas sensor according to the example 5 has the leading end protection layer 200G ('with' in the table). Unlike the example 1, the leading end protection layer 200G includes the internal leading end protection layer 201. Specifically, the porosity of the external leading end protection layer 202 is 15%, which is higher than the porosity of the porous diffusion layer 91. That is, in the gas sensor according to the example 5, the porosity (10%) of the porous diffusion layer 91 is lower than the porosity (15%) of the external leading end protection layer 202. Further, the porosity of the internal leading end protection layer 201 included in the leading end protection layer 200G is 50%, which is higher than the porosity (10%) of the porous diffusion layer 91. That is, in the gas sensor according to the example 5, the porosity (10%) of the porous diffusion layer 91 is lower than the porosity (50%) of the internal leading end protection layer 201. The shortest distance (d1) between the leading end protection layer 200G and the gas inlet 10, i.e. the distance d1 from the outermost face of the leading end protection layer 200G to the gas inlet 10 is 1050 μm, namely 200 μm (0.2 mm) or more. The thickness of the external leading end protection layer 202 included in the leading end protection layer 200G is 200 μm, and the thickness of the internal leading end protection layer 201 included in the leading end protection layer 200G is 850 μm. Hence, the thickness proportion of the internal leading end protection layer 201, i.e. the proportion of the thickness of the internal leading end protection layer 201 to the thickness of the leading end protection layer 200G is 81%, namely 30% or more and 90% or less.

The example 6 is a gas sensor that includes the gas sensor element 101 that has the leading end protection layer 200G illustrated in FIG. 12 and the porous diffusion layer 91 illustrated in FIG. 3. Specifically, a space (gap) is present between the measurement electrode 44 and the porous diffusion layer 91, and the distance d2 therebetween is 0.1 mm, namely 0.15 mm or less. In the gas sensor according to the example 6, the porous diffusion layer 91 is a porous layer having a porosity that is constant at 5% or more and 25% or less throughout; specifically, the porosity of the porous diffusion layer 91 is 15%. The gas sensor according to the example 6 has the leading end protection layer 200G ('with' in the table). Unlike the example 1, the leading end protection layer 200G includes the internal leading end protection layer 201. Specifically, the porosity of the external leading end protection layer 202 is 23%, which is higher than the porosity of the porous diffusion layer 91. That is, in the gas sensor according to the example 6, the porosity (15%) of the porous diffusion layer 91 is lower than the porosity (23%) of the external leading end protection layer 202. Further, the porosity of the internal leading end protection layer 201 included in the leading end protection layer 200G is 55%, which is higher than the porosity (15%) of the porous diffusion layer 91. That is, in the gas sensor according to the example 6, the porosity (15%) of the porous diffusion layer 91 is lower than the porosity (55%) of the internal leading end protection layer 201. The shortest distance (d1) between the leading end protection layer 200G and the gas inlet 10, i.e. the distance d1 from the outermost face of the leading end protection layer 200G to the gas inlet 10 is 500 μm, namely 200 μm (0.2 mm) or more. The thickness of the external leading end protection layer 202 included in the leading end protection layer 200G is 350 μm, and the thickness of the internal leading end protection layer 201 included in the leading end protection layer 200G is 150 μm. That is, unlike the examples 2, 4, and 5, the thickness (150 μm) of the internal leading end protection layer 201 is smaller than the thickness (350 μm) of the external leading end protection layer 202 in the example 6. However, in the example 6, the thickness proportion of the internal leading end protection layer 201, i.e. the proportion of the thickness of the internal leading end protection layer 201 to the thickness of the leading end protection layer 200G is 30%, namely 30% or more and 90% or less, similarly to the examples 2, 4, and 5.

The example 7 is a gas sensor that includes the gas sensor element 101 that has the leading end protection layer 200 illustrated in FIG. 1 and the porous diffusion layer 91 illustrated in FIG. 3. Specifically, a space (gap) is present between the measurement electrode 44 and the porous diffusion layer 91, and the distance d2 therebetween is 0.13 mm, namely 0.15 mm or less. In the gas sensor according to the example 7, the porous diffusion layer 91 is a porous layer having a porosity that is constant at 5% or more and 25% or less throughout; specifically, the porosity of the porous diffusion layer 91 is 20%. The gas sensor according to the example 7 has the leading end protection layer 200 ('with' in the table). Meanwhile, unlike the examples 2 to 6, the leading end protection layer 200 according to the example 7 does not include the internal leading end protection layer 201, i.e. the porosity of the leading end protection layer 200 is constant throughout. Specifically, the porosity of the external leading end protection layer 202 (the leading end protection layer 200) is 30%, which is higher than the porosity of the porous diffusion layer 91. That is, in the gas sensor according to the example 7, the porosity (20%) of the porous diffusion layer 91 is lower than the porosity (30%) of the external leading end protection layer 202 (the leading end protection layer 200). Further, the shortest distance (d1) between the leading end protection layer 200 and the gas inlet 10, i.e. the distance d1 from the outermost face of the leading end protection layer 200 to the gas inlet 10 is 200 μm, namely 200 μm (0.2 mm) or more. In the gas sensor according to the example 7, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 200 μm. The porosity of the internal leading end protection layer 201, the thickness of the internal leading end protection layer 201, and the thickness proportion of the internal leading end protection layer 201 are all '-' in the table.

The example 8 is a gas sensor that includes the gas sensor element 101 that has the leading end protection layer 200G illustrated in FIG. 12 and the porous diffusion layer 91 illustrated in FIG. 3. Specifically, a space (gap) is present between the measurement electrode 44 and the porous diffusion layer 91, and the distance d2 therebetween is 0.1 mm, namely 0.15 mm or less. In the gas sensor according to the example 8, the porous diffusion layer 91 is a porous layer having a porosity that is constant at 5% or more and 25% or less throughout; specifically, the porosity of the porous diffusion layer 91 is 25%. The gas sensor according to the example 8 has the leading end protection layer 200G ('with' in the table). Unlike the example 1, the leading end protection layer 200G includes the internal leading end protection layer 201. Specifically, the porosity of the external leading end protection layer 202 is 15%, which is lower than the porosity of the porous diffusion layer 91. That is, in the gas sensor according to the example 8, the porosity (25%) of the porous diffusion layer 91 is higher than the porosity (15%) of the external leading end protection layer 202, unlike the examples 1 to 7. Meanwhile, the porosity of the internal leading end protection layer 201 included in the leading end protection layer 200G is 45%, which is higher than the porosity (25%) of the porous diffusion layer 91. That is, in the gas sensor according to the example 8, the porosity (25%) of the porous diffusion layer 91 is lower than the porosity (45%) of the internal leading end protection layer 201. The shortest distance (d1) between the leading end protection layer 200G and the gas inlet 10, i.e. the distance d1 from the outermost face of the leading end protection layer 200G to the gas inlet 10 is 900 μm, namely 200 μm (0.2 mm) or more. The thickness of the external leading end protection layer 202 included in the leading end protection layer 200G is 300 μm, and the thickness of the internal leading end protection layer 201 included in the leading end protection layer 200G is 600 μm. Hence, the thickness proportion of the internal leading end protection layer 201, i.e. the proportion of the thickness of the internal leading end protection layer 201 to the thickness of the leading end protection layer 200G is 67%, namely 30% or more and 90% or less.

The example 9 is a gas sensor that includes the gas sensor element 101 that has the leading end protection layer 200 illustrated in FIG. 1 and the porous diffusion layer 91 illustrated in FIG. 3. Specifically, a space (gap) is present between the measurement electrode 44 and the porous diffusion layer 91, and the distance d2 therebetween is 0.15 mm, namely 0.15 mm or less. In the gas sensor according to the example 9, the porous diffusion layer 91 is a porous layer having a porosity that is constant at 5% or more and 25% or less throughout; specifically, the porosity of the porous diffusion layer 91 is 10%. The gas sensor according to the example 9 has the leading end protection layer 200 ('with' in the table). Meanwhile, unlike the examples 2 to 6 and 8, the leading end protection layer 200 according to the example 9 does not include the internal leading end protection layer 201, i.e. the porosity of the leading end protection layer 200 is constant throughout. Specifically, the porosity of the external leading end protection layer 202 (the leading end protection layer 200) is 20%, which is higher than the porosity of the porous diffusion layer 91. That is, in the gas sensor according to the example 9, the porosity (10%) of the porous diffusion layer 91 is lower than the porosity (20%) of the external leading end protection layer 202 (the leading end protection layer 200). Further, the shortest distance (d1) between the leading end protection layer 200 and the gas inlet 10, i.e. the distance d1 from the outermost face of the leading end protection layer 200 to the gas inlet 10 is 300 μm, namely 200 μm (0.2 mm) or more. In the gas sensor according to the example 9, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 300 μm. The porosity of the internal leading end protection layer 201, the thickness of the internal leading end protection layer 201, and the thickness proportion of the internal leading end protection layer 201 are all '-' in the table.

The comparative example 1 is a gas sensor that includes a sensor element with the same structure as the example 1, except that the sensor element does not include the leading end protection layer 200. Specifically, in the comparative example 1, a space (gap) is present between the measurement electrode 44 and the porous diffusion layer 91, and the distance d2 therebetween is 0.1 mm, namely 0.15 mm or less. In the gas sensor according to the comparative example 1, the porous diffusion layer 91 is a porous layer having a porosity that is constant at 5% or more and 25% or less throughout; specifically, the porosity of the porous diffusion layer 91 is 10%. The gas sensor according to the comparative example 1 does not include the leading end protection layer 200 ('without' in the table) as mentioned above, and the porosity of the external leading end protection layer 202 and the porosity of the internal leading end protection layer 201 are both '-' in the table. Also, the shortest distance between the leading end protection layer 200 and the gas inlet 10, the thickness of the external leading end protection layer 202, the thickness of the internal leading end protection layer 201, and the thickness proportion of the internal leading end protection layer 201 are all '-' in the table.

The comparative example 2 is a gas sensor that includes a sensor element that does not have the porous diffusion layer (e.g. the porous diffusion layer 91) for making the diffusion mode around the measurement electrode 44 favorable, but only includes the leading end protection layer 200 illustrated in FIG. 1. The comparative example 2 does not include the porous diffusion layer, and accordingly, the distance between the measurement electrode 44 and the porous diffusion layer and the porosity of the porous diffusion layer are both '-' in the table. The gas sensor according to the comparative example 2 includes the leading end protection layer 200 ('with' in the table). Meanwhile, unlike the examples 2 to 6 and 8, the leading end protection layer 200 according to the comparative example 2 does not include the internal leading end protection layer 201, i.e. the porosity of the leading end protection layer 200 is constant throughout. Specifically, the porosity of the external leading end protection layer 202 (the leading end protection layer 200) is 15%. Further, the shortest distance (d1) between the leading end protection layer 200 and the gas inlet 10, i.e. the distance d1 from the outermost face of the leading end protection layer 200 to the gas inlet 10 is 250 μm, namely 200 μm (0.2 mm) or more. In the gas sensor according to the comparative example 2, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 250 μm. The porosity of the internal leading end protection layer 201, the thickness of the internal leading end protection layer 201, and the thickness proportion of the internal leading end protection layer 201 are all '-' in the table.

The comparative example 3 is a gas sensor that includes a sensor element with the same structure as the example 1, except that the distance d2 between the measurement electrode 44 and the porous diffusion layer 91 is larger than 0.15 mm. Specifically, in the comparative example 3, a space (gap) is present between the measurement electrode 44 and the porous diffusion layer 91, and the distance d2 therebetween is 0.2 mm, namely larger than 0.15 mm, unlike the example 1. In the gas sensor according to the comparative example 3, the porous diffusion layer 91 is a porous layer having a porosity that is constant at 5% or more and 25% or less throughout; specifically, the porosity of the porous diffusion layer 91 is 15%. The gas sensor according to the comparative example 3 includes the leading end protection layer 200 ('with' in the table). Meanwhile, unlike the examples 2 to 6 and 8, the leading end protection layer 200 according to the comparative example 3 does not include the internal leading end protection layer 201, i.e. the porosity of the leading end protection layer 200 is constant throughout. Specifically, the porosity of the external leading end protection layer 202 (the leading end protection layer 200) is 25%, which is higher than the porosity of the porous diffusion layer 91. That is, in the gas sensor according to the comparative example 3, the porosity (15%) of the porous diffusion layer 91 is lower than the porosity (25%) of the external leading end protection layer 202 (the leading end protection layer 200). Further, the shortest distance (d1) between the leading end protection layer 200 and the gas inlet 10, i.e. the distance d1 from the outermost face of the leading end protection layer 200 to the gas inlet 10 is 300 μm, namely 200 μm (0.2 mm) or more. In the gas sensor according to the comparative example 3, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 300 μm. The porosity of the internal leading end protection layer 201, the thickness of the internal leading end protection layer 201, and the thickness proportion of the internal leading end protection layer 201 are all '-' in the table.

The comparative example 4 is a gas sensor that includes a sensor element with the same structure as the example 1, except that the porosity of the porous diffusion layer 91 is larger than 25%, and that the porosity of the porous diffusion layer 91 is higher than the porosity of the external leading end protection layer 202 (the leading end protection layer 200). Specifically, a space (gap) is present between the measurement electrode 44 and the porous diffusion layer 91, and the distance d2 therebetween is 0.1 mm, namely 0.15 mm or less. In the gas sensor according to the comparative example 4, the porous diffusion layer 91 is a porous layer having a porosity that is constant throughout. Meanwhile, the porosity of the porous diffusion layer 91 according to the comparative example 4 is 35%, namely larger than 25%, unlike the example 1. The gas sensor according to the comparative example 4 includes the leading end protection layer 200 ('with' in the table). Meanwhile, unlike the examples 2 to 6 and 8, the leading end protection layer 200 according to the comparative example 4 does not include the internal leading end protection layer 201, i.e. the porosity of the leading end protection layer 200 is constant throughout. Specifically, the porosity of the external leading end protection layer 202 (the leading end protection layer 200) is 30%, which is lower than the porosity of the porous diffusion layer 91. That is, in the gas sensor according to the comparative example 4, the porosity (35%) of the porous diffusion layer 91 is higher than the porosity (30%) of the external leading end protection layer 202 (the leading end protection layer 200), unlike the example 1. Further, the shortest distance (d1) between the leading end protection layer 200 and the gas inlet 10, i.e. the distance d1 from the outermost face of the leading end protection layer 200 to the gas inlet 10 is 280 μm, namely 200 μm (0.2 mm) or more. In the gas sensor according to the comparative example 4, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 280 μm. The porosity of the internal leading end protection layer 201, the thickness of the internal leading end protection layer 201, and the thickness proportion of the internal leading end protection layer 201 are all '-' in the table.

The comparative example 5 is a gas sensor that includes a sensor element with the same structure as the example 1, except that the shortest distance (d1) between the leading end protection layer 200 and the gas inlet 10 is smaller than 0.2 mm (200 μm). Specifically, a space (gap) is present between the measurement electrode 44 and the porous diffusion layer 91, and the distance d2 therebetween is 0.1 mm, namely 0.15 mm or less. In the gas sensor according to the comparative example 5, the porous diffusion layer 91 is a porous layer having a porosity that is constant at 5% or more and 25% or less throughout; specifically, the porosity of the porous diffusion layer 91 is 10%. The gas sensor according to the comparative example 5 has the leading end protection layer 200 ('with' in the table), and the leading end protection layer 200 does not include the internal leading end protection layer 201, i.e. has a porosity that is constant throughout. Specifically, the porosity of the external leading end protection layer 202 (the leading end protection layer 200) is 20%, which is higher than the porosity of the porous diffusion layer 91. That is, in the gas sensor according to the comparative example 5, the porosity (10%) of the porous diffusion layer 91 is lower than the porosity (20%) of the external leading end protection layer 202 (the leading end protection layer 200). Meanwhile, in the gas sensor according to the comparative example 5, the shortest distance (d1) between the leading end protection layer 200 and the gas inlet 10, i.e. the distance d1 from the outermost face of the leading end protection layer 200 to the gas inlet 10 is smaller than 0.2 mm (200 μm), unlike the example 1. Specifically, the shortest distance (d1) between the leading end protection layer 200 and the gas inlet 10 is 100 μm, namely smaller than 0.2 mm (200 μm). In the gas sensor according to the comparative example 5, the leading end protection layer 200 does not include the internal leading end protection layer 201, as mentioned above. Thus, the thickness of the external leading end protection layer 202 is the same as the distance d1 from the outermost face of the leading end protection layer 200 to the gas inlet 10, namely 100 μm. The porosity of the internal leading end protection layer 201, the thickness of the internal leading end protection layer 201, and the thickness proportion of the internal leading end protection layer 201 are all '-' in the table.

Details of Evaluations 1 to 4

The evaluation 1 is for verifying the effect of suppressing the deterioration of the measurement electrode caused by high $H_2O$ concentration. Specifically, first, an environment with a $H_2O$ concentration=25% and an $O_2$ concentration=20.5% was prepared. A 2000-hour long-term durability test was conducted in this environment on the $NO_x$ sensors according to the examples 1 to 9 and the comparative examples 1 to 5. The inventors conducted the long-term durability test under the following accelerated deterioration test conditions in order to determine the degree of deterioration of properties (deterioration of the measurement electrode caused by high $H_2O$ concentration) in the case where the $NO_x$ sensors according to the examples 1 to 9 and the comparative examples 1 to 5 were continuously used for a long period of time. That is, the inventors conducted the long-term durability test under accelerated deterioration test conditions in which the heating temperature of the heat generating unit 72 was a predetermined temperature (100 degrees Celsius in the long-term durability test) higher than the sensor element drive temperature. The sensor element drive temperature is the heating temperature of the heat generating unit 72 when each $NO_x$ sensor is used (actually used), and can be considered as the heating temperature when the gas sensor element 101 is driven. An evaluation was conducted using a model gas to investigate the degree of change in $NO_x$ output when $NO_x$=500 ppm flowed, before and after the test. The symbol 'A' indicates that the $NO_x$ sensitivity change rate was within plus or minus 10%. The symbol 'B' indicates that the $NO_x$ sensitivity change rate was larger than plus or minus 10% and within 20%. The symbol 'F' indicates that the $NO_x$ sensitivity change rate was larger than plus or minus 20%.

The evaluation 2 is for verifying the effect of reducing $H_2O$ dependence and increasing the measurement accuracy while the $NO_x$ gas is flowing. Specifically, the following verification (investigation) was carried out. That is, after the test for the evaluation 1, the degree of change in $NO_x$ output was investigated when the $NO_x$ concentration was changed to 500 ppm and the $H_2O$ concentration was changed 15%, with a $NO_x$ concentration=500 ppm and a $H_2O$ concentration=3% as a base, for the $NO_x$ sensors according to the examples 1 to 9 and the comparative examples 1 to 5. The symbol 'A' indicates that the change rate (degree of change)

in the $NO_x$ sensitivity from when a $H_2O$ concentration=3% to when a $H_2O$ concentration=15% was within plus or minus 5%. The symbol 'B' indicates that the change rate of the $NO_x$ sensitivity from when a $H_2O$ concentration=3% to when a $H_2O$ concentration=15% was within plus or minus 10%. The symbol 'F' indicates that the change rate of the $NO_x$ sensitivity from when a $H_2O$ concentration=3% to when a $H_2O$ concentration=15% was larger than plus or minus 10%.

The evaluation 3 is for verifying the effect of trapping a poisonous substance and preventing clogging around the measurement electrode (e.g. the porous diffusion layer) that is achieved by the leading end protection layer, and the following Mg poisoning test was conducted on the $NO_x$ sensors according to the examples 1 to 9 and the comparative examples 1 to 5. That is, a cycle of dropping 10 μL of Mg ion solution with a Mg ion concentration of 5 mmol/L onto the $NO_x$ sensors, leaving these $NO_x$ sensors to stand for 1 minute, and then driving each gas sensor at 800 degrees Celsius for 10 minutes was repeated 10 times. Thus, a total of 100 μL of the Mg ion solution was dropped. The degree of change (change rate) in $NO_x$ output before and after the test was then investigated. Specifically, first, the $NO_x$ sensitivity was measured in a $NO_x$ model gas with a $NO_x$ concentration=500 ppm using each of the $NO_x$ sensors according to the examples 1 to 9 and the comparative examples 1 to 5, and the measured sensitivity was used as an initial $NO_x$ sensitivity. Then, a cycle of dropping 10 μL of the aforementioned Mg ion solution into the gas inlet of each $NO_x$ sensor, leaving the gas sensor to stand for 1 minute, and then driving the gas sensor at 800 degrees Celsius for 10 minutes was repeated 10 times. Thus, a total of 100 μL of the Mg ion solution was dropped. Then, the $NO_x$ sensitivity was measured again in the aforementioned $NO_x$ model gas using each $NO_x$ sensor, and a sensitivity decrease rate was calculated by comparing the measured $NO_x$ sensitivity with the initial $NO_x$ sensitivity. The symbol 'A' indicates that the $NO_x$ sensitivity change rate was within plus or minus 10%. The symbol 'B' indicates that the $NO_x$ sensitivity change rate was larger than plus or minus 20% and within 30%. The symbol 'F' indicates that the $NO_x$ sensitivity change rate was larger than 30%.

The evaluation 4 is, like the evaluation 3, for verifying the effect of reducing clogging around the measurement electrode that is achieved by the leading end protection layer, while the effect is verified under more severe conditions than with the method used in the evaluation 3. Specifically, the likelihood of clogging of the leading end protection layer was increased. That is, in the evaluation 4, the same Mg poisoning test as in the evaluation 3 was conducted, except that the total amount of Mg ion solution dropped was 500 μL. The degree of change (change rate) in $NO_x$ output before and after the test was then investigated, i.e. the degree of change in $NO_x$ output when $NO_x$ model gas with a $NO_x$ concentration=500 ppm flowed was investigated. The symbol 'A' indicates that the $NO_x$ sensitivity change rate was within plus or minus 10%. The symbol 'B' indicates that the $NO_x$ sensitivity change rate was larger than plus or minus 20% and within 30%. The symbol 'F' indicates that the $NO_x$ sensitivity change rate was larger than plus or minus 30%.

Summary of Facts Confirmed from Table 1

The following is a summary of the facts that can be confirmed from Table 1 that shows the test results of the evaluations 1 to 4 for the gas sensors that include the sensor elements according to the examples 1 to 9 and the comparative examples 1 to 5.

As indicated by the results of comparing the examples 1 to 9 with the comparative example 1 in the evaluation 3 (and the evaluation 4), the gas sensor can achieve the following effects as a result of including the leading end protection layer 200 (or the leading end protection layer 200G). That is, the results (A or B) of the evaluation 3 for the examples 1 to 9 with the leading end protection layer 200 or the leading end protection layer 200G are all better than the result (F) of the evaluation 3 for the comparative example 1 without the leading end protection layer 200 or the leading end protection layer 200G. Accordingly, it was confirmed that the gas sensor can trap the poisonous substance and prevent clogging around the measurement electrode 44 (e.g. the porous diffusion layer 91) as a result of including the leading end protection layer 200 (or the leading end protection layer 200G).

As indicated by the results of comparing the examples 1 to 9 with the comparative example 2 in the evaluation 1 and the evaluation 2, it was confirmed that the gas sensor can achieve the following effects as a result of including the porous diffusion layer (e.g. the porous diffusion layer 91) that makes the diffusion mode around the measurement electrode 44 favorable. That is, the results (A or B) of the evaluation 1 for the examples 1 to 9 with the porous diffusion layer 91 or the like are better than the result (F) of the evaluation 1 for the comparative example 2 without the porous diffusion layer 91 or the like. Accordingly, it was confirmed that the gas sensor can suppress the deterioration of the measurement electrode (particularly, deterioration of the measurement electrode caused by high $H_2O$ concentration) as a result of including the porous diffusion layer (e.g. the porous diffusion layer 91) that makes the diffusion mode around the measurement electrode 44 favorable (evaluation 1). Further, the results (A or B) of the evaluation 2 for the examples 1 to 9 with the porous diffusion layer 91 or the like are all better than the result (F) of the evaluation 2 for the comparative example 2 without the porous diffusion layer 91 or the like. Accordingly, it was confirmed that the gas sensor can reduce $H_2O$ dependence of $NO_x$ sensitivity ($NO_x$ output) and increase the measurement accuracy (evaluation 2) as a result of including the porous diffusion layer (e.g. the porous diffusion layer 91) that makes the diffusion mode around the measurement electrode 44 favorable.

The results of the evaluation 2 significantly differ between the example 1 and the comparative example 3, depending on whether or not the distance d2 from the porous diffusion layer (e.g. the porous diffusion layer 91) that makes the diffusion mode around the measurement electrode 44 favorable to the measurement electrode 44 is 0.15 mm or less. Specifically, the result of the evaluation 2 for the example 1 where the distance d2 is 0.1 mm (0.15 mm or less) is B, whereas the result of the evaluation 2 for the comparative example 3 where the distance d2 is 0.2 mm (larger than 0.15 mm) is F. Therefore, it was confirmed that the gas sensor can achieve the following effects as a result of the distance d2 from the porous diffusion layer (e.g. the porous diffusion layer 91) that makes the diffusion mode around the measurement electrode 44 favorable to the measurement electrode 44 being 0.15 mm or less. That is, it was confirmed that the gas sensor can reduce $H_2O$ dependence of the $NO_x$ sensitivity ($NO_x$ output) and increase the measurement accuracy as a result of the distance d2 from the porous diffusion layer to the measurement electrode 44 being 0.15 mm or less.

The results of the evaluations 1 and 2 significantly differ between the example 1 and the comparative example 4, depending on whether or not the porosity of the porous diffusion layer (e.g. the porous diffusion layer 91), which is separated from the measurement electrode 44 by the distance d2 that is 0.15 mm or less, is 5% or more and 25% or less and is lower than the porosity of the leading end protection layer. Specifically, the results of the evaluations 1 and 2 for the example 1, which includes the porous diffusion layer 91 having a porosity that is 5% or more and 25% or less and is lower than the porosity of the leading end protection layer, are both B. In contrast, the results of the evaluations 1 and 2 for the comparative example 4, which includes the porous diffusion layer 91 having a porosity that is larger than 25% and higher than the porosity of the leading end protection layer, are both F. Accordingly, it was confirmed that the gas sensor can achieve the following effects as a result of the porosity of the porous diffusion layer (e.g. the porous diffusion layer 91), which is separated from the measurement electrode 44 by the distance d2 that is 0.15 mm or less, being 5% or more and 25% or less and being lower than the porosity of the leading end protection layer. That is, it was confirmed that the gas sensor suppressed the deterioration of the measurement electrode that is caused by high $H_2O$ concentration, as a result of the porosity of the porous diffusion layer being 5% or more and 25% or less and being lower than the porosity of the leading end protection layer (evaluation 1). It was also confirmed that the gas sensor reduced the $H_2O$ dependence of $NO_x$ sensitivity ($NO_x$ output) and increased the measurement accuracy as a result of the porosity of the porous diffusion layer being 5% or more and 25% or less and being lower than the porosity of the leading end protection layer (evaluation 2).

Note that the porosity of the porous diffusion layer 91 in the example 8 is 5% or more and 25% or less, but is higher than the porosity of the external leading end protection layer 202, unlike the examples 1 to 7. Further, the results of the evaluation 2 for the examples 2 to 7 are all A, while the result of the evaluation 2 for the example 8 is B. However, in the example 8, the porosity of the porous diffusion layer 91 is lower than the porosity of the internal leading end protection layer 201, i.e. lower than the porosity of the internal leading end protection layer 201 that is in contact with the face of the element substrate 100 in which the gas inlet 10 is open. In contrast, in the comparative example 4, the leading end protection layer 200 does not include the internal leading end protection layer 201, and the porosity of the porous diffusion layer 91 is larger than 25% and higher than the porosity of the leading end protection layer 200. The result of the evaluation 2 for the comparative example 4 is F. Therefore, it can be considered that the following effects can be achieved as a result of the porosity of the porous diffusion layer 91 being 5% or more and 25% or less and being at least lower than the porosity of the internal leading end protection layer 201 that is in contact with the face of the element substrate 100 in which the gas inlet 10 is open. In other words, it can be considered that $H_2O$ dependence of the $NO_x$ sensitivity ($NO_x$ output) can be reduced, and the measurement accuracy can be increased.

The results of the evaluations 3 and 4 differ between the example 1 and the comparative example 5, depending on whether or not the distance d1 from the outermost face of the leading end protection layer 200 (or the leading end protection layer 200G) to the gas inlet 10 is 0.2 mm (200 μm) or more. Specifically, the results of the evaluations 3 and 4 for the example 1 with the leading end protection layer 200, whose outermost face is separated from the gas inlet 10 by the distance d1 that is 300 μm, namely 0.2 mm or more, are A and B, respectively. In contrast, the results of the evaluations 3 and 4 for the comparative example 5 with the leading end protection layer 200, whose the outermost face is separated from the gas inlet by the distance d1 that is 100

μm, namely smaller than 0.2 mm, are B and F, respectively. It was thus confirmed that the gas sensor can achieve the following effects as a result of the distance d1 being 0.2 mm or more. In other words, it was confirmed that the gas sensor can the trap poisonous substances and prevent clogging around the measurement electrode (e.g. the porous diffusion layer) as a result of the distance d1 being 0.2 mm or more (evaluation 3). Furthermore, it was confirmed that the gas sensor can trap the poisonous substances and prevent clogging around the measurement electrode even in a harsh environment with a large amount of poisonous substances or the like where the leading end protection layer could be clogged, as a result of the distance d1 being 0.2 mm or more (evaluation 4).

Comparing the example 1 with the examples 2 and 4 to 6, the examples 2 and 4 to 6 exhibited better results of the evaluations 1, 2, and 4 than the example 1. Further, comparing the example 7 with the examples 2 and 4 to 6, the examples 2 and 4 to 6 exhibited better results of the evaluations 3 and 4 than the example 7. Moreover, the results of the evaluation 4 for the examples 2 and 4 to 6 were all A, while the result of the evaluation 4 for the example 3 was B. Here, as mentioned above, the examples 2 and 4 to 6 have the following configuration, unlike the examples 1 and 7. That is, the gas sensors of the examples 2 and 4 to 6 have the leading end protection layer 200G that includes the external leading end protection layer 202 and the internal leading end protection layer 201 having a porosity larger than the porosity of the external leading end protection layer 202, and the thickness of the internal leading end protection layer 201 is 30% or more and 90% or less of the thickness of the leading end protection layer 200G. Further, in the example 3, the thickness proportion of the internal leading end protection layer 201 is less than 30%, unlike the examples 2 and 4 to 6. It was thus confirmed that the gas sensor can realize at least the following effects related to the evaluation 4 as a result of including the leading end protection layer 200G and having the internal leading end protection layer 201 whose thickness is 30% or more and 90% or less of the thickness of the leading end protection layer 200G. That is, it was confirmed that the gas sensor can trap poisonous substances and prevent clogging around the measurement electrode (e.g. the porous diffusion layer) even in a harsh environment with a large amount of poisonous substances or the like where the leading end protection layer itself could be clogged.

$NO_x$ Sensitivity Change Rate

Figure 13:
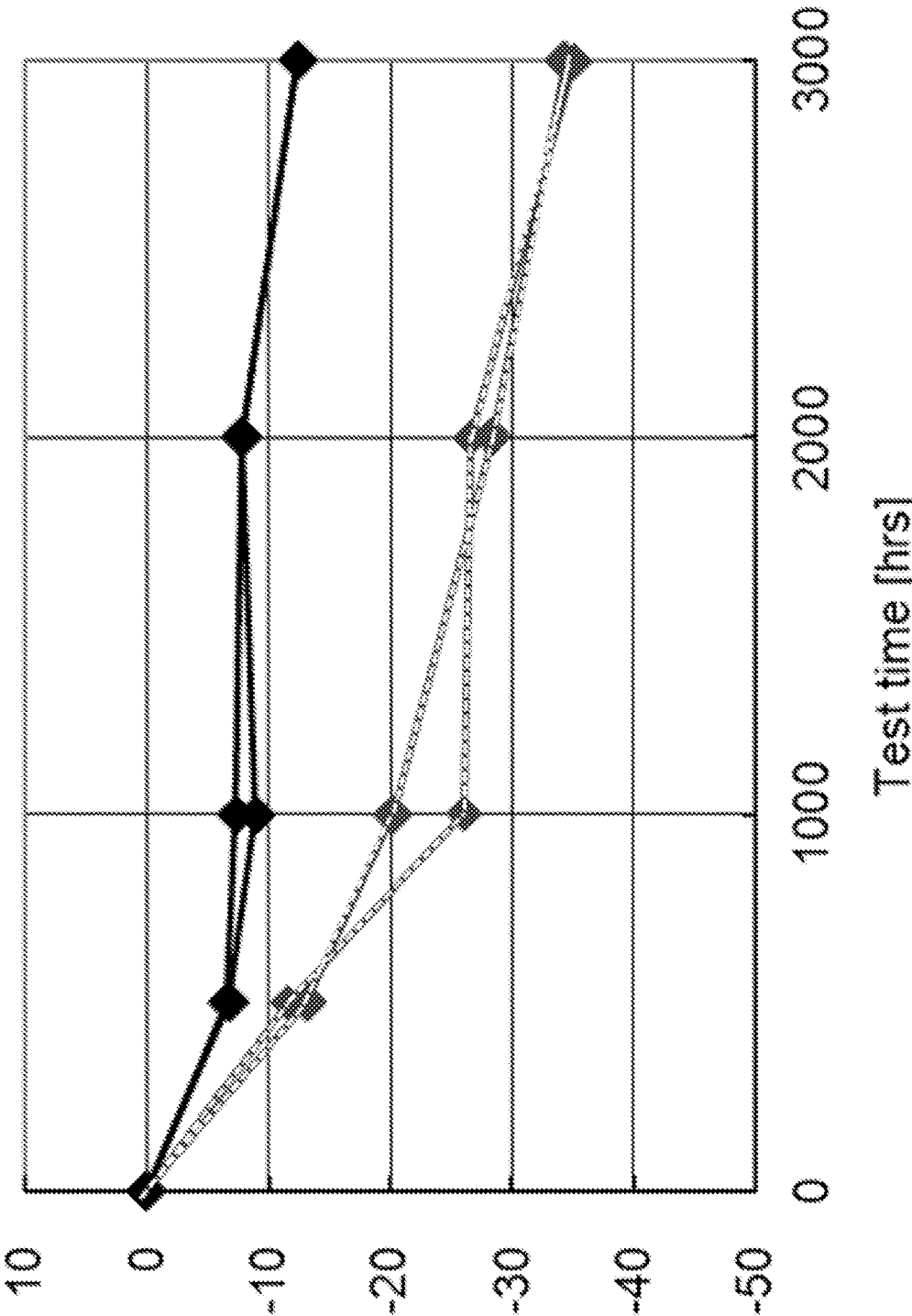
FIG. 13 is a graph showing differences in change in $NO_x$ output over time with and without a porous diffusion layer that blocks the predetermined region of the flow path CH around a measurement electrode.

FIG. 13 is a graph showing differences in the change over time in $NO_x$ output with and without the porous diffusion layer that blocks the predetermined region of the flow path CH around the measurement electrode. Specifically, FIG. 13 shows the change over time in $NO_x$ output of each $NO_x$ sensor under high $H_2O$ concentration regarding $NO_x$ sensors with the same structure, except for the presence of the porous diffusion layer (any of the porous diffusion layers 91, 91A, 91C, 91D, 91E, and 91F) that blocks the predetermined region of the flow path CH around the measurement electrode 44. The term "under high $H_2O$ concentration" refers to a $H_2O$ concentration=25%, for example. In the graph in FIG. 13, the horizontal axis indicates time (drive time), and the vertical axis indicates the $NO_x$ sensitivity change rate. Solid black lines indicate the change over time in $NO_x$ output of the $NO_x$ sensors that include the porous diffusion layer that blocks the predetermined region of the flow path CH around the measurement electrode 44. Dotted lines indicate the change over time in $NO_x$ output of the $NO_x$ sensors that do not include the porous diffusion layer that blocks the predetermined region of the flow path CH around the measurement electrode 44 (specifically, conventional $NO_x$ sensors that merely have a slit structure using a diffusion control portion).

Specifically, an $NO_x$ current (pump current Ip2) was measured for the aforementioned $NO_x$ sensors in a model gas atmosphere with a $NO_x$ concentration=500 ppm and the remainder being nitrogen, using a model gas apparatus. The graph shown in FIG. 13 was created by plotting the $NO_x$ sensitivity ($NO_x$ sensitivity change rate) calculated from the measurement results at each driving time.

As shown in FIG. 13, the $NO_x$ sensitivity significantly varies during the long-term drive test under high $H_2O$ concentration in the $NO_x$ sensors that do not have the porous diffusion layer around the measurement electrode 44 (conventional $NO_x$ sensors that merely have a slit structure using a diffusion control portion). This is possibly because molecular diffusion is a dominant diffusion mode around the measurement electrode 44 in the conventional slit structure using a diffusion control portion. In contrast, the $NO_x$ sensors that include the porous diffusion layer can suppress fluctuations (change over time) in the $NO_x$ sensitivity even under high $H_2O$ concentration by making the diffusion mode around the measurement electrode 44 a favorable diffusion mode, such as Knudsen diffusion.

$H_2O$ Dependence of $NO_x$ Output

Figure 14:
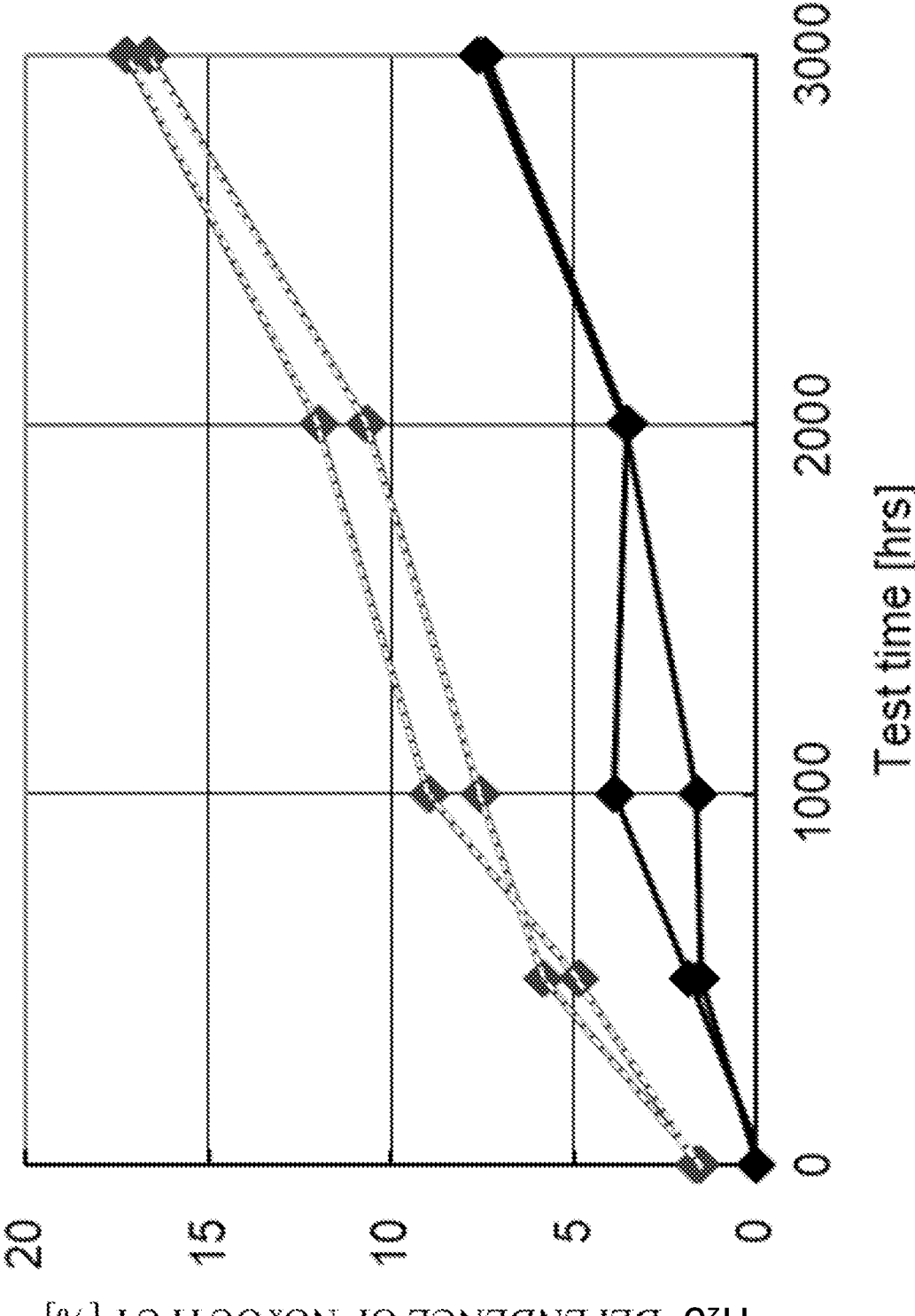
FIG. 14 is a graph showing differences in $H_2O$ dependence of $NO_x$ output with and without the porous diffusion layer that blocks the predetermined region of the flow path CH around the measurement electrode.
Figure 15:
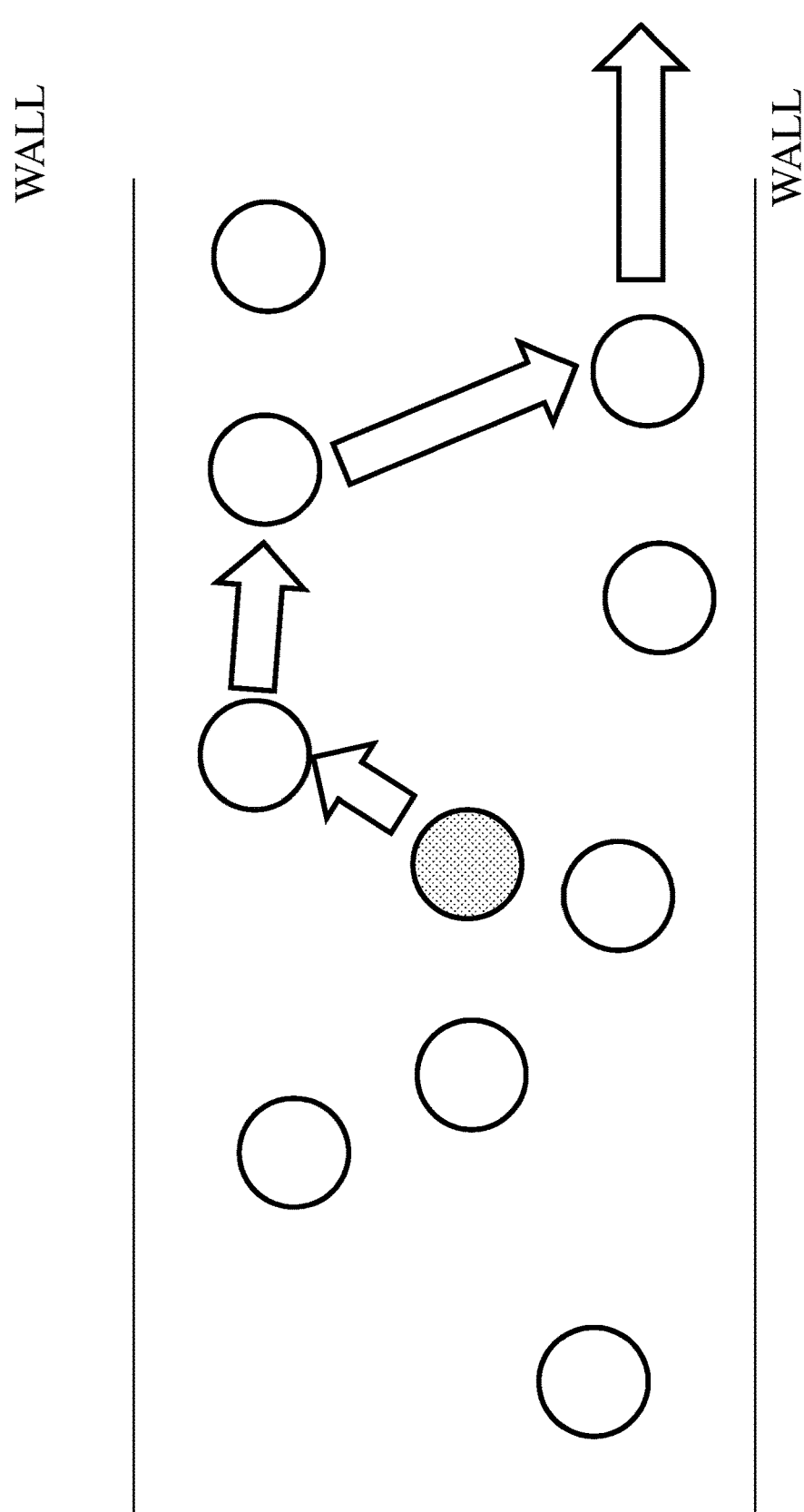
FIG. 15 shows an example of molecular diffusion.
Figure 16:
FIG. 16 shows an example of Knudsen diffusion.
Figure 16:
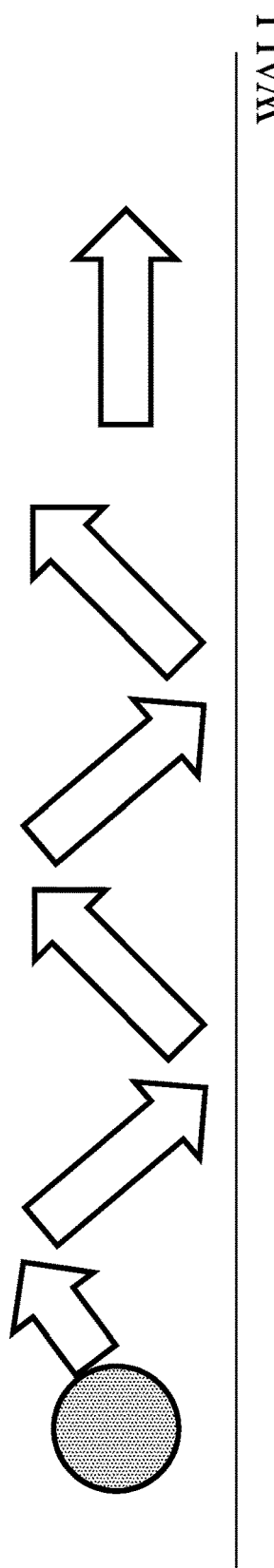

FIG. 14 is a graph showing differences in $H_2O$ dependence of $NO_x$ output with and without the porous diffusion layer that blocks the predetermined region of the flow path CH around the measurement electrode. Specifically, FIG. 14 shows differences in the $H_2O$ dependence of $NO_x$ output for the $NO_x$ sensors with the same structure, except for the presence of the porous diffusion layer (any of the porous diffusion layers 91, 91A, 91C, 91D, 91E, and 91F) that blocks the predetermined region of the flow path CH around the measurement electrode 44. In the graph in FIG. 14, the horizontal axis indicates time (drive time), and the vertical axis indicates $H_2O$ dependence of $NO_x$ sensitivity. Solid black lines indicate the change over time in the $H_2O$ dependence of $NO_x$ output of the $NO_x$ sensors that include the porous diffusion layer that blocks the predetermined region of the flow path CH around the measurement electrode 44. Dotted lines indicate the change over time in the $H_2O$ dependence of $NO_x$ output of the $NO_x$ sensors that do not include the porous diffusion layer that blocks the predetermined region of the flow path CH around the measurement electrode 44 (specifically, conventional $NO_x$ sensors that merely have a slit structure using a diffusion control portion).

The $H_2O$ dependence of $NO_x$ output was obtained based on the degree of change (change rate) in the $NO_x$ current (pump current Ip2) measured under the following conditions. That is, the $H_2O$ dependence of $NO_x$ output was calculated based on the change rate of the $NO_x$ current when a $NO_x$ concentration=500 ppm and a $H_2O$ concentration=15%, with a $NO_x$ concentration=500 ppm and a $H_2O$ concentration=3% as a base. The graph shown in FIG. 14 was created by plotting the $H_2O$ dependence of $NO_x$ output (change rate of the $NO_x$ current) at each drive time.

As shown in FIG. 14, the $H_2O$ dependence of $NO_x$ output significantly varies during the long-term drive test under high $H_2O$ concentration with the $NO_x$ sensors that do not include the porous diffusion layer around the measurement electrode 44 (conventional the $NO_x$ sensors that merely have a slit structure using a diffusion control portion). This is possibly because molecular diffusion is a dominant diffusion mode around the measurement electrode 44 in the conventional slit structure using a diffusion control portion. In contrast, the $NO_x$ sensors that include the porous diffusion layer make the diffusion mode around the measurement electrode 44 a mode of diffusing while repeatedly colliding with a wall face of a sufficiently narrow flow path, as in Knudsen diffusion, thus reducing the $H_2O$ dependence of $NO_x$ output, even under high $H_2O$ concentration. Further, the $NO_x$ sensors that include the porous diffusion layer can suppress fluctuations (change over time) in the $H_2O$ dependence of $NO_x$ output even under high $H_2O$ concentration by making the diffusion mode around the measurement electrode 44 a favorable mode, such as Knudsen diffusion.

Facts Confirmed Through Verifications

Some of the above-described test results (verification results) shown in Table 1 and FIGS. 13 and 14 can also be summarized as follows. That is, the $NO_x$ sensitivity and $NO_x$ output relative to high $H_2O$ concentration significantly vary in the long-term drive test under high $H_2O$ concentration with the gas sensors (conventional $NO_x$ sensors) that do not include the porous diffusion layer around the measurement electrode 44 and merely have the slit structure using a diffusion control portion. This is possibly because molecular diffusion is a dominant diffusion mode around the measurement electrode 44 in the conventional slit structure using a diffusion control portion.

The porous diffusion layer (e.g. the porous diffusion layer 91) having a porosity that is 5% or more and 25% or less was disposed upstream of the measurement electrode 44, and particularly, the distance d2 from the porous diffusion layer to the measurement electrode 44 was sufficiently small (specifically, 0.15 mm or less). The following effects were confirmed with the gas sensors that adopted this configuration. That is, these gas sensors can suppress fluctuations in $NO_x$ sensitivity. This is possibly because, when Knudsen diffusion is dominant around the measurement electrode 44, the ease of diffusion of $NO_x$ and $O_2$ gases is less likely to change even in the presence of $H_2O$ gas, which has a smaller molecular weight, and the increase in $NO_x$ and $O_2$ gases that reach the measurement electrode 44 is also smaller.

As indicated by the results in Table 1, it is preferable that the shortest distance (distance d1) from the outermost face of the leading end protection layer (200, 200G) to the gas inlet 10 is 0.2 mm or more. The gas sensor can prevent clogging in the vicinity of the gas inlet 10 and prevent a decrease in $NO_x$ sensitivity even if the gas sensor is exposed to a harsh environment with a large amount of a clogging material (e.g. poisonous substance), due to a large distance d1 from the outermost face of the leading end protection layer to the gas inlet 10. That is, the gas sensor can prevent clogging in the vicinity of the gas inlet and prevent a decrease in $NO_x$ sensitivity even if the gas sensor is exposed to a harsh environment with a large amount of poisonous substances or the like, as a result of the distance d1 from the outermost face of the leading end protection layer to the gas inlet 10 being 0.2 mm or more.

Furthermore, it is desirable that the leading end protection layer includes at least two layers, and the internal layer (the internal leading end protection layer 201) has a porosity larger (higher) than the porosity of the external layer (the external leading end protection layer 202). Particularly, it is desirable in the leading end protection layer that the proportion of the thickness of the internal layer to the thickness of the entire leading end protection layer is 30% or more and 90% or less. The likelihood of clogging in a layer closer to the gas inlet 10 (i.e. internal layer) caused by poisonous substances or the like can be reduced as a result of the proportion of the thickness of the internal layer, which has a porosity larger than the porosity of the external layer, to the thickness of the entire leading end protection layer being larger than that of the external layer.

LIST OF REFERENCE NUMERALS

100 Element substrate
101 Sensor element
200, 200G Leading end protection layer
201 Internal leading end protection layer
202 External leading end protection layer
10 Gas inlet
7 Measurement target gas flow portion (internal space)
44, 44D, 44E Measurement electrode
91, 91A, 91C, 91D, 91E, 91F Porous diffusion layer
18, 18B, 18C, 18D, 18E Fourth diffusion control portion (diffusion control portion)
19, 19B, 19C, 19D, 19E, 19F Third internal cavity (internal cavity)
CH, CH(B), CH(C), CH(D), CH(E), CH(F) Flow path

What is claimed is:

1. A gas sensor element comprising:
an element substrate having a surface in which a gas inlet is open, and including an internal space into which a measurement target gas is introduced from the gas inlet;
a leading end protection layer covering at least a face of the element substrate in which the gas inlet is open;
a measurement electrode provided in the internal space; and
a porous diffusion layer located at a position that is upstream of the measurement electrode in a flow direction of the measurement target gas and where a distance to the measurement electrode is 0.15 mm or less,
wherein the porous diffusion layer has a porosity that is 5% or more and 25% or less and is lower than a porosity of the leading end protection layer, and
the porous diffusion layer has a face orthogonal to the flow direction of the measurement target gas, the face accounting for 70% or more of a cross-section of a flow path of the measurement target gas, the cross-section being orthogonal to the flow direction of the measurement target gas,
the gas sensor element further comprising:
a diffusion control portion configured to apply predetermined diffusion resistance to the measurement target gas in the internal space,
wherein the diffusion control portion has a porosity lower than the porosity of the porous diffusion layer, and is located upstream of measurement electrode in the flow direction of the measurement target gas,
the flow path has at least one face defined by the diffusion control portion, and the porous diffusion layer is in contact with an upper or lower surface of the diffusion control portion in a direction orthogonal to the flow direction of the measurement target gas.

2. The gas sensor element according to claim 1,
wherein the porous diffusion layer is in contact with the diffusion control portion and a face defining the internal space.

3. The gas sensor element according to claim 2,
wherein the flow path has at least two faces defined by the diffusion control portion.

4. The gas sensor element according to claim 2,
wherein a distance from an outermost face of the leading end protection layer to the gas inlet is 0.2 mm or more.

5. The gas sensor element according to claim 2,
wherein the leading end protection layer includes at least:
an internal leading end protection layer in contact with the face of the element substrate in which the gas inlet is open; and
an external leading end protection layer constituting an outermost face of the leading end protection layer,
the internal leading end protection layer has a porosity larger than a porosity of the external leading end protection layer, and
the internal leading end protection layer has a thickness that is 30% or more and 90% or less of a thickness of the leading end protection layer.

6. A gas sensor comprising the gas sensor element according to claim 2 and configured to measure an amount of a specific gas component in the measurement target gas.

7. The gas sensor element according to claim 1,
wherein the flow path has at least two faces defined by the diffusion control portion.

8. The gas sensor element according to claim 1,
wherein a distance from an outermost face of the leading end protection layer to the gas inlet is 0.2 mm or more.

9. The gas sensor element according to claim 1,
wherein the leading end protection layer includes at least:
an internal leading end protection layer in contact with the face of the element substrate in which the gas inlet is open; and
an external leading end protection layer constituting an outermost face of the leading end protection layer,
the internal leading end protection layer has a porosity larger than a porosity of the external leading end protection layer, and
the internal leading end protection layer has a thickness that is 30% or more and 90% or less of a thickness of the leading end protection layer.

10. A gas sensor comprising the gas sensor element according to claim 1 and configured to measure an amount of a specific gas component in the measurement target gas.

* * * * *